US012757893B2

(12) United States Patent
Church et al.

(10) Patent No.: US 12,757,893 B2
(45) Date of Patent: Oct. 13, 2026

(54) METHODS FOR CRYOGENIC STORAGE

(71) Applicant: JUNO THERAPEUTICS, INC., Seattle, WA (US)

(72) Inventors: Sara Elizabeth Church, Seattle, WA (US); Jon Charles Gunther, Seattle, WA (US); Kathryn Pollock, Seattle, WA (US)

(73) Assignee: Juno Therapeutics, Inc., Seattle, WA (US)

( * ) Notice: Subject to any disclaimer, the term of this patent is extended or adjusted under 35 U.S.C. 154(b) by 1540 days.

(21) Appl. No.: 16/493,828

(22) PCT Filed: Mar. 14, 2018

(86) PCT No.: PCT/US2018/022522

§ 371 (c)(1),
(2) Date: Sep. 13, 2019

(87) PCT Pub. No.: WO2018/170188

PCT Pub. Date: Sep. 20, 2018

(65) Prior Publication Data

US 2020/0077644 A1 Mar. 12, 2020

Related U.S. Application Data

(60) Provisional application No. 62/471,343, filed on Mar. 14, 2017.

(51) Int. Cl.

| | |
|---|---|
| ***A01N 1/162*** | (2025.01) |
| ***A01N 1/10*** | (2025.01) |
| ***A01N 1/147*** | (2025.01) |
| ***A61K 40/11*** | (2025.01) |
| ***A61K 40/31*** | (2025.01) |
| ***A61K 40/42*** | (2025.01) |

(52) U.S. Cl.

CPC ............... *A01N 1/162* (2025.01); *A01N 1/10* (2025.01); *A01N 1/147* (2025.01); *A61K 40/11* (2025.01); *A61K 40/31* (2025.01); *A61K 40/4211* (2025.01)

(58) Field of Classification Search

None

See application file for complete search history.

(56) References Cited

U.S. PATENT DOCUMENTS

| | | | |
|---|---|---|---|
| 4,452,773 | A | 6/1984 | Molday |
| 4,795,698 | A | 1/1989 | Owen |
| 5,200,084 | A | 4/1993 | Liberti |
| 5,219,740 | A | 6/1993 | Miller |
| 6,040,177 | A | 3/2000 | Riddell |
| 6,207,453 | B1 | 3/2001 | Maass et al. |
| 6,410,319 | B1 | 6/2002 | Raubitschek et al. |
| 6,451,995 | B1 | 9/2002 | Cheung et al. |
| 7,070,995 | B2 | 7/2006 | Jensen |
| 7,265,209 | B2 | 9/2007 | Jensen |
| 7,354,762 | B2 | 4/2008 | Jensen |
| 7,446,179 | B2 | 11/2008 | Jensen |
| 7,446,190 | B2 | 11/2008 | Sadelain |
| 7,446,191 | B2 | 11/2008 | Jensen |
| 8,324,353 | B2 | 12/2012 | Jensen |
| 8,339,645 | B2 | 12/2012 | Nakawaki et al. |
| 8,389,282 | B2 | 3/2013 | Sadelain |
| 8,497,118 | B2 | 7/2013 | Jensen |
| 8,709,797 | B2 | 4/2014 | Woods |
| 8,802,374 | B2 | 8/2014 | Jensen |
| 8,822,647 | B2 | 9/2014 | Jensen |
| 8,911,993 | B2 | 12/2014 | June et al. |
| 8,936,905 | B2 | 1/2015 | Woods et al. |
| 9,565,854 | B2 | 2/2017 | Woods |
| 2002/0131960 | A1 | 9/2002 | Sadelain |
| 2005/0158846 | A1 | 7/2005 | Hiroki et al. |
| 2011/0003380 | A1 | 1/2011 | Miltenyi |
| 2013/0149337 | A1 | 6/2013 | Cooper |
| 2013/0287748 | A1 | 10/2013 | June |
| 2014/0271635 | A1 | 9/2014 | Brogdon et al. |
| 2015/0202286 | A1 | 7/2015 | June et al. |
| 2015/0344844 | A1 * | 12/2015 | Better ................ A61K 39/0011 435/377 |
| 2016/0122782 | A1 | 5/2016 | Crisman et al. |
| 2016/0158359 | A1 | 6/2016 | Gilbert |
| 2016/0184330 | A1 | 6/2016 | Sordillo et al. |
| 2016/0206656 | A1 | 7/2016 | Gilbert et al. |
| 2020/0191774 | A1 | 6/2020 | Christin et al. |

FOREIGN PATENT DOCUMENTS

| | | |
|---|---|---|
| CN | 105685017 | 6/2016 |
| EP | 0452342 | 10/1991 |
| EP | 2537416 | 12/2012 |
| JP | 2005-332046 | 12/2005 |
| WO | WO 1992/008796 | 5/1992 |
| WO | WO 1994/028143 | 12/1994 |

(Continued)

OTHER PUBLICATIONS

US 8,252,592 B2, 08/2012, Sadelain (withdrawn)
Jang TH, Park SC, Yang JH, Kim JY, Seok JH, Park US, Choi CW, Lee SR, Han J. Cryopreservation and its clinical applications. Integr Med Res. Mar. 2017;6(1):12-18. doi: 10.1016/j.imr.2016.12.001. Epub Jan. 10, 2017. PMID: 28462139; PMCID: PMC5395684. (Year: 2017).*

(Continued)

*Primary Examiner* — Christopher M Babic

*Assistant Examiner* — Alyssa G Weston

(74) *Attorney, Agent, or Firm* — Morrison & Foerster LLP

(57) ABSTRACT

The present disclosure relates to methods and compositions and articles of manufacture, related to cryogenic storage, such as for cryogenically freezing and storing cells from a donor's blood, and methods of processing an apheresis sample.

35 Claims, No Drawings

Specification includes a Sequence Listing.

(56) References Cited

FOREIGN PATENT DOCUMENTS

| | | | |
|---|---|---|---|
| WO | WO 1996/013593 | | 5/1996 |
| WO | WO 1996/018105 | | 6/1996 |
| WO | WO 1999/018129 | | 4/1999 |
| WO | WO 1999/060120 | | 11/1999 |
| WO | WO 2000/014257 | | 3/2000 |
| WO | WO 2003/020763 | | 3/2003 |
| WO | WO 2004/033685 | | 4/2004 |
| WO | WO 2006/000830 | | 1/2006 |
| WO | WO 2009/072003 | | 6/2009 |
| WO | WO 2010/033140 | | 3/2010 |
| WO | WO 2011/044186 | | 4/2011 |
| WO | WO 2011/056894 | | 5/2011 |
| WO | WO 2012/129514 | | 9/2012 |
| WO | WO 2013/019857 | | 2/2013 |
| WO | WO 2013/071154 | | 5/2013 |
| WO | WO 2013/123061 | | 8/2013 |
| WO | WO 2013/126726 | | 8/2013 |
| WO | WO 2013/166321 | | 11/2013 |
| WO | WO 2014/011984 | | 1/2014 |
| WO | WO 2014/031687 | | 2/2014 |
| WO | WO 2014/055668 | | 4/2014 |
| WO | WO 2015/157384 | | 10/2015 |
| WO | WO 2015/164675 | | 10/2015 |
| WO | WO 2015/164745 | | 10/2015 |
| WO | WO 2016/033570 | | 3/2016 |
| WO | WO 2016/057651 | A1 | 4/2016 |
| WO | WO 2016/064929 | | 4/2016 |
| WO | WO 2016/069283 | | 5/2016 |
| WO | WO 2016/073602 | | 5/2016 |
| WO | WO 2016/089825 | | 6/2016 |
| WO | WO 2016/115559 | | 7/2016 |
| WO | WO 2017/015427 | | 1/2017 |
| WO | WO 2017/096331 | | 6/2017 |
| WO | WO 2017/117112 | A1 | 7/2017 |
| WO | WO 2017/214207 | | 12/2017 |
| WO | WO 2018/148567 | | 8/2018 |
| WO | WO 2018/157171 | | 8/2018 |
| WO | WO 2018/223101 | | 12/2018 |
| WO | WO 2019/109053 | | 6/2019 |

OTHER PUBLICATIONS

CryoStor® CS10 Technical Data Sheet. STEMCELL Technologies. (2022). https://www.stemcell.com/products/cryostor-cs10.html (Year: 2022).*

CryoStore Freezing Bag—OriGen Biomedical. (2023). OriGen Biomedical. https://www.origen.com/products/cryopreservation/cryostore-freezing-bag (Year: 2023).*

KryoSure® Cryopreservation Bags. (2025). Saint-Gobain. https://www.biopharm.saint-gobain.com/cell-therapy/cryopreservation/kryosure-cryopreservation-bags (Year: 2025).*

Alonso-Camino et al., "CARbodies: Human Antibodies Against Cell Surface Tumor Antigens Selected From Repertoires Displayed on T Cell Chimeric Antigen Receptors," Mol Ther Nucl Acids (2013) 2: e93.

Barret, D.M. et al. (2014, e-pub. Nov. 20, 2013). "Chimeric Antigen Receptor Therapy for Cancer," Annu Rev Med. (2014);65:333-347.

Bergamaschi et al., "Circulating IL-15 exists as heterodimeric complex with soluble IL-15Rα in human and mouse serum," Blood. (2012) 120(1):e1-8.

Bishnoi et al. "Serum interleukin (IL)-15 as a biomarker of Alzheimer's disease." PLoS One (2015)10.2 : e0117282.

Boris-Lawrie, K.A. et al. "Recent advances in retrovirus vector technology", Curr Opin Genet Dev. (1993) 3(1):102-109.

Brash et al., "Strontium phosphate transfection of human cells in primary culture: stable expression of the simian virus 40 large-T-antigen gene in primary human bronchial epithelial cells," Mol. Cell Biol. (1987) 7: 2031-2034.

Brudno et al., "Toxicities of chimeric antigen receptor T cells: recognition and management," Blood (May 2016) 127(26):3321-3330.

Buhl et al., "Controlled-rate freezer cryopreservation of highly concentrated peripheral blood mononuclear cells results in higher cell yields and superior autologous T-cell stimulation for dendritic cell-based immunotherapy," Cancer Immunol Immunother. (2012) 61(11): 2021-31.

Burns et al., "Vesicular stomatitis virus G glycoprotein pseudotyped retroviral vectors: concentration to very high titer and efficient gene transfer into mammalian and nonmammalian cells," Proc. Natl. Acad. Sci. USA (1993) 90:8033-8037.

Carlens et al., "Ex vivo T lymphocyte expansion for retroviral transduction: influence of serum-free media on variations in cell expansion rates and lymphocyte subset distribution," Exp Hematol (2000) 28(10): 1137-46.

Cavalieri et al., "Human T lymphocytes transduced by lentiviral vectors in the absence of TCR activation maintain an intact immune competence," Blood (2003) 102(2): 497-505.

Cheadle et al., "Chimeric antigen receptors for T-cell based therapy," Methods Mol Biol. (2012);907:645-66.

Chervin et al., "Engineering higher affinity T cell receptors using a T cell display system." J Immunol Methods. (2008) 339(2):175-84.

Chicaybam et al., "An efficient low cost method for gene transfer to T lymphocytes," PLoS ONE (2013) 8(3): e60298.

Cho et al., "Human mammalian cell sorting using a highly integrated micro-fabricated fluorescence-activated cell sorter (microFACS)," Lab Chip (2010) 10: 1567-1573.

Chothia et al., "The outline structure of the T-cell alpha beta receptor," The EMBO journal (1988) 7(12):3745-55.

Cooper et al., "T-cell clones can be rendered specific for CD19: toward the selective augmentation of the graft-versus-B-lineage leukemia effect," Blood (2003) 101:1637-1644.

Davila et al., "CD19 CAR-targeted T cells induce long-term remission and B Cell Aplasia in an immunocompetent mouse model of B cell acute lymphoblastic leukemia," PLoS ONE (2013) 8(4): e61338.

De Loecker et al., "Effects of cell concentration on viability and metabolic activity during cryopreservation," Cryobiology. (1998) 37(2):103-9.

Dumont et al., "Involvement of two specific causes of cell mortality in freeze-thaw cycles with freezing to -196 degrees C," Appl Environ Microbiol. (2006) 72(2):1330-5.

Fedorov et al., "PD-1- and CTLA-4-based inhibitory chimeric antigen receptors (iCARs) divert off-target immunotherapy responses," Sci. Transl. Medicine (2013) 5(215):215ra172.

Friedl et al., " T lymphocyte locomotion in a three-dimensional collagen matrix: Expression and function of cell adhesion molecules," J Immunol. (1995) 154: 4973-4985.

Godin et al., "Microfluidics and photonics for Bio-System-on-a-Chip: a review of advancements in technology towards a microfluidic flow cytometry chip," J Biophoton. (2008) 1(5):355-376.

Holler et al., "In vitro evolution of a T cell receptor with high affinity for peptide/MHC." Proc Natl Acad Sci U S A (2000) 97(10):5387-92.

Holler et al., "TCRs with high affinity for foreign pMHC show self-reactivity," Nature immunology (2003) 4(1):55-62.

Huang et al., "DNA transposons for modification of human primary T lymphocytes," Methods Mol Biol (2009) 506: 115-126.

Hudecek et al., "Receptor affinity and extracellular domain modifications affect tumor recognition by ROR1-specific chimeric antigen receptor T cells," Clin. Cancer Res. (2013) 19:3153.

Imai et al. "Chimeric receptors with 4-1BB signaling capacity provoke potent cytotoxicity against acute lymphoblastic leukemia." Leukemia (2004) 18.4 : 676-684.

Janeway et al., "Immunobiology: The Immune System in Health and Disease," (1997) 3rd Ed., Current Biology Publications, p. 4:33.

Johnston, et al., "Biolistic transformation: microbes to mice," Nature (1990) 346: 776-777.

Jores et al., "Resolution of hypervariable regions in T-cell receptor beta chains by a modified Wu-Kabat index of amino acid diversity," Proceedings of the National Academy of Sciences (1990) 87(23):9138-42.

Kimbrel et al., "Next-generation stem cells—ushering in a new era of cell-based therapies," Nat Rev Drug Discov. (2020) 19(7):463-479.

(56) References Cited

OTHER PUBLICATIONS

Klaver et al., "Adoptive T-cell therapy: A need for standard immune monitoring," (2015) Immunotherapy 7(5)513-33.
Klebanoff et al., "Sorting through subsets: which T-cell populations mediate highly effective adoptive immunotherapy?," J Immunother. (2012) 35(9): 651-660.
Kochenderfer et al., "Treating B-cell cancer with T cells expressing anti-CD19 chimeric antigen receptors," Nature Reviews Clinical Oncology (2013) 10, 267-276.
Kochenderfer et al., "B-cell depletion and remissions of malignancy along with cytokine-associated toxicity in a clinical trial of anti-CD19 chimeric-antigen-receptor-transduced T cells," Blood (2012) 119(12):2709-2720.
Koste et al., "T-cell receptor transfer into human T cells with ecotropic retroviral vectors," Gene Therapy (2014) 21: 533-538.
Kotb et al., "Bacterial pyrogenic exotoxins as superantigens," Clinical Microbiology Reviews (1995) 8:411-426.
Kurucz et al., "A bacterially expressed single-chain Fv construct from the 2B4 T-cell receptor." Proceedings of the National Academy of Sciences. (1993) 90(9):3830-4.
Lefranc et al., "IMGT unique numbering for immunoglobulin and T cell receptor variable domains and Ig superfamily V-like domains," Dev Comp Immunol (2003) 27(1):55-77.
Li et al., "Directed evolution of human T-cell receptors with picomolar affinities by phage display," Nature biotechnology (2005) 23(3):349-54.
Lupton S. D. et al., "Dominant positive and negative selection using a hygromycin phosphotransferase-thymidine kinase fusion gene," Mol. and Cell Biol. (1991) 11(6): 3374-3378.
Manuri et al., "piggyBac transposon/transposase system to generate CD19-specific T cells for the treatment of B-lineage malignancies," Hum Gene Ther (2010) 21(4): 427-437.
Mazur et al., "Influence of cell concentration on the contribution of unfrozen fraction and salt concentration to the survival of slowly frozen human erythrocytes," Cryobiology. (1985) 22(6):509-36.
Immunomagnetic Cell Separation. Methods in Molecular Medicine, vol. 58: Metastasis Research Protocols, vol. 2: Cell Behavior In Vitro and In Vivo, p. 17-25 Edited by: S. A. Brooks and U. Schumacher © Humana Press Inc., Totowa, NJ.
Miller et al., "Improved retroviral vectors for gene transfer and expression," BioTechniques (1989) 7:980-990.
Miller et al., "Retrovirus packaging cells," Human Gene Therapy (1990) 1:5-14.
Morozova et al., Prospects of genetic programming of T-cells in adoptive immunotherapy of malignant neoplasms, Sechenovsky Vestnik, 2016, No. 3 (25), p. 23-28. Reference in Russian; English Abstract provided.
Mullen et al., "Transfer of the bacterial gene for cytosine deaminase to mammalian cells confers lethal sensitivity to 5-fluorocytosine: a negative selection system," Proc Natl Acad Sci USA. (1992) 89(1):33-7.
Park et al., "Treating cancer with genetically engineered T cells," Trends Biotechnol. (2011) 29(11): 550-557.
Porter et al., "Chimeric antigen receptor T cells persist and induce sustained remissions in relapsed refractory chronic lymphocytic leukemia," Sc.i Trans. Med. (Sep. 2015) 7(303): 303ra139.
Riddell et al., "Phase I Study of Cellular Adoptive Immunotherapy Using Genetically Modified CD8+ HIV-Specific T Cells for HIV Seropositive Patients Undergoing Allogeneic Bone Marrow Transplant. Fred Hutchinson Cancer Research Center and the University of Washington," Human Gene Therapy (1992) 3:319-338.
Sadelain et al., "The basic principles of chimeric antigen receptor design," Cancer Discov. (2013) 3(4): 388-398.
Santomasso et al., "The Other Side of CAR T-Cell Therapy: Cytokine Release Syndrome, Neurologic Toxicity, and Financial Burden," Am Soc Clin Oncol Educ Book. (2019) 39:433-444.
Scarpa et al., "Characterization of recombinant helper retroviruses from Moloney-based vectors in ecotropic and amphotropic packaging cell lines," Virology (1991) 180:849-852.
Schlueter et al., "Specificity and binding properties of a single-chain T cell receptor." Journal of molecular biology. (1996) 256(5):859-69.
Schuler et al., "SYFPEITHI: database for searching and T-cell epitope prediction." Methods Mol Biol. (2007);409:75-93.
Schulz et al., "Towards a xeno-free and fully chemically defined cryopreservation medium for maintaining viability, recovery, and antigen-specific functionality of PBMC during long-term storage," J Immunol Methods. (2012) 382(1-2):24-31.
Sharma et al., "Efficient sleeping beauty DNA transposition from DNA minicircles," Molec Ther Nucl Acids (2013) 2, e74.
Singh et al., "ProPred: prediction of HLA-DR binding sites." Bioinformatics. (2001) 17(12):1236-7.
Soo Hoo et al., "Characterization of a single-chain T-cell receptor expressed in *Escherichia coli.*" Proceedings of the National Academy of Sciences. (1992) 89(10):4759-63.
Tang et al., "Opportunities and Challenges of Chimeric Antigen Receptor Modified T Cell Immunotherapy," PLA Journal of Medicine (2015) 27(1): 12-25. Article in Chinese; English abstract included.
Tao et al., "Interleukin-6 up-regulates the expression of interleukin-15 is associated with MAPKs and PI3-K signaling pathways in the human keratinocyte cell line, HaCaT," Mol Biol Rep. (2012) 39(4):4201-5.
Terakura et al., "Generation of CD19-chimeric antigen receptor modified CD8+ T cells derived from virus-specific central memory T cells," Blood (2012) 1:72-82.
Turtle et al., "Engineered T cells for anti-cancer therapy," Curr. Opin. Immunol. (2012) 24(5): 633-39.
Turtle et al., "Biomarkers of Cytokine Release Syndrome and Neurotoxicity after CD19 CAR-T Cells and Mitigation of Toxicity By Cell Dose," Blood (2016) 128(22):1852.
Van Tendeloo et al., "High-level transgene expression in primary human T lymphocytes and adult bone marrow CD34+ cells via electroporation-mediated gene delivery," Gene Therapy (2000) 7(16): 1431-1437.
Verhoeyen et al., "Lentiviral vector gene transfer into human T cells," Methods Mol Biol. (2009) 506: 97-114.
Wang et al., "Phenotypic and functional attributes of lentivirus-modified CD19-specific human CD8+ central memory T cells manufactured at clinical scale," J Immunother. (2012) 35(9):689-701.
Wigler et al., "Transfer of purified herpes virus thymidine kinase gene to cultured mouse cells," Cell (1977) 11(1):223-232.
Wu et al., "Adoptive T-cell therapy using autologous tumor-infiltrating lymphocytes for metastatic melanoma: current status and future outlook," Cancer (2012) 18(2): 160-75.
Wulfing et al., "Correctly folded T-cell receptor fragments in the periplasm of *Escherichia coli:* Influence of folding catalysts." Journal of molecular biology. (1994) 242(5):655-69.
Allen et al., "Autologous lymphapheresis for the production of chimeric antigen receptor T cells," Transfusion, vol. 57, No. 5, pp. 1133-1141, Feb. 24, 2017.
Brentjens et al., "CD19-Targeted T Cells Rapidly Induce Molecular Remissions in Adults with Chemotherapy-Refractory Acute Lymphoblastic Leukemia," Science Translational Medicine, vol. 5, No. 177, p. 177ra38, Mar. 20, 2013.
International Search Report & Written Opinion, dated Sep. 21, 2018, PCT/US2018/022522.
Lu et al., "A Rapid Cell Expansion Process for Production of Engineered Autologous CAR-T Cell Therapies," Human Gene Therapy Methods, vol. 27, No. 6, pp. 209-218, Dec. 1, 2016.
Galeano Niño et al., "Antigen-specific T cells fully conserve antitumour function following cryopreservation," Immunology and Cell Biology, vol. 94, No. 4, pp. 411-418, Jan. 12, 2016.
PCT International Search Report & Written Opinion, dated Sep. 21, 2018, PCT/US2018/022522 (21 pages).
Cryopreservation of Mammalian Cells, ThermoFisher Scientifc, p. 1 [retrieved from internet May 2, 2024] <URL: https://web.archive.org/web/20160601000000*/https://www.thermofisher.com/au/en/home/references/gibco-cell-culture-basics/cell-culture-protocols/cryopreservation-of-mammalian-cells.html published on Aug. 17, 2016 as per Wayback machine.

(56) References Cited

OTHER PUBLICATIONS

Davila et al., "Efficacy and toxicity management of 19-28z CAR T cell therapy in B cell acute lymphoblastic leukemia," Sci Transl Med (2014) 6:224ra25, 10 pages.
Kielberg et al., "Cryopreservation of Mammalian Cells-Protocols" Thermoscientific tech note, (2010), 2 pages. Retrieved from https://assets.fishersci.com/TFS-Assets/LSG/Application-Notes/D19575.pdf.
Turtle et al., "CD19 CAR-T cells of defined CD4+:CD8+ composition in adult B cell ALL patients," J. Clin. Invest. (Jun. 2016) 126(6):2123-38.
Zhang Mei (ed. ), "New Technologies and Progress in Clinical Diagnosis and Treatment of Hematological Diseases, National-level Hematology CME Textbook and Shaanxi Provincial Hematology Diagnosis and Treatment Quality Control Training Series," Shaanxi Science and Technology Press, Mar. 2007, 1st ed., 1st printing, pp. 351-352 (Chinese). English machine translation provided.

* cited by examiner

METHODS FOR CRYOGENIC STORAGE

RELATED APPLICATION INFORMATION

This application is a national stage entry application of International Patent Application No. PCT/US2018/022522, filed Mar. 14, 2018, which claims priority to U.S. Provisional Patent Application No. 62/471,343, filed on Mar. 14, 2017, the entire contents of which are incorporated herein by reference.

SEQUENCE LISTING

The instant application contains a Sequence Listing, which has been submitted electronically in ASCII format and is hereby incorporated by reference in its entirety. Said ASCII copy is named SEQLTXT-1.txt and is 1 KB in size.

SUMMARY

Cell therapy is a technique in which cells are administered to a recipient to achieve a therapeutic purpose. For any given recipient, the administered cells may originate from another person or from the recipient herself. The latter case may be called autologous cell therapy, that is, the administration of cells back into the recipient from whom the cells were collected. Advantages of autologous cell therapy can include a reduced chance that the recipient's body would reject the administered cells, since the donor from whom the cells are collected is the recipient.

For cell therapy, how and when the cells are collected from a donor, and how the cells are treated after collection and before administration, may affect the therapy's efficacy and availability, e.g., how quickly the cells may be administered to a recipient when needed.

To these ends, provided are methods, systems and compositions, and articles of manufacture, for cryogenic storage of cells and cell compositions and/or engineering and/or administration thereof to subjects such as recipients. Among the advantages of the embodiments in some aspects are to, among other things, enhance the availability, efficacy, and/or other aspects of cell therapy. The methods may also or alternatively provide benefits to other medical or research processes that use cells collected from a donor.

In some aspects, the present disclosure relates to methods of cryogenic storage, processing, engineering, and administering of cells, and related articles, compositions, and systems involving apheresis collected before the patient needs cell therapy, and cryopreserved for later use.

In some aspects, the cells and compositions and articles of the present disclosure are those that can be used, for example, for subsequent therapeutic treatment of a disease or condition, such as in the donor and/or another recipient. In some embodiments, the methods involve cryogenically storing cells from a donor's blood. The cryogenically stored cells may, in some embodiments, then be used for cell therapy to treat a disease or condition.

In some embodiments, the cells are collected after the donor is diagnosed with a disease or condition, and before the donor has received one or more of the following: any initial treatment for the disease or condition, any targeted treatment or any treatment labeled for treatment for the disease or condition, or any treatment other than radiation and/or chemotherapy. In some embodiments, the cells are collected after a first relapse of a disease following initial treatment for the disease, and before the donor or subject receives subsequent treatment for the disease. The initial and/or subsequent treatments may be, according to certain embodiments, a therapy other than cell therapy. In some embodiments, the collected cells may be used in a cell therapy following initial and/or subsequent treatments.

In some embodiments, the cells are collected after a second relapse of a disease following a second line of treatment for the disease, and before the donor or subject receives subsequent treatment for the disease. In some embodiments, patients are identified as being likely to relapse after a second line of treatment, for example, by assessing certain risk factors. In some embodiments, the risk factors are based on disease type and/or genetics, such as double-hit lymphoma, primary refractory cancer, or activated B-cell lymphoma. In some embodiments, the risk factors are based on clinical presentation, such as early relapse after first-line treatment, or other poor prognostic indicators after treatment (e.g., IPI>2).

In some embodiments, the cells are collected before the donor or subject is diagnosed with a disease. In some aspects, the donor or subject may be determined to be at risk for developing a disease, or may elect to bank or store cells without being deemed at risk for developing a disease or being diagnosed with a disease in the event that cell therapy is required at a later stage in life. In some embodiments, a donor or subject may be deemed at risk for developing a disease based on factors such as genetic mutations, genetic abnormalities, genetic disruptions, family history, protein abnormalities (such as deficiencies with protein production and/or processing), and lifestyle choices that may increase the risk of developing a disease. In some embodiments, the cells are collected as a prophylactic.

In some embodiments, the cells are stored, or banked, for a period of time greater than or equal to 12 hours, 24 hours, 36 hours, or 48 hours. In some embodiments, the cells are stored or banked for a period of time greater than or equal to 1 week, 2 weeks, 3 weeks, or 4 weeks. In some embodiments, the cells are placed into long-term storage or long-term banking. In some aspects, the cells are stored for a period of time greater than or equal to 1 month, 2 months, 3 months, 4 months, 5 months, 6 months, 7 months, 8 months, 9 months, 10 months, 11 months, 1 year, 2 years, 3 years, 4 years, 5 years, 6 years, 7 years, 8 years, 9 years, 10 years, 11 years, 12 years, 13 years, 14 years, 15 years, 16 years, 17 years, 18 years, 19 years, 20 years, 25 years, 30 years, 35 years, 40 years, or more.

The disclosure also relates in some aspects to methods of processing an apheresis sample. In some embodiments, the methods involve shipping in a cooled environment to a storage facility an apheresis sample taken from a donor, and cryogenically storing the apheresis sample at the storage facility. In some embodiments, before shipping, the sample is processed, for example, by selecting T cells, such as $CD4^+$ and/or $CD8^+$ T cells. In some embodiments, such processing is performed after shipping and before cryogenically storing the sample. In some embodiments, the processing is performed after thawing the sample following cryogenically storage.

In some embodiments, an advantage of the methods according to embodiments described includes improved efficiency and/or effectiveness of cell therapies. By allowing donors to store their cells at a stage when the donors, and thus their cells, have not undergone extensive treatment for a disease and/or prior to contracting of a disease or condition or diagnosis thereof, such cells may have certain advantages for use in cell therapy compared to cells harvested after one or after multiple rounds of treatment. For example, cells harvested before one or more rounds of treatment may be healthier, may exhibit higher levels of certain cellular activities, may grow more rapidly, and/or may be more receptive to genetic manipulation than cells that have undergone several rounds of treatment. Another example of an advantage according to embodiments described herein may include convenience. For example, by collecting, optionally processing, and storing a donor's cells before they are needed for cell therapy, the cells would be readily available if and when a recipient later needs them. This could increase apheresis lab capacity, providing technicians with greater flexibility for scheduling the apheresis collection process.

In some embodiments, the cells and/or compositions and/or articles of manufacture, such as containers (e.g., cell vials or bags) containing the cells, are marked with one or more code or other identifier, such as for cataloging of cells and samples during processing, cryopreservation, and/or storage, such as during long-term storage. In some embodiments, the systems and articles include a plurality of containers, each comprising a cryopreserved cell composition, such as one generated according to embodiments of the provided methods, where each of a plurality of the containers contains cryopreserved samples obtained from a different donor. In some embodiments, the containers are marked with one or more identifiers, such as a barcode, radio frequency identification (RFID) tag, or other identifier corresponding to or indicating the identity of one or more of: the donor, sample, composition, vial, container, condition, disease, collection facility, hospital, and/or recipient. In some aspects, additional information included on or affixed to the containers includes information regarding date of apheresis collection and/or cryopreservation and/or expiration date and/or location within a bank or storage facility. In some embodiments, the code corresponds to a code appearing on a patient identity bracelet or hospital or medical or collection facility system or paperwork, such as the donor or associated facility.

Suitable coding or marking methods or systems include but are not limited to encoding using tags in printed, magnetic, or electronic form, which may be read by light, electronic, or magnetic means, such as barcodes, QR codes, RFIDs, or transponders, such as light activated micro-transponders, low cost silicon devices which store a unique 30 bit read-only identity code and emit the code as radio frequency signal when powered and interrogated with a light emitting reader device. In some embodiments, all processing components (sample collection tube, cell purification components, cell culture and expansion components, etc.) are pre-registered in a facility component registry where each component's function and intended stage of use in the processing workflow is logged against the component's unique identifier code. In some embodiments, a transponder is used, and in some aspects refers to any method or article for encoding a unique sample identity which may be read.

In some embodiments, at various stages of, e.g., at each stage in, the methods, e.g. the processing workflow and/or prior to or at administration to the recipient, the one or more identifier code is read into a record, such as a unique patient specific record in a central database, and/or is used to confirm the identity of the sample and/or patient from which it has been derived or is to be administered, and/or other information about the sample and/or its collection or processing, and/or to confirm correct chain of custody.

DETAILED DESCRIPTION

The following detailed description and examples illustrate certain embodiments of the present disclosure. Those of skill in the art will recognize that there are numerous variations and modifications of this disclosure that are encompassed by its scope. Accordingly, the description of certain embodiments should not be deemed as limiting.

As used here, the term "cryogenically storing" or "cryogenic storage" generally refers to storing a sample, for example, a sample containing cells at a temperature from −210° C. to −80° C. and in a condition such that the cells are capable of being thawed after a period of such storage, such that upon or following thawing, at least a portion of or substantial portion of cells in the sample remain viable and/or retain at least a portion of a biological function thereof. In one aspect, the cell sample is capable of being thawed such that at least a certain percentage, such as at or about or more than 20%, 30%, 40%, 50%, 60%, 70%, 80%, 90%, or 100% of the cells in the sample remain viable and/or negative for an apoptotic marker or indicator thereof, such as a cleaved caspase and/or AnnexinV staining.

As used here, the term cryogenically freezing means lowering the temperature of a sample, for example, a sample containing cells, to a temperature from −210 to −80° C.

In some embodiments, the term enrich or enrichment as used herein in the context of a sample containing cells means separating, selecting, or purifying a type or types of cells from the sample, so that a higher concentration of the type or types of cells is obtained. The term "enrich" does not necessarily, but can in some embodiments, include achieving absolute or near-absolute purity of the cells.

As used herein, the subject or donor is a mammal, such as a human or other animal, and typically is human. In some embodiments, the subject, e.g., patient, to whom the cells, cell populations, or compositions are administered is a mammal, typically a primate, such as a human. In some embodiments, the primate is a monkey or an ape. The subject can be male or female and can be any suitable age, including infant, juvenile, adolescent, adult, and/or geriatric subjects. In some embodiments, the subject is a non-primate mammal, such as a rodent.

In some embodiments, the term "freezing solution" means a solution that, when combined with a sample containing cells, for example, an apheresis sample, assists in preserving one or more biological functions of the cells during a process of cooling, cryogenically freezing, and/or cryogenically storing the sample or the cells. In some embodiments, the terms freezing solution and cryogenic medium are interchangeable.

In some embodiments, the term "post-cryogenically modifying" or "post-cryogenic modification" as used herein in the context of a cryogenically-stored sample containing cells means a process applied to the sample after thawing the cells.

In some embodiments, the term "relapse" as used herein generally means a return of signs or symptoms of a disease after a period of improvement.

Apheresis generally refers to a process for collecting a donor's or a subject's blood. The process may include a process for collecting cells from a donor's blood. Leukapheresis is used to refer to such a process that collects white blood cells from the donor's blood. In some embodiments, the provided embodiments and compositions relate to collection, e.g., via apheresis, of blood samples from a donor; in some embodiments, the methods and compositions relate to administration of compositions, such as cell therapy compositions, to a recipient. In some embodiments, the donor and recipient are the same individual. In some embodiments, cells from a donor are administered to a recipient that is a different subject.

In some embodiments, the methods involve cryogenically storing cells from a donor's blood. In some embodiments, the cryogenically-stored cells are subsequently administered to a recipient to treat a disease. For example, as described in U.S. Patent Application Publication Nos. 2016/0158359 and 2016/0206656 and PCT Publication No. WO 2016/064929 and WO 2016/033570, incorporated herein in their entirely, the cells may be used as part of a cell therapy treatment such as a T cell therapy.

In some embodiments, the donor is the subject, e.g., person, who later receives the collected cells, i.e., the recipient. In such embodiments, the therapy is termed an autologous cell therapy. As discussed herein, advantages of autologous cell therapy can include a reduced chance that the recipient's body would reject the administered cells, since the donor from whom the cells are collected is the recipient. In some embodiments, the donor and the recipient are different people. In such embodiments, the therapy may be termed allogeneic cell therapy. Advantages of allogeneic therapy can include uniformity and consistency across cell samples. Other advantages may include, in some aspects, greater availability of the cells compared to autologous cell therapy, for example, in contexts in which donor cells are available at a time when cells from the recipient may not be, e.g., where the recipient cannot provide such cells and/or is not able to undergo apheresis, such as when the recipient is too ill.

In some embodiments, the cells are collected by apheresis, such as by any of a number of known apheresis techniques. Exemplary apheresis collection methods include drawing blood from a donor using generally accepted practices performed by a medical professional. The medical professional may, for example, select a site on the donor's body, typically an arm, sterilize the site, perform phlebotomy, and draw the blood into a container suitable for preserving the blood, such as a sterile blood bag that contains anticoagulants. For example, the medical professional may perform practices set forth in World Health Organization ("WHO"), *WHO guidelines on drawing blood: best practices in phlebotomy* (2010). The professional may or may not be a professional that diagnoses a disease in the donor, as described below. After the collection of the blood, the components of the blood, such as plasma and different blood cells, may be separated by way of centrifugation.

In some embodiments, the cells are collected after the donor is diagnosed with a disease, and before the donor receives any treatment for the disease and/or before the donor receives a targeted treatment, e.g., a treatment specifically recognizing or binding to an antigen or other ligand associated with the disease or condition. In some embodiments, the cells are collected at a time before the donor has been diagnosed with the disease or condition. Advantages to such embodiments may include improved cell viability, activity, and receptiveness to genetic manipulation, compared to cells that are collected after the donor has received a treatment for the disease. In some embodiments, the cells are collected from the donor after a first relapse of a disease following initial treatment for the disease, and before the donor receives subsequent treatment for the disease. Advantages of such embodiments may include improved cell viability, activity, and receptiveness to genetic manipulation, compared to cells that are collected after the donor has received two or more rounds of treatment for the disease. In other embodiments, the cells are collected from the donor after a second relapse of a disease, and before the donor receives subsequent treatment for the disease.

Among the diseases, conditions, and disorders of the donors and/or recipients, and/or that donors and/or recipients herein have or are suspected of having, and/or targeted by the recombinant receptors, are tumors, including solid tumors, hematologic malignancies, and melanomas, and including localized and metastatic tumors. Also among the diseases, conditions and disorders are infectious diseases, such as infection with a virus or other pathogen, e.g., HIV, HCV, HBV, CMV, HPV, and parasitic disease. Also among the diseases, conditions and disorders are autoimmune and inflammatory diseases. In some embodiments, the disease or condition is a tumor, cancer, malignancy, neoplasm, or other proliferative disease or disorder. Such diseases include but are not limited to leukemia, lymphoma, e.g., chronic lymphocytic leukemia (CLL), small lymphocytic leukemia (SLL), acute lymphoblastic leukemia (ALL), non-Hodgkin's lymphoma, acute myeloid leukemia, multiple myeloma, refractory follicular lymphoma, mantle cell lymphoma, indolent B cell lymphoma, B cell malignancies, cancers of the colon, lung, liver, breast, prostate, ovarian, skin, melanoma, bone, and brain cancer, ovarian cancer, epithelial cancers, renal cell carcinoma, pancreatic adenocarcinoma, Hodgkin's lymphoma, cervical carcinoma, colorectal cancer, glioblastoma, neuroblastoma, Ewing sarcoma, medulloblastoma, osteosarcoma, synovial sarcoma, and/or mesothelioma. In some embodiments the disease or condition is DLBCL, not otherwise specified (NOS; includes transformed DLBCL from follicular lymphoma), high-grade B-cell lymphoma with MYC and BCL2 and/or BCL6 rearrangements with DLBCL histology.

In some embodiments, the subject exhibits CLL with an indication for treatment based on iwCLL guidelines and clinical measurable disease, or SLL that is biopsy-proven SLL. In some aspects, subjects have received and failed Bruton's tyrosine kinase inhibitor (BTKi) treatment or have been deemed ineligible for BTKi therapy.

In some embodiments, subjects with CLL or SLL and high-risk features, for example having complex cytogenetic abnormalities (3 or more chromosomal abnormalities), 17p deletion, TP53 mutation, or unmutated immunoglobulin heavy chain variable region (IGHV), have failed at least 2 lines of prior therapy, including a BTKi. In some embodiments, subjects with CLL or SLL and standard-risk features have failed at least 3 lines of prior therapy, including a BTKi. In some embodiments, subjects with CLL or SLL who are BTKi intolerant and have not received at least 6 months of BTKi therapy or are ineligible for BTKi have failed at least 1 (high-risk) or 2 (standard-risk) lines of non-BTKi therapy.

In some embodiments, the subject is not eligible for one or more clinical trials and/or approved engineered cell immunotherapies. In some embodiments, the subject is not yet eligible for one or more clinical trials and/or approved engineered cell immunotherapies, but is at risk for becoming or may become eligible. In some embodiments, the subject is not eligible for one or more clinical trials and/or approved engineered cell immunotherapies due to anticipated or actual response to one or more previous lines of therapy or after auto-HSCT. In some embodiments, the subject is not eligible for one or more clinical trials and/or approved engineered cell immunotherapies if they have not relapsed and/or are not refractory to one or more lines of previous therapy (for example, two or more, three or more, or four or more lines of previous therapy) or after auto-HSCT. In some embodiments, the subject is not eligible for one or more clinical trials and/or approved engineered cell immunotherapies due to the absence of high-risk cytogenetics.

In some aspects, the subject has a high number of metastases and/or widespread localization of metastases. In some aspects, the tumor burden in the subject is low and the subject has few metastases. In some embodiments, the size or timing of the doses is determined by the initial disease burden in the subject. For example, whereas in some aspects the subject may be administered a relatively low number of cells in the first dose, in context of lower disease burden the dose may be higher.

In some embodiments, the disease or condition is an infectious disease or condition, such as, but not limited to, viral, retroviral, bacterial, and protozoal infections, Cytomegalovirus (CMV), Epstein-Barr virus (EBV), adenovirus, BK polyomavirus, etc.

In some embodiments, the disease or condition is an autoimmune or inflammatory disease or condition, such as arthritis, e.g., rheumatoid arthritis (RA), Type I diabetes, systemic lupus erythematosus (SLE), inflammatory bowel disease, psoriasis, scleroderma, autoimmune thyroid disease, Grave's disease, Crohn's disease, multiple sclerosis, asthma, immunodeficiency, and/or a disease or condition associated with transplant.

In some embodiments, the disease or condition is graft-versus-host disease (GVHD), such as GVHD in a subject who is undergoing or has undergone transplant, such as allogeneic organ transplantation and/or bone marrow and/or hematopoietic stem cell transplantation. The addition of native isolated $CD4^{+}CD25^{+}$ T cells, such as in vitro-expanded Treg cells, can delay and/or prevents graft-versus-host disease in some contexts. In some embodiments, the provided Treg compositions and methods prevent and/or decrease the risk of GVHD or symptom or sign thereof. In some embodiments, the disease or condition is organ transplant rejection, or risk thereof, such as heart, liver, cornea, kidney, lung, pancreas, or other organ transplant.

In some embodiments, the autoimmune or inflammatory disease is a chronic and/or an acute inflammatory disease. In some aspects, the disease or disorder is or includes systemic lupus erythematosus (SLE), rheumatoid arthritis (RA), polymyositis, multiple sclerosis (MS), diabetes, inflammatory bowel disease (IBD), Type I diabetes mellitus or autoimmune insulitis, autoimmune thyroiditis, autoimmune uveitis or uveoretinitis, autoimmune orchitis, autoimmune oophoritis, psoriasis, vitiligo, autoimmune prostatitis, any undesired immune response or other inflammatory or autoimmune disease or condition such as a condition characterized by an unwanted immune response and/or a viro-induced immunopathology. In some aspects, the antigen, e.g., antigen specifically bound by the T cell and/or recombinant receptor is a self or auto-antigen, such as a human antigen expressed on normal or non-diseased tissue. In some aspects, the antigen is not an antigen expressed in cancer or not expressed in cancer in the subject. In some aspects, the subject is not known to have and/or is not suspected of having cancer.

In some embodiments, the antigen recognized by the cell, chimeric antigen receptor (CAR) or T-cell receptor (TCR), or other recombinant receptor is or comprises an autoantigen or antigen that is cross-reactive with an autoantigen, such as a pathogenic antigen in the pathophysiology of an autoimmune disease. In some embodiments, such as where the disease or condition is inflammatory bowel disease (IBD), the antigen is one that is expressed in diseased colon or ileum. In some embodiments, such as in the context of RA, the antigen or ligand is an epitope of collagen or an antigen present in joints. In some embodiments, such as for treatment or prevention of Type I diabetes mellitus or autoimmune insulitis, the antigen is a pancreatic β cell antigen. In some embodiments, such as for MS, the antigen is a myelin basic protein antigen, MOG-1, MOG-2 or another neuronal antigen. In some embodiments, such as where the disease or condition is autoimmune thyroiditis, the antigen or ligand is a thyroid antigen. In some embodiments, such as where the disease or condition is autoimmune gastritis, the antigen is a gastric antigen. In some embodiments, such as for treatment of autoimmune uveitis or uveoretinitis, the antigen is S-antigen or another uveal or retinal antigen. In some embodiments, such as where the disease or condition is orchitis, the antigen is a testicular antigen. In some embodiments, such as in treating or preventing autoimmune oophoritis the antigen is an ovarian antigen. In some embodiments, such as for treatment or prevention of psoriasis; the antigen is a keratinocyte antigen or another dermal or epidermal antigen. In some embodiments, such as for the treatment or prevention of vitiligo, the antigen is a melanocyte antigen. In some embodiments, such as for treating or preventing autoimmune prostatitis, the antigen is a prostate antigen. In some embodiments, the antigen may include an activation antigen expressed on T effector cells present at the site of the undesired immune response.

In some embodiments, the antigen is citrullinated vimentin.

In some embodiments, such as where the disease or condition is or includes tissue or organ rejection, the antigen may include an MHC molecule or portion thereof having a haplotype of the transplanted tissue.

In some embodiments, the antigen associated with the disease or disorder is GPRC5D, glioma-associated antigen, β-human chorionic gonadotropin, alphafetoprotein (AFP), B-cell maturation antigen (BCMA, BCM), B-cell activating factor receptor (BAFFR, BR3), transmembrane activator and CAML interactor (TACI), Fc Receptor-like 5 (FCRL5, FcRH5), orphan tyrosine kinase receptor ROR1, Her2, LI-CAM, CD19, CD20, CD22, mesothelin, CEA, and hepatitis B surface antigen, anti-folate receptor, CD23, CD24, CD30, CD33, CD38, CD44, EGFR, EGP-2, EGP-4, EPHa2, ErbB2, 3, or 4, FBP, fetal acethycholine receptor, GD2, GD3, HMW-MAA, IL-22R-alpha, IL-13R-alpha2, kdr, kappa light chain, Lewis Y, L1-cell adhesion molecule, MAGE-A1, mesothelin, MUC1, MUC16, PSCA, NKG2D Ligands, NY-ESO-1, MART-1, gp100, oncofetal antigen, ROR1, TAG72, VEGF-R2, carcinoembryonic antigen (CEA), prostate specific antigen, PSMA, Her2/neu, estrogen receptor, progesterone receptor, ephrinB2, CD123, CS-1, c-Met, GD-2, and MAGE A3, CE7, Wilms Tumor 1 (WT-1), a cyclin, such as cyclin A1 (CCNA1), and/or biotinylated molecules, and/or molecules expressed by HIV, HCV, HBV or other pathogen.

In some embodiments, the disease is cancer. For example, as described in U.S. Patent Application Publication Nos. 2016/0158359 and 2016/0206656 and PCT Patent Application Publication No. WO 2016/064929, incorporated herein in their entirely, the cells may be used as part of a cancer therapy treatment such as a T cell therapy.

The cancer may be, for example, benign or malignant. The cancer can include, for example, primary cancer or metastatic cancer. In some embodiments, the cancer can be of any stage, such as stage TX, stage T0, stage T1, stage T1a, stage T1b, stage T2, stage T2a, stage T2b, stage T3, stage T3a, stage T3b, stage T4, stage T4a, stage T4b, stage NX, stage N0, stage N1, stage N1a, stage N1b, stage N2, stage N2a, stage N2b, stage N2c, stage N3, stage MX, stage M0, stage M1, stage M1a, stage M1b, stage M1c, stage M2, stage M3, stage M3V, stage M4, stage M4E, stage M5, stage M6, or stage M7.

In some embodiments, the cancer is acute lymphoblastic leukemia, acute myeloid leukemia, adrenocortical carcinoma, Kaposi sarcoma, astrocytoma, basal cell carcinoma, bile duct cancer, bladder cancer, Ewing sarcoma, osteosarcoma, malignant fibrous histiocytoma, brain cancer, breast cancer, bronchial cancer, Burkitt lymphoma, carcinoid cancer, cardiac cancer, atypical teratoid or rhabdoid tumor, embryonal tumor, germ cell tumor, primary central nervous system lymphoma, cervical cancer, cholangiocarcinoma, chronic lymphocytic leukemia, chronic myelogenous leukemia, chronic myeloproliferative neoplasm, colorectal cancer, craniopharyngioma, cutaneous T cell lymphoma, endometrial cancer, ependymoma, esophageal cancer, esthesioneuroblastoma, extracranial germ cell tumor, extragonadal germ cell tumor, intraocular melanoma, retinoblastoma, fallopian tube cancer, gallbladder cancer, gastrointestinal carcinoid tumor, gastrointestinal stromal tumors, glioblastoma, ovarian germ cell tumor, testicular cancer, gestational trophoblastic disease, hairy cell leukemia, head and neck cancer, hepatocellular cancer, Hodgkin's lymphoma, intraocular melanoma, islet cell tumor, pancreatic neuroendocrine tumor, kidney cancer, lung cancer (non-small cell and small cell), malignant fibrous histiocytoma, Merkel cell carcinoma, mesothelioma, midline tract carcinoma, mouth cancer, multiple endocrine neoplasia, mycosis fungoides, myelodysplastic or myeloproliferative neoplasms, chronic myelogenous leukemia, acute myeloid leukemia, chronic myeloproliferative neoplasms, nasopharyngeal cancer, neuroblastoma, non-Hodgkin's lymphoma, ovarian cancer, pancreatic cancer, papillomatosis, paraganglioma, paranasal sinus and nasal cavity cancer, parathyroid cancer, penile cancer, pharyngeal cancer, pheochromocytoma, pituitary tumor, plasma cell neoplasm, multiple myeloma, pleuropulmonary blastoma, peritoneal cancer, prostate cancer, rectal cancer, retinoblastoma, salivary gland cancer, rhabdomyosarcoma, Sezary syndrome, small intestine cancer, small lymphocytic leukemia, squamous cell carcinoma, squamous neck cancer, testicular cancer, throat cancer, nasopharyngeal cancer, oropharyngeal cancer, hypopharyngeal cancer, thymoma, thymic carcinoma, thyroid cancer, urethral cancer, uterine sarcoma, vaginal cancer, vulvar cancer, or Wilms tumor.

In some embodiments, the cancer is chronic lymphocytic leukemia, small lymphocytic leukemia, acute lymphocytic leukemia, pro-lymphocytic leukemia, hairy cell leukemia, acute lymphocytic leukemia, null-acute lymphoblastic leukemia, Hodgkin's lymphoma, non-Hodgkin's lymphoma, diffuse large B cell lymphoma, multiple myeloma, follicular lymphoma, splenic, marginal zone lymphoma, mantle cell lymphoma, indolent B cell lymphoma, or acute myeloid leukemia.

In some embodiments, the cancer comprises cells expressing at least one or more of orphan tyrosine kinase receptor ROR1, EGFR, Her2, L1-CAM, CD19, CD20, CD22, mesothelin, CEA, and hepatitis B surface antigen, anti-folate receptor, CD23, CD24, CD30, CD33, CD38, CD44, EGFR, EGP-2, EGP-4, EPHa2, ErbB2, 3, or 4, FBP, fetal acethycholine receptor, GD2, GD3, HMW-MAA, IL-22R-alpha, IL-13R-alpha2, kdr, kappa light chain, Lewis Y, L1-cell adhesion molecule, MAGE-A1, mesothelin, MUC1, MUC16, B cell maturation antigen (BCMA), FCRL5/FCRH5, GPRC5D, PSCA, NKG2D Ligands, NY-ESO-1, MART-1, gp100, oncofetal antigen, ROR1, TAG72, VEGF-R2, carcinoembryonic antigen (CEA), prostate specific antigen, PSMA, Her2/neu, estrogen receptor, progesterone receptor, ephrinB2, CD123, CS-1, c-Met, GD-2, and MAGE A3, CE7, Wilms Tumor 1 (WT-1), a cyclin, such as cyclin A1 (CCNA1), and/or biotinylated molecules, and/or molecules expressed by HIV, HCV, HBV or other pathogens. In some embodiments, the cancer comprises cells expressing CD19. In some embodiments, the cancer comprises cells expressing BCMA.

In some embodiments, the disease is diagnosed by a medical professional (e.g., a person licensed under a medical regulatory body in a nation, state, province, county, municipality, or township), who examines the donor and confirms the existence of the disease in the donor by observing a disorder of structure or function in the donor. The medical professional may include, for example, a physician, such as a hematologist, an immunologist, an oncologist, or a nurse practitioner.

In some embodiments, the diagnosis excludes self-diagnosis by the donor and/or excludes diagnosis by genetic-testing services.

In some embodiments, the initial treatment and the subsequent treatment can each, independently of each other, include cancer therapy, such as chemotherapy, radiotherapy, immunotherapy, hormonal therapy, and/or surgery. The chemotherapy may include, for example, administering at least one of cyclophosphamide, methotrexate, 5-fluorouracil, doxorubicin, mustine, vincristine, procarbazine, prednisolone, bleomycin, vinblastine, dacarbazine, etoposide, cisplatin, epirubicin, capecitabine, folinic acid, oxaliplatin, and other small-molecule kinase inhibitors. The immunotherapy may include, for example, administering at least one of antibodies and immune cells, such as natural killer cells, lymphokine-activated killer cells, cytotoxic T cells, and dendritic cells. In some embodiments, the treatment (either initial or subsequent) may include any or all of radiation therapy (e.g. 4000 cGy radiation), autologous stem cell rescue, stem cell transplant, bone marrow transplant, and hematopoietic stem cell transplantation (HSCT). In some embodiments the treatment may include CAR T cell therapy. In some embodiments the treatment may include Tisagenlecleucel (Kymriah). In some embodiments the treatment may include Axicabtagene ciloleucel (Yescarta). In some embodiments, the initial and/or subsequent therapy may include any or all of cytarabine (ara-C; including high-dose cytarabine), daunorubicin (daunomycin), idarubicin, or cladribine (Leustatin, 2-CdA), alone or in combination. In some embodiments, the initial and/or subsequent therapy may include any or all of bortezomib, carfilzomib, thalidomide, lenalidomide, pomalidomide, and corticosteroids such as prednisone and dexamethasone. In some embodiments, the initial and/or subsequent therapy may include any or all of alkylating agents such as cyclophosphamide, chlorambucil, bendamustine, and ifosfamide; platinum drugs such as cisplatin, carboplatin, and oxaliplatin; purine analogs such as fludarabine, pentostatin, and cladribine, cytarabine; antimetabolites such as gemcitabine, methotrexate, and pralatrexate; and other agents such as vincristine, doxorubicin, mitoxantrone, etoposide, and bleomycin. In some embodiments, the initial and/or subsequent therapy may include any or all of proteasome inhibitors such as bortezomib; histone deacetylase inhibitors such as romidepsin and belinostat; kinase inhibitors such as ibrutinib and idelalisib. In some embodiments, the initial and/or subsequent therapy may include antibodies that target CD20 such as rituximab, obinutuzumab, ofatumumab, and ibritumomab tiuxetan; antibodies that target CD52, such as alemtuzumab; antibodies that target CD30, such as brentuximab vedotin; interferon; and immunomodulating agents such as thalidomide and lenalidomide. In some embodiments, the initial and/or subsequent therapy may be a combination therapy such as CHOP, CHOP+R (or R-CHOP), CVP. EPOCH, EPOCH+R, DHAP, and DHAP+R (or R-DHAP). CHOP includes the drugs cyclophosphamide, doxorubicin, vincristine and prednisone. R-CHOP (or CHOP+R) further includes treatment with rituximab. CVP includes cyclophosphamide, vincristine and prednisone. CVP may also be administered in combination with rituximab. EPOCH includes the drugs etoposide, prednisone, vincristine, cyclophosphamide, and doxorubicin. EPOCH-R further includes treatment with rituximab. DHAP includes the drugs dexamethasone, high-dose cytarabine, and cisplatin. DHAP+R (or R-DHAP) further includes treatment with rituximab. Additional combination regimens that may be used in accordance with the methods described herein include any one or more of bendamustine plus rituximab (BR); rituximab, cyclophosphamide, etoposide, procarbazine, and prednisone (R-CEPP); rituximab, cyclophosphamide, epirubicin, and prednisone (R-CEOP); rituximab, gemcitabine, cisplatin, and dexamethasone (R-GDP); rituximab and lenalidomide. Additional anti-cancer therapies that may be used in accordance with the methods described herein include any one or more or a combination of chlorambucil, bendamustine, cyclophosphamide, fludarabine, ofatumumab, obinutuzumab, rituximab, idelalisib, venetoclax, lenalidomide, and methylprednisolone.

In some embodiments, the donor may enter a first relapse following initial treatment of the disease and a period of improvement. In some embodiments, the period of improvement is marked by a complete absence of the signs and symptoms of the disease. In some embodiments, during the period of improvement, the signs and symptoms of the disease are alleviated or reduced, but are not completely absent. In some embodiments, the complete absence of the signs and symptoms of the disease, or the alleviation or reduction of the signs and symptoms, are a result of the initial treatment.

In some embodiments, the donor may enter a second relapse following one or more prior treatments of the disease and one or more periods of improvement. In some embodiments, the period(s) of improvement is marked by a complete absence of the signs and symptoms of the disease. In some embodiments, during the period(s) of improvement, the signs and symptoms of the disease are alleviated or reduced, but are not completely absent. In some embodiments, the complete absence of the signs and symptoms of the disease, or the alleviation or reduction of the signs and symptoms, are a result of the prior treatment(s).

In some embodiments, the relapse is diagnosed by a medical professional, who examines the donor and confirms the return of the signs and symptoms of the disease in the donor. In some embodiments, the medical professional is a person licensed under a medical regulatory body in a nation, state, province, county, municipality, or township. The medical professional may include, for example, a physician, such as a hematologist, an immunologist, or an oncologist, or a nurse practitioner. The medical professional diagnosing the disease and the medical professional diagnosing the relapse may or may not be the same person.

In some embodiments, cells from a donor's blood are obtained by apheresis or leukapheresis. In some embodiments, the number of the cells, when collected from the donor, and/or total in the apheresis sample, is at or about or is no more than at or about $500\times10^6$, $1000\times10^6$, $2000\times10^6$, $3000\times10^6$, $4000\times10^6$, or $5000\times10^6$ or more total cells or total nucleated cells. In some embodiments, the sample upon administration to the subject contains at or about from 105 to $10^6$ cells or T cells or engineered cells per each kilogram of the donor's weight and/or from at or about $5\times10^6$ or $10\times10^6$ total cells or T cells or engineered cells or subset thereof. In some embodiments, the volume of the blood, when collected from the donor, is from 0.5 to 5 milliliters for each kilogram of the donor's weight.

In some embodiments, the cells comprise and/or are enriched for the presence of T cells and/or a population thereof. In some embodiments, the cells comprise $CD4^+$ and/or $CD8^+$ T cells, either separately or in combination. Among the sub-types and subpopulations of T cells and/or of $CD4^+$ and/or of $CD8^+$ T cells are naïve T (TN) cells, effector T cells (TEFF), memory T cells and sub-types thereof, such as stem central memory T cells (TSCM), central memory T cells (TCM), effector memory T cells (TEM), or terminally differentiated effector memory T cells, tumor-infiltrating lymphocytes (TIL), immature T cells, mature T cells, helper T cells, cytotoxic T cells, mucosa-associated invariant T (MAIT) cells, naturally occurring and adaptive regulatory T (Treg) cells, helper T cells, such as TH1 cells, TH2 cells, TH3 cells, TH17 cells, TH9 cells, TH22 cells, follicular helper T cells, alpha/beta T cells, and delta/gamma T cells. In some embodiments, the cells are natural killer (NK) cells. In some embodiments, the cells are monocytes or granulocytes, e.g., myeloid cells, macrophages, neutrophils, dendritic cells, mast cells, eosinophils, and/or basophils. In some embodiments, the T cells comprise or are bulk T cells, such as those selected based on CD3 expression, CD4 or CD8 expression, or negativity for non-T cell markers found on blood cells.

In some embodiments, the cell is or comprises a T cell, e.g., a $CD8^+$ T cell (e.g., a $CD8^+$ naïve T cell, central memory T cell, or effector memory T cell), a $CD4^+$ T cell, a natural killer T cell (NKT cells), a regulatory T cell (Treg), a stem cell memory T cell, a lymphoid progenitor cell, a hematopoietic stem cell, a natural killer cell (NK cell), or a dendritic cell. In some embodiments, the cells are monocytes or granulocytes, e.g., myeloid cells, macrophages, neutrophils, dendritic cells, mast cells, eosinophils, and/or basophils. In an embodiment, the cell is an induced pluripotent stem (iPS) cell or a cell derived from an iPS cell, e.g., an iPS cell generated from a subject, manipulated to alter (e.g., induce a mutation in) or manipulate the expression of one or more target genes, and differentiated into, e.g., a T cell, e.g., a $CD8^+$ T cell (e.g., a $CD8^+$ naïve T cell, central memory T cell, or effector memory T cell), a $CD4^+$ T cell, a stem cell memory T cell, a lymphoid progenitor cell, or a hematopoietic stem cell.

In some embodiments, the cells include one or more subsets of T cells or other cell types, such as whole T cell populations, $CD4^+$ cells, $CD8^+$ cells, and subpopulations thereof, such as those defined by function, activation state, maturity, potential for differentiation, expansion, recirculation, localization, and/or persistence capacities, antigen-specificity, type of antigen receptor, presence in a particular organ or compartment, marker or cytokine secretion profile, and/or degree of differentiation.

In some embodiments, among the sub-types and subpopulations of T cells and/or of $CD4^+$ and/or of $CD8^+$ T cells are naïve T (TN) cells, effector T cells (TEFF), memory T cells and sub-types thereof, such as stem cell memory T (TSCM), central memory T (TCM), effector memory T (TEM), or terminally differentiated effector memory T cells, tumor-infiltrating lymphocytes (TIL), immature T cells, mature T cells, helper T cells, cytotoxic T cells, mucosa-associated invariant T (MAIT) cells, naturally occurring and adaptive regulatory T (Treg) cells, helper T cells, such as TH1 cells, TH2 cells, TH3 cells, TH17 cells, TH9 cells, TH22 cells, follicular helper T cells, alpha/beta T cells, and delta/gamma T cells. In some embodiments, the cells are cryogenically frozen and/or cryogenically stored after collection from the donor, without further processing. In some embodiments, the cells are enriched one or more times before being cryogenically frozen and/or stored. In some embodiments, the cells are enriched one or more times after being cryogenically stored. In some instances, not enriching or further processing the cells before cryogenically freezing and/or storing provides the benefit of reducing costs and/or saving time. In some cases, not enriching or further processing the cells before cryogenically freezing and/or storing may also allow for broader collection facility options to donors who do not have access to facilities that are capable of performing cell enrichment and/or processing. Enrichment may be, for example, as described in PCT Application Publication No. WO 2015/164675, incorporated herein in its entirely. In some embodiments, the cells are processed prior to cryogenically freezing and/or storing.

In particular embodiments, the cells are frozen, e.g., following a washing step, e.g., to remove plasma and platelets. In some embodiments, the cells are frozen prior to, subsequent to, and/or during any of the steps associated with manufacturing and/or generating cells, e.g., $CD4^+$ and/or $CD8^+$ T cells, that express a recombinant receptor, e.g., a CAR. In certain embodiments, such steps may include any steps associated with the generation of engineered cells, including but not limited to, selection and/or isolation of a subset of cells, e.g., $CD4^+$ and/or CD8+ T cells, the stimulation and/or expansion of cells, e.g. T cells or a subset thereof, or transfection or transduction of the cells. In some embodiments, the cells are cells of an apheresis sample collected from a subject, prior to the selection and/or isolation of cells, the stimulation and/or expansion of cells, or transfection or transduction of the cells.

Cell Processing Methods

In some embodiments, the cells collected from the subject are washed, e.g., to remove the plasma fraction and to place the cells in an appropriate buffer or media for subsequent processing steps. In some embodiments, the cells are washed with phosphate buffered saline (PBS). In some embodiments, the wash solution lacks calcium and/or magnesium and/or many or all divalent cations. In some aspects, a washing step is accomplished using a semi-automated “flow-through” centrifuge (for example, the Cobe 2991 cell processor, Baxter) according to the manufacturer’s instructions. In some aspects, a washing step is performed in a centrifugal chamber, for example those produced and sold by Biosafe SA, including those for use with the Sepax® and Sepax® 2 system, including an A-200/F and A-200 centrifugal chambers according to the manufacturer’s instructions. In some aspects, a washing step is accomplished by tangential flow filtration (TFF) according to the manufacturer’s instructions. In some embodiments, the cells are resuspended in a variety of biocompatible buffers after washing, such as, for example, $Ca^{++}/Mg^{++}$-free PBS. In certain embodiments, components of a blood cell sample are removed and the cells directly resuspended in culture media.

In some embodiments, the methods include density-based cell separation methods, such as the preparation of white blood cells from peripheral blood by lysing the red blood cells and centrifugation through a Percoll or Ficoll gradient.

In some embodiments, the isolation methods include the separation of different cell types based on the expression or presence in the cell of one or more specific molecules, such as surface markers, e.g., surface proteins, intracellular markers, or nucleic acid. In some embodiments, any known method for separation based on such markers may be used. In some embodiments, the separation is affinity- or immunoaffinity-based separation. For example, the isolation in some aspects includes separation of cells and cell populations based on the cells’ expression or expression level of one or more markers, typically cell surface markers, for example, by incubation with an antibody or binding partner that specifically binds to such markers, followed generally by washing steps and separation of cells having bound the antibody or binding partner, from those cells having not bound to the antibody or binding partner.

Such separation steps can be based on positive selection, in which the cells having bound the reagents are retained for further use, and/or negative selection, in which the cells having not bound to the antibody or binding partner are retained. In some examples, both fractions are retained for further use. In some aspects, negative selection can be particularly useful where no antibody is available that specifically identifies a cell type in a heterogeneous population, such that separation is best carried out based on markers expressed by cells other than the desired population.

The separation need not result in 100% enrichment or removal of a particular cell population or cells expressing a particular marker. In some embodiments, the enriched population contains at least 20%, 30%, 40%, 50%, 60%, 70%, 80%, 90%, or 95% of the population. For example, positive selection of or enrichment for cells of a particular type, such as those expressing a marker, refers to increasing the number or percentage of such cells, but need not result in a complete absence of cells not expressing the marker. Likewise, negative selection, removal, or depletion of cells of a particular type, such as those expressing a marker, refers to decreasing the number or percentage of such cells, but need not result in a complete removal of all such cells.

In some examples, multiple rounds of separation steps are carried out, where the positively or negatively selected fraction from one step is subjected to another separation step, such as a subsequent positive or negative selection. In some examples, a single separation step can deplete cells expressing multiple markers simultaneously, such as by incubating cells with a plurality of antibodies or binding partners, each specific for a marker targeted for negative selection. Likewise, multiple cell types can simultaneously be positively selected by incubating cells with a plurality of antibodies or binding partners expressed on the various cell types.

For example, in some aspects, specific subpopulations of T cells, such as cells positive or expressing high levels of one or more surface markers, e.g., $CD28^+$, $CD62L^+$, $CCR7^+$, $CD27^+$, $CD127^+$, $CD4^+$, $CD8^+$, $CD45RA^+$, and/or $CD45RO^+$ T cells, are isolated by positive or negative selection techniques.

For example, $CD3^+$, $CD28^+$ T cells can be positively selected using CD3/CD28 conjugated magnetic beads (e.g., DYNABEADS® M-450 CD3/CD28 T Cell Expander).

In some embodiments, isolation is carried out by enrichment for a particular cell population by positive selection, or depletion of a particular cell population, by negative selection. In some embodiments, positive or negative selection is accomplished by incubating cells with one or more antibodies or other binding agent that specifically bind to one or more surface markers expressed ($marker^+$) or expressed at a relatively higher level (markerhigh) on the positively or negatively selected cells, respectively.

In some embodiments, T cells are separated from a PBMC sample by negative selection of markers expressed on non-T cells, such as B cells, monocytes, or other white blood cells, such as CD14. In some aspects, a $CD4^+$ or $CD8^+$ selection step is used to separate $CD4^+$ helper and $CD8^+$ cytotoxic T cells. Such $CD4^+$ and $CD8^+$ populations can be further sorted into sub-populations by positive or negative selection for markers expressed or expressed to a relatively higher degree on one or more naive, memory, and/or effector T cell subpopulations.

In some embodiments, $CD8^+$ cells are further enriched for or depleted of naive, central memory, effector memory, and/or stem central memory cells, such as by positive or negative selection based on surface antigens associated with the respective subpopulation. In some embodiments, enrichment for central memory T (TCM) cells is carried out to increase efficacy, such as to improve long-term survival, expansion, and/or engraftment following administration, which in some aspects is particularly robust in such sub-populations. See Terakura et al. (2012) Blood. 1:72-82; Wang et al. (2012) J Immunother. 35(9): 689-701. In some embodiments, combining TCM-enriched $CD8^+$ T cells and $CD4^+$ T cells further enhances efficacy.

In embodiments, memory T cells are present in both $CD62L^+$ and $CD62L^-$ subsets of $CD8^+$ peripheral blood lymphocytes. PBMC can be enriched for or depleted of $CD62L^-CD8^+$ and/or $CD62L^+CD8^+$ fractions, such as using anti-CD8 and anti-CD62L antibodies.

In some embodiments, the enrichment for central memory T (TCM) cells is based on positive or high surface expression of CD45RO, CD62L, CCR7, CD28, CD3, and/or CD127; in some aspects, it is based on negative selection for cells expressing or highly expressing CD45RA and/or granzyme B. In some aspects, isolation of a $CD8^+$ population enriched for TCM cells is carried out by depletion of cells expressing CD4, CD14, CD45RA, and positive selection or enrichment for cells expressing CD62L. In one aspect, enrichment for central memory T (TCM) cells is carried out starting with a negative fraction of cells selected based on CD4 expression, which is subjected to a negative selection based on expression of CD14 and CD45RA, and a positive selection based on CD62L. Such selections in some aspects are carried out simultaneously and in other aspects are carried out sequentially, in either order. In some aspects, the same CD4 expression-based selection step used in preparing the $CD8^+$ cell population or subpopulation, is also used to generate the $CD4^+$ cell population or sub-population, such that both the positive and negative fractions from the CD4-based separation are retained and used in subsequent steps of the methods, optionally following one or more further positive or negative selection steps.

In a particular example, a sample of PBMCs or other white blood cell sample is subjected to selection of $CD4^+$ cells, where both the negative and positive fractions are retained. The negative fraction then is subjected to negative selection based on expression of CD14 and CD45RA or ROR1, and positive selection based on a marker characteristic of central memory T cells, such as CD62L or CCR7, where the positive and negative selections are carried out in either order.

$CD4^+$ T helper cells are sorted into naïve, central memory, and effector cells by identifying cell populations that have cell surface antigens. $CD4^+$ lymphocytes can be obtained by standard methods. In some embodiments, naive $CD4^+$ T lymphocytes are $CD45RO^-$, $CD45RA^+$, $CD62L^+$, $CD4^+$ T cells. In some embodiments, central memory $CD4^+$ cells are $CD62L^+$ and $CD45RO^+$. In some embodiments, effector $CD4^+$ cells are CD62L; and $CD45RO^-$.

In one example, to enrich for $CD4^+$ cells by negative selection, a monoclonal antibody cocktail typically includes antibodies to CD14, CD20, CD11b, CD16, HLA-DR, and CD8. In some embodiments, the antibody or binding partner is bound to a solid support or matrix, such as a magnetic bead or paramagnetic bead, to allow for separation of cells for positive and/or negative selection. For example, in some embodiments, the cells and cell populations are separated or isolated using immunomagnetic (or affinitymagnetic) separation techniques (reviewed in Methods in Molecular Medicine, vol. 58: Metastasis Research Protocols, Vol. 2: Cell Behavior In Vitro and In Vivo, p 17-25 Edited by: S. A. Brooks and U. Schumacher © Humana Press Inc., Totowa, NJ).

In some aspects, two or more selection steps may be performed sequentially. For example, the sample or composition of cells to be separated is subjected to selection of $CD8^+$ cells, where both the negative and positive fractions are retained. The CD8 negative fraction may be further subjected to selection of $CD4^+$ cells. In some aspects, the sample or composition of cells to be separated is subjected to selection of $CD4^+$ cells, where both the negative and positive fractions are retained and the CD4 negative fraction may be subjected to selection of $CD8^+$ cells. Exemplary methods for cell selection are described in PCT Patent Application Publication Numbers WO 2015/157384 and/or WO 2015/164675, which are incorporated by reference in their entirety, all or a portion of which could be used in connection with the methods described herein.

In some aspects, the sample or composition of cells to be separated is incubated with small, magnetizable or magnetically responsive material, such as magnetically responsive particles or microparticles, such as paramagnetic beads (e.g., such as Dynalbeads or MACS beads). The magnetically responsive material, e.g., particle, generally is directly or indirectly attached to a binding partner, e.g., an antibody, that specifically binds to a molecule, e.g., surface marker, present on the cell, cells, or population of cells that it is desired to separate, e.g., that it is desired to negatively or positively select.

In some embodiments, the magnetic particle or bead comprises a magnetically responsive material bound to a specific binding member, such as an antibody or other binding partner. There are many well-known magnetically responsive materials used in magnetic separation methods. Suitable magnetic particles include those described in Molday, U.S. Pat. No. 4,452,773, and in European Patent Specification EP 452342 B, which are hereby incorporated by reference. Colloidal sized particles, such as those described in Owen U.S. Pat. No. 4,795,698, and Liberti et al., U.S. Pat. No. 5,200,084 are other examples, which are hereby incorporated by reference.

The incubation generally is carried out under conditions whereby the antibodies or binding partners, or molecules, such as secondary antibodies or other reagents, which specifically bind to such antibodies or binding partners, which are attached to the magnetic particle or bead, specifically bind to cell surface molecules if present on cells within the sample.

In some aspects, the sample is placed in a magnetic field, and those cells having magnetically responsive or magnetizable particles attached thereto will be attracted to the magnet and separated from the unlabeled cells. For positive selection, cells that are attracted to the magnet are retained; for negative selection, cells that are not attracted (unlabeled cells) are retained. In some aspects, a combination of positive and negative selection is performed during the same selection step, where the positive and negative fractions are retained and further processed or subject to further separation steps.

In certain embodiments, the magnetically responsive particles are coated in primary antibodies or other binding partners, secondary antibodies, lectins, enzymes, or streptavidin. In certain embodiments, the magnetic particles are attached to cells via a coating of primary antibodies specific for one or more markers. In certain embodiments, the cells, rather than the beads, are labeled with a primary antibody or binding partner, and then cell-type specific secondary antibody- or other binding partner (e.g., streptavidin)-coated magnetic particles are added. In certain embodiments, streptavidin-coated magnetic particles are used in conjunction with biotinylated primary or secondary antibodies.

In some embodiments, the magnetically responsive particles are left attached to the cells that are to be subsequently incubated, cultured and/or engineered; in some aspects, the particles are left attached to the cells for administration to a patient. In some embodiments, the magnetizable or magnetically responsive particles are removed from the cells. Methods for removing magnetizable particles from cells are known and include, e.g., the use of competing non-labeled antibodies, magnetizable particles or antibodies conjugated to cleavable linkers, etc. In some embodiments, the magnetizable particles are biodegradable.

In some embodiments, the affinity-based selection is via magnetic-activated cell sorting (MACS) (Miltenyi Biotech, Auburn, CA). Magnetic Activated Cell Sorting (MACS) systems are capable of high-purity selection of cells having magnetized particles attached thereto. In certain embodiments, MACS operates in a mode wherein the non-target and target species are sequentially eluted after the application of the external magnetic field. That is, the cells attached to magnetized particles are held in place while the unattached species are eluted. Then, after this first elution step is completed, the species that were trapped in the magnetic field and were prevented from being eluted are freed in some manner such that they can be eluted and recovered. In certain embodiments, the non-target cells are labelled and depleted from the heterogeneous population of cells.

In certain embodiments, the isolation or separation is carried out using a system, device, or apparatus that carries out one or more of the isolation, cell preparation, separation, processing, incubation, culture, and/or formulation steps of the methods. In some aspects, the system is used to carry out each of these steps in a closed or sterile environment, for example, to minimize error, user handling and/or contamination. In one example, the system is a system as described in PCT Patent Application Publication Number WO 2009/072003, or US Patent Application Publication Number 2011/0003380 A1, which are incorporated herein by reference. In some aspects, the apheresis or leukapheresis product, or a sample derived therefrom, is processed and/or the isolation or selection is carried out using a system, device, apparatus, and/or method as described in PCT Patent Application Publication Number WO 2016/073602 or US Patent Application Publication Number 2016/0122782 the contents of which are incorporated by reference in their entirety. In some embodiments, the isolation or separation is carried out according to methods described in PCT Patent Application Publication Number WO 2015/164675, the contents of which are incorporated by reference in their entirety.

In some embodiments, the system or apparatus carries out one or more, e.g., all, of the isolation, processing, engineering, and formulation steps in an integrated or self-contained system, and/or in an automated or programmable fashion. In some aspects, the system or apparatus includes a computer and/or computer program in communication with the system or apparatus, which allows a user to program, control, assess the outcome of, and/or adjust various aspects of the processing, isolation, engineering, and formulation steps.

In some aspects, the separation and/or other steps is carried out using CliniMACS system (Miltenyi Biotic), for example, for automated separation of cells on a clinical-scale level in a closed and sterile system. Components can include an integrated microcomputer, magnetic separation unit, peristaltic pump, and various pinch valves. The integrated computer in some aspects controls all components of the instrument and directs the system to perform repeated procedures in a standardized sequence. The magnetic separation unit in some aspects includes a movable permanent magnet and a holder for the selection column. The peristaltic pump controls the flow rate throughout the tubing set and, together with the pinch valves, ensures the controlled flow of buffer through the system and continual suspension of cells.

The CliniMACS system in some aspects uses antibody-coupled magnetizable particles that are supplied in a sterile, non-pyrogenic solution. In some embodiments, after labelling of cells with magnetic particles the cells are washed to remove excess particles. A cell preparation bag is then connected to the tubing set, which in turn is connected to a bag containing buffer and a cell collection bag. The tubing set consists of pre-assembled sterile tubing, including a pre-column and a separation column, and are for single use only. After initiation of the separation program, the system automatically applies the cell sample onto the separation column. Labelled cells are retained within the column, while unlabeled cells are removed by a series of washing steps. In some embodiments, the cell populations for use with the methods described herein are unlabeled and are not retained in the column. In some embodiments, the cell populations for use with the methods described herein are labeled and are retained in the column. In some embodiments, the cell populations for use with the methods described herein are eluted from the column after removal of the magnetic field, and are collected within the cell collection bag.

In certain embodiments, separation and/or other steps are carried out using the CliniMACS Prodigy system (Miltenyi Biotec). The CliniMACS Prodigy system in some aspects is equipped with a cell processing unity that permits automated washing and fractionation of cells by centrifugation. The CliniMACS Prodigy system can also include an onboard camera and image recognition software that determines the optimal cell fractionation endpoint by discerning the macroscopic layers of the source cell product. For example, peripheral blood may be automatically separated into erythrocytes, white blood cells, and plasma layers. The CliniMACS Prodigy system can also include an integrated cell cultivation chamber which accomplishes cell culture protocols such as, e.g., cell differentiation and expansion, antigen loading, and long-term cell culture. Input ports can allow for the sterile removal and replenishment of media and cells can be monitored using an integrated microscope. See, e.g., Klebanoff et al. (2012) J Immunother. 35(9): 651-660, Terakura et al. (2012) Blood. 1:72-82, and Wang et al. (2012) J Immunother. 35(9): 689-701.

In some embodiments, a cell population described herein is collected and enriched (or depleted) via flow cytometry, in which cells stained for multiple cell surface markers are carried in a fluidic stream. In some embodiments, a cell population described herein is collected and enriched (or depleted) via preparative scale (FACS)-sorting. In certain embodiments, a cell population described herein is collected and enriched (or depleted) by use of microelectromechanical systems (MEMS) chips in combination with a FACS-based detection system. See, e.g., WO 2010/033140, Cho et al. (2010) Lab Chip 10, 1567-1573; and Godin et al. (2008) J Biophoton. 1(5): 355-376. In both cases, cells can be labeled with multiple markers, allowing for the isolation of well-defined T cell subsets at high purity.

In some embodiments, the antibodies or binding partners are labeled with one or more detectable marker, to facilitate separation for positive and/or negative selection. For example, separation may be based on binding to fluorescently labeled antibodies. In some examples, separation of cells based on binding of antibodies or other binding partners specific for one or more cell surface markers are carried in a fluidic stream, such as by fluorescence-activated cell sorting (FACS), including preparative scale (FACS), and/or microelectromechanical systems (MEMS) chips, e.g., in combination with a flow-cytometric detection system. Such methods allow for positive and negative selection based on multiple markers simultaneously.

In some embodiments, the preparation methods include steps for freezing, e.g., cryopreserving, the cells, either before or after isolation, incubation, and/or engineering. In some embodiments, the freeze and subsequent thaw step removes granulocytes and, to some extent, monocytes in the cell population. In some embodiments, the cells are suspended in a freezing solution, e.g., following a washing step to remove plasma and platelets. Any of a variety of known freezing solutions and parameters in some aspects may be used. One example involves using PBS containing approximately 20% dimethyl sulfoxide (DMSO) and approximately 8% human serum albumin (HSA), or other suitable cell freezing media. In some aspects, the solution is then diluted 1:1 with media so that the final concentration of DMSO and HSA are 10% and 4%, respectively. The cells are then frozen to −80° C. at a rate of 1° per minute and stored in the vapor phase of a liquid nitrogen storage tank.

Any of a variety of known freezing solutions and parameters in some aspects may be used. In some embodiments, a cell sample can contain a cryopreservation or vitrification medium or solution containing the cryoprotectant. Suitable cryoprotectants include, but are not limited to, DMSO, glycerol, a glycol, a propylene glycol, an ethylene glycol, propanediol, polyethylene glycol (PEG), 1,2-propanediol (PROH) or a mixture thereof. In some examples, the cryopreservation solution can contain one or more non-cell permeating cryopreservative, including but not limited to, polyvinyl pyrrolidione, a hydroxyethyl starch, a polysaccharide, a monosaccharide, an alginate, trehalose, raffmose, dextran, human serum albumin, Ficoll, lipoproteins, polyvinyl pyrrolidone, hydroxyethyl starch, autologous plasma or a mixture thereof. In some embodiments, the cells are suspended in a freezing solution with a final concentration of cryoprotectant of between about 1% and about 20%, between about 3% and about 9%, or between about 6% and about 9% by volume. In certain embodiments, the final concentration of cryoprotectant in the freezing solution is about 3%, about 4%, about 5%, about 5.5%, about 6%, about 6.5%, about 7%, about 7.5%, about 8%, about 8.5%, about 9%, about 9.5%, or about 10% by volume.

In particular embodiments, the cells are suspended in a freezing solution with a final concentration of DMSO of between about 1% and about 20%, between about 3% and about 9%, or between about 6% and about 9% by volume. In certain embodiments, the final concentration of DMSO in the freezing solution is about 3%, about 4%, about 5%, about 5.5%, about 6%, about 6.5%, about 7%, about 7.5%, about 8%, about 8.5%, about 9%, about 9.5%, or about 10% by volume.

In some embodiments, the composition is enclosed in one or more bags suitable for cryopreservation (for example, CryoMacs® Freezing Bags, Miltenyi Biotec). In some embodiments, the composition is enclosed in one or more vials suitable for cryopreservation (for example, CellSeal® Vials, Cook Regentec).

In some embodiments, the provided methods include cultivation, incubation, culture, and/or genetic engineering steps either prior or subsequent to a cryopreservation step. In some embodiments, at least the genetic engineering step is performed subsequent to a cryopreservation step. For example, in some embodiments, provided are methods for incubating and/or engineering the cryopreserved cell populations.

Thus, in some embodiments, the cell populations are incubated in a culture-initiating composition. The incubation and/or engineering may be carried out in a culture vessel, such as a unit, chamber, well, column, tube, tubing set, valve, vial, culture dish, bag, or other container for culture or cultivating cells.

In some embodiments, the cells are incubated and/or cultured prior to or in connection with genetic engineering. The incubation steps can include culture, cultivation, stimulation, activation, and/or propagation. In some embodiments, the compositions or cells are incubated in the presence of stimulating conditions or a stimulatory agent. Such conditions include those designed to induce proliferation, expansion, activation, and/or survival of cells in the population, to mimic antigen exposure, and/or to prime the cells for genetic engineering, such as for the introduction of a recombinant antigen receptor.

The conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells. In some aspects, the cells are incubated in the presence of one or more cytokines and in some embodiments a cytokine cocktail can be employed, for example as described in PCT Patent Application Publication Number WO 2015/157384, which is incorporated herein by reference. In some embodiments, the cells are incubated with one or more cytokines and/or a cytokine cocktail prior to, concurrently with, or subsequent to transduction.

In some embodiments, the stimulating conditions or agents include one or more agent, e.g., ligand, which is capable of activating an intracellular signaling domain of a TCR complex. In some aspects, the agent turns on or initiates TCR/CD3 intracellular signaling cascade in a T cell. Such agents can include antibodies, such as those specific for a TCR, e.g. anti-CD3. In some embodiments, the stimulating conditions include one or more agent, e.g. ligand, which is capable of stimulating a costimulatory receptor, e.g., anti-CD28. In some embodiments, such agents and/or ligands may be bound to solid support, such as a bead, and/or one or more cytokines. Optionally, the expansion method may further comprise the step of adding anti-CD3 and/or anti CD28 antibody to the culture medium (e.g., at a concentration of at least about 0.5 ng/ml). In some embodiments, the stimulating agents include IL-2, IL-15 and/or IL-7. In some aspects, the IL-2 concentration is at least about 10 units/mL.

In some aspects, incubation is carried out in accordance with techniques such as those described in U.S. Pat. No. 6,040,177 to Riddell et al., Klebanoff et al. (2012) J Immunother. 35(9): 651-660, Terakura et al. (2012) Blood. 1:72-82, and/or Wang et al. (2012) J Immunother. 35(9): 689-701. In some aspects, incubation is carried out using a system, device, apparatus, and/or method as described in PCT Patent Application Publication Number WO 2016/073602 or US 2016/0122782 the contents of which are incorporated by reference in their entirety. In some embodiments, the incubation and/or culturing is carried out according to methods described in PCT Patent Application Publication Number WO 2015/164675, the contents of which are incorporated by reference in their entirety.

In some embodiments, the T cells are expanded by adding to the culture-initiating composition feeder cells, such as non-dividing peripheral blood mononuclear cells (PBMC), (e.g., such that the resulting population of cells contains at least about 5, 10, 20, or 40 or more PBMC feeder cells for each T lymphocyte in the initial population to be expanded); and incubating the culture (e.g. for a time sufficient to expand the numbers of T cells). In some aspects, the non-dividing feeder cells can comprise gamma-irradiated PBMC feeder cells. In some embodiments, the PBMC are irradiated with gamma rays in the range of about 3000 to 3600 rads to prevent cell division. In some aspects, the feeder cells are added to culture medium prior to the addition of the populations of T cells.

In some embodiments, the stimulating conditions include temperature suitable for the growth of human T lymphocytes, for example, at least about 25 degrees Celsius, generally at least about 30 degrees, and generally at or about 37 degrees Celsius. Optionally, the incubation may further comprise adding non-dividing EBV-transformed lymphoblastoid cells (LCL) as feeder cells. LCL can be irradiated with gamma rays in the range of about 6000 to 10,000 rads. The LCL feeder cells in some aspects is provided in any suitable amount, such as a ratio of LCL feeder cells to initial T lymphocytes of at least about 10:1.

In embodiments, antigen-specific T cells, such as antigen-specific $CD4^+$ and/or $CD8^+$ T cells, are obtained by stimulating naive or antigen specific T lymphocytes with antigen. For example, antigen-specific T cell lines or clones can be generated to cytomegalovirus antigens by isolating T cells from infected subjects and stimulating the cells in vitro with the same antigen.

In some embodiments, the cells are enriched before being cryogenically frozen and/or stored. Advantages of enriching cells before cryogenically freezing and/or storing them may include saving time. For example, when a recipient needs the cells as part of a cell replacement therapy, the cells may be thawed from cryogenic storage and administered to the recipient without further manipulations. In some embodiments, the methods include enrichment of a type or types of cells. In some embodiments, the enriched cells are T cells. In some embodiments, $CD4^+$ T cells are enriched. In some embodiments, $CD8^+$ T cells are enriched. In some embodiments, both $CD4^+$ and $CD8^+$ T cells are enriched. In some embodiments, the $CD4^+$ and $CD8^+$ T cells are enriched in separate processes. In some embodiments, the $CD4^+$ and $CD8^+$ T cells are enriched in a single process. Enrichment of $CD4^+$ and/or $CD8^+$ T cells may be, for example, as described in PCT Application Publication No. WO 2015/164675, incorporated herein in its entirely.

In some embodiments, the cells are analyzed before being cryogenically stored. In some embodiments, the cells may be analyzed to measure an activity of the cells. In some embodiments, the activity is a biological function of the cells. In some embodiments, the activity is the cells' ability to assist in an immunologic process, including maturation of B cells into plasma cells and/or memory B cells, activation of cytotoxic T cells and/or macrophages, etc. In some embodiments, the activity is the cells' ability to bind to specific ligands or antigens using receptors, receptor-like molecules, antibodies, or antibody-like molecules. In some embodiments, the activity is the cells' ability to recognize and destroy virus-infected cells and tumor cells. In some embodiments, the cells are analyzed to measure another biological function of the cells that is related to or affects the activity of the cells.

Cell selection and/or processing steps may also be, for example, as described in WO2017214207, the contents of which are hereby incorporated by reference in their entirety, and/or WO2016073602, the contents of which are hereby incorporated by reference in their entirety.

Cryogenic Freezing Methods

In some embodiments, the cells, e.g., are frozen at a particular cell density, e.g., a known or controlled cell density. In certain embodiments, the cell density during the freezing process may affect cell death and/or cell damage that occurs during and/or due to the freezing process.

For example, in particular embodiments, cell density affects equilibrium, e.g., osmotic equilibrium with surroundings during the freezing process. In some embodiments, this equilibrium is, includes, and/or results in dehydration. In certain embodiments, the dehydration is or includes cellular dehydration that occurs with contact, combination, and/or incubation with a freezing solution, e.g., DMSO and/or a DMSO containing solution. In particular embodiments, the dehydration is or includes dehydration resulting from the nucleation and enlargement of ice crystals in extracellular space, such as by reducing the effective liquid water concentration exposed to the cells. In some embodiments, the cells are frozen at a cell density that results in slower and/or less rapid dehydration than cells that are frozen at a different, e.g., higher or lower, cell density. In some embodiments, the cells are frozen at a cell density that results in about, at least, or at 5%, 10%, 20%, 25%, 30%, 40%, 50%, 60%, 70%, 80%, 90%, 100%, 125%, 150%, 175%, 200%, 1-fold, 2-fold, 3-fold, 4-fold, 5-fold, 10-fold, 50-fold, or 100-fold slower dehydration that cells frozen at a different cell density, e.g., higher or lower, under the same or similar conditions.

In certain embodiments, the cells are suspended in a freezing solution at a density of between or between about $1\times10^6$ cells/mL and about $1\times10^8$ cells/mL, between about $1\times10^6$ cells/mL and about $2\times10^7$ cells/mL, between about $1\times10^7$ cells/mL and about $5\times10^7$ cells/mL, or between about $1\times10^7$ cells/mL and $5\times10^7$ cells/mL, each inclusive. In certain embodiments, the cells are suspended in the freezing solution at a density of about $1\times10^6$ cells/mL, about $2\times10^6$ cells/mL, about $5\times10^6$ cells/mL, about $1\times10^7$ cells/mL, about $1.5\times10^7$ cells/mL, about $2\times10^7$ cells/mL, about $2.5\times10^7$ cells/mL, about $2.5\times10^7$ cells/mL, about $2.5\times10^7$ cells/mL, about $3\times10^7$ cells/mL, about $3.5\times10^7$ cells/mL, about $4\times10^7$ cells/mL, about $4.5\times10^7$ cells/mL, or about $5\times10^7$ cells/mL, each inclusive. In certain embodiments, the cells are suspended in the freezing solution at a density of between about $1.5\times10^7$ cells/mL and about $6\times10^7$ cells/mL, inclusive. In certain embodiments, the cells are suspended in a freezing solution at a density of at least about $1\times10^7$ cells/mL. In certain embodiments, the cells are suspended in a freezing solution at a density of between about $5\times10^6$ cells/mL and about $150\times10^6$ cells/mL, inclusive. In particular embodiments, the cells are suspended in a freezing solution at a density of at least about $1.5\times10^7$ cells/mL. In some embodiments, the cells are viable cells. In some embodiments, cell density is determined by T-cell diameter.

In some embodiments, the cells are frozen in one or more containers. In certain embodiments, the container is a freezing container and/or a cryoprotectant container. Containers suitable for cryofreezing include, but are not limited to vials, bags, e.g., plastic bags, and canes. In particular embodiments, cells, e.g., cells of the same cell composition such as a cell composition containing CAR expressing cells, are frozen in 1, 2, 3, 4, 5, 6, 7, 8, 9 10, or more than 10 separate containers. For example, in some embodiments, the cells and/or a composition of cells are suspended in a volume, e.g., such as in a solution, a freezing solution, and/or a cryoprotectant, and that is larger than a volume suitable for a container, and so the volume is placed in two or more containers. In some embodiments, the volume is, is about, or is less than 100 mL, 50 mL, 25 mL, 20 mL, 15 mL, 10 mL, 5 mL, or less than 5 mL, and the cells are frozen in two, three, four, five six, seven, eight, nine, ten, or more than ten separate vials. In particular embodiments, the same volume of cells is placed into each vial. In some embodiments, the vials are identical vials, e.g., vials of the same make, model, and/or manufacturing lot. In particular embodiments, the volume is, is about, or greater than 10 mL, 15 mL, 20 mL, 25 mL, 30 mL, 40 mL, 50 mL, 60 mL, 70 mL, 80 mL, 90 mL, 100 mL, 120 mL, 150 mL, 200 mL, or more than 200 mL and the cells are frozen in two, three, four, five six, seven, eight, nine, ten, or more than ten separate bags. In particular embodiments, the same volume of cells is placed into each bag. In some embodiments, the bags are identical bags, e.g., bags of the same make, model, and/or manufacturing lot.

In some embodiments, the container is a vial. In certain embodiments, the container is a vial with a fill volume of, of about, or of at least 0.5 mL, 1 mL, 2 mL, 3 mL, 4 mL, 5 mL, 6 mL, 7 mL, 8 mL, 9 mL, 10 mL, 11 mL, 12 mL, 13 mL, 14 mL, 15 mL, 16 mL, 17 mL, 18 mL, 19 mL, 20 mL, 25 mL, 30 mL, 35 mL, 40 mL, 45 mL, or 50 mL. In some embodiments, the vial has a fill volume of between 1 mL and 120 mL, 1 mL and 20 mL, 1 mL and 5 mL, 1 mL and 10 mL, 1 mL and 40 mL, or 20 mL and 40 mL, each inclusive. In some embodiments, the vial is a freezing vial, cryoprotectant vial, and/or a cryovial. Suitable vials are known and include but are not limited to CellSeal® Vials (Cook Regentec), and vials described in U.S. Patent Nos: U.S. Pat. Nos. 8,936,905, 9,565,854 and 8,709,797, hereby incorporated by reference in their entirety.

In particular embodiments, the container is a bag. In certain embodiments, the container is a bag with a fill volume of, of about, or of at least 0.5 mL, 1 mL, 2 mL, 3 mL, 4 mL, 5 mL, 6 mL, 7 mL, 8 mL, 9 mL, 10 mL, 11 mL, 12 mL, 13 mL, 14 mL, 15 mL, 16 mL, 17 mL, 18 mL, 19 mL, 20 mL, 25 mL, 30 mL, 35 mL, 40 mL, 45 mL, or 50 mL. In some embodiments, the bag has a fill volume of between 1 mL and 120 mL, 1 mL and 20 mL, 1 mL and 5 mL, 1 mL and 40 mL, 20 mL and 40 mL, 1 mL and 70 mL, or 50 mL and 70 mL, each inclusive. In some embodiments, the bag is filled with a volume of, of about, or less than 100 mL, 75 mL, 70 mL, 50 mL, 25 mL, 20 mL, or 10 mL. Suitable bags are known, and include but are not limited to CryoMacs® Freezing Bags (Miltenyi Biotec). In certain embodiments, the volume is the volume at room temperature. In some embodiments, the volume is the volume between 37° C. and 4° C., 16° C. and 27° C., inclusive, or at, at about, or at least 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., or 37° C. In some embodiments, the volume is the volume at 25° C.

In some embodiments, cells in a volume of media or solution, e.g., freezing solution, of between 1 mL and 20 mL are frozen in one or more vials, inclusive. In some embodiments, the one or more vials have a fill volume of between 1 mL and 5 mL, inclusive. In certain embodiments, cells in a volume of media or solution, e.g., freezing solution, of between 20 mL and 120 mL, inclusive, are frozen in one or more bags. In particular embodiments, the one or more bags have a fill volume of between 20 mL and 40 mL, inclusive. In some embodiments, cells in a volume of media or solution, e.g., freezing solution, of 120 mL or greater are frozen in one or more bags. In certain embodiments, the one or more bags have a fill volume of between 50 mL and 70 mL, inclusive.

In certain embodiments, the cells are frozen in solution, e.g., freezing solution, that is placed in a container, e.g., a bag or a vial, at a surface area to volume ratio. In particular embodiments, the surface area to volume ratio is from or from about 0.1 $cm^{-1}$ to 100 $cm^{-1}$; 1 $cm^{-1}$ to 50 $cm^{-1}$, 1 $cm^{-1}$ to 20 $cm^{-1}$, 1 $cm^{-1}$ to 10 $cm^{-1}$, 2 $cm^{-1}$ to 10 $cm^{-1}$, 3 $cm^{-1}$ to 7 $cm^{-1}$, or 3 $cm^{-1}$ to 6 $cm^{-1}$, each inclusive. In particular embodiments, the surface area to volume ratio is between or between about 3 $cm^{-1}$ to 6 $cm^{-1}$. In some embodiments, the surface area to volume ratio is, is about, or is at least 3 $cm^{-1}$, 4 $cm^{-1}$, 5 $cm^{-1}$, 6 $cm^{-1}$, or 7 $cm^{-1}$.

In some embodiments, the cells are frozen to −80° C. at a rate of at or at about 1° C. per minute. In some embodiments, the cells are actively and/or effectively cooled at a rate of or of about 1° C. per minute using a controlled rate freezer. In some embodiments, cells can be frozen with a controlled rate freezer. In some aspects, the controlled rate freezers are used to freeze cells with programmed cooling profiles, e.g. profiles with multiple cooling and/or heating rates. Such freezing profiles may be programmed to control nucleation, e.g., ice formation, for example to reduce intracellular ice formation. In some embodiments, the temperature selected to start a rapid cooling profile and the ending temperature are related to the types of containers and volumes being frozen. In some embodiments, if volumes are too small or vessels have surface area to volume ratios that are too high, samples will respond too quickly to the temperature dip, freeze too rapidly, and are at risk for intracellular ice formation. In other embodiments, if volumes are too large or vessel diameters have surface area to volume ratios that are too low, samples will not respond to the temperature dip, freezing will occur too slowly, and samples are at risk for uncontrolled nucleation later in the profile and solution effects injury from prolonged exposure to cryopreservation agents, e.g. DMSO, before ice crystal formation.

In some embodiments, the cells are frozen using the following profile: a hold step at 4.0° C. followed by a cooling step of 1.2° C. per minute until the sample reaches a temperature of −6° C. In some aspects, the sample is then cooled at a rate of 25° C. per minute until the chamber containing the sample reaches −65° C. In some aspects, the sample is then heated at a rate of 15° C. per minute until the chamber containing the sample reaches −30° C. In some aspects, the sample is then cooled at a rate of 1° C. per minute until the chamber containing the sample reaches −40° C. In some aspects, the sample is then cooled at a rate of 1° C. per minute until the chamber containing the sample reaches −90° C. In some aspects, sample is then held at −90° C. until removal from the controlled rate freezer.

In some embodiments, the cells are frozen using the following profile: a hold step at 4.0° C. followed by a cooling step of 1.2° C. per minute until the sample reaches a temperature of −6° C. In some aspects, the sample is then cooled at a rate of 25° C. per minute until the chamber containing the sample reaches −65° C. In some aspects, the sample is then heated at a rate of 15° C. per minute until the chamber containing the sample reaches −30° C. In some aspects, the sample is then cooled at a rate of 1° C. per minute until the chamber containing the sample reaches −40° C. In some aspects, the sample is then cooled at a rate of 10° C. per minute until the chamber containing the sample reaches −90° C. In some aspects, a sample is then held at −90° C. until removal from the controlled rate freezer.

In some embodiments, the cells are cooled to a temperature from above −80° C. to 0° C. before being cryogenically frozen and/or stored. For example, the cells may be cooled to −20° C., or to a temperature above −80° C. or below −20° C.

In some embodiments, the cells are cryogenically frozen to a temperature from −210° C. to −80° C. before being cryogenically stored. For example, the cells may be cryogenically frozen to −210° C., or −196° C., or −80° C.

In some embodiments, the cells are cooled and/or cryogenically frozen at a rate of 0.1° C. to 5° C. per minute. In some embodiments, the cells are cooled and/or cryogenically frozen at a rate of 0.2° C. to 4° C. per minute. In some embodiments, the cells are cooled and/or cryogenically frozen at a rate of 0.5° C. to 3° C. per minute. In some embodiments, the cells are cooled and/or cryogenically frozen at a rate of 0.5° C. to 2° C. per minute. In some embodiments, the cells are cooled and/or cryogenically frozen at a rate of 1° C. per minute. For example, a way of cooling and/or cryogenically freezing the cells at the above rates includes placing the cells in a programmable refrigerator that lowers its temperature therein at such rates. Another way of doing so includes placing a vial of cells in a container, in which the vial is surrounded by isopropyl alcohol, and placing the container in a cooled or cryogenically frozen environment. In some embodiments, the cells are stored at a temperature lower than that to which they are frozen using the stepwise approach. For example, in some embodiments, storage is at a temperature below-80° C., such as below −100, −110, −120, −130, −140, −150, −160° C., or lower. In some aspects, such storage provides for maintaining of the cells or biological activity thereof to a greater degree and/or for a longer period of time.

In some embodiments, before the cooling or cryogenic freezing, the cells are washed to remove certain components in the sample in which the cells exist. For instance, the cells may be washed to remove plasma and/or platelets. The cells may be washed, for example, as described in PCT Application Publication No. WO 2015/164675, incorporated herein by reference in its entirely.

In some embodiments, the cells are combined with a freezing solution before cooling, cryogenically freezing, and/or cryogenically storing. In some embodiments, the freezing solution leads to greater retention of one or more biological functions of the cells after the cooling, the cryogenically freezing, or the cryogenic storage, and after thawing the cells, compared to cells cooled, cryogenically frozen, or cryogenically stored without a freezing solution.

In some embodiments, the freezing solution includes from 0.1% to 50% DMSO by volume, and from 0.1% to 20% HSA by weight. In some embodiments, the freezing solution includes from 0.5% to 40% DMSO by volume, and from 0.2% to 15% HSA by weight. In some embodiments, the freezing solution includes from 1% to 30% DMSO by volume, and from 0.5% to 10% HSA by weight. In some embodiments, the freezing solution includes from 1% to 20% DMSO by volume, and from 2% to 7.5% HSA by weight. In some embodiments, the freezing solution includes from 5% to 20% DMSO by volume, and from 1% to 5% HSA by weight. In some embodiments, the freezing solution includes 10% DMSO by volume or at or about 7 or 7.5 or 8% DMSO by volume, and 4% HSA by weight. In some embodiments, the above concentrations are concentrations of DMSO and HSA before the freezing solution is combined with the cells. In some embodiments, the above concentrations are concentrations of DMSO and HSA after the freezing solution is combined with the cells.

In some embodiments, the cells are cryogenically stored at a temperature from −210° C. to −80° C. In some embodiments, the cells are cryogenically stored at a temperature from −210° C. to −196° C. In some embodiments, the cells are cryogenically stored at a temperature from −196° C. to −80° C. In some embodiments, the cells are cryogenically stored in the vapor phase of a liquid nitrogen storage tank.

In some embodiments, the cells are cryogenically stored for a period of from 1 day to 12 years. For example, the cells can be stored for a period before which they lose viability for use in cell therapy and until needed for treatment of the recipient. By having cells so-stored until needed for treatment of the recipient, in certain embodiments the disclosed methods provide an advantage of having the cells readily available when the recipient needs them for cell therapy. In some embodiments, the cells are stored, or banked, for a period of time greater than or equal to 12 hours, 24 hours, 36 hours, or 48 hours. In some embodiments, the cells are stored or banked for a period of time greater than or equal to 1 week, 2 weeks, 3 weeks, or 4 weeks. In some embodiments, the cells are placed into "long-term storage" or "long-term banking." In some aspects, the cells are stored for a period of time greater than or equal to 1 month, 2 months, 3 months, 4 months, 5 months, 6 months, 7 months, 8 months, 9 months, 10 months, 11 months, 1 year, 2 years, 3 years, 4 years, 5 years, 6 years, 7 years, 8 years, 9 years, 10 years, 11 years, 12 years, 13 years, 14 years, 15 years, 16 years, 17 years, 18 years, 19 years, 20 years, 25 years, 30 years, 35 years, 40 years, or more.

In some embodiments, after the storage period, the cells are thawed. In some embodiments, the cells are thawed by raising the temperature of the cells to at or above 0° C., so as to restore at least a portion of a biological function of the cells. In some embodiments, the cells are thawed by raising the temperature of the cells to 37° C., so as to restore at least a portion of a biological function of the cells. According to certain embodiments, thawing involves placing the cells, in a container, in a 37° C. water bath for 60 to 90 seconds.

In some embodiments, the cells are thawed. In particular embodiments, the cells are thawed rapidly, e.g., as rapidly as possible without overheating the cells or exposing the cells to high temperatures such as above 37° C. In some embodiments, rapid thawing reduces and/or prevents exposure of the cells to high concentrations of cryoprotectant and/or DMSO. In particular embodiments, the rate at which thawing occurs may be affected by properties of the container, e.g., the vial and/or the bag, that the cells are frozen and thawed in.

In particular embodiments, the cells are thawed at a temperature of, of about, or less than 37° C., 35° C., 32° C., 30° C., 29° C., 28° C., 27° C., 26° C., 25° C., 24° C., 23° C., 22° C., 21° C., 20° C., or 15° C., or between 15° C. and 30° C., between 23° C. and 28° C., or between 24° C. and 26° C., each inclusive.

In some embodiments, the cells are thawed on a heat block, in a dry thawer, or in a water bath. In certain embodiments, the cells are not thawed on a heat block, in a dry thawer, or water bath. In some embodiments, the cells are thawed at room temperature.

In some embodiments, the thickness of the container walls affects the rate of cell thawing, such as for example cells in containers with thick walls may thaw at a slower rate than in containers with thinner walls. In some embodiments, containers having a low ratio of surface area to volume may have a slow and/or uneven rate of thawing. In some embodiments, cryofrozen cells are rapidly thawed in a container having a surface area to volume ratio is, is about, or is at least 1 $cm^{-1}$, 2 $cm^{-1}$, 3 $cm^{-1}$, 4 $cm^{-1}$, 5 $cm^{-1}$, 6 $cm^{-1}$, or 7 $cm^{-1}$, 8 $cm^{-1}$, 9 $cm^{-1}$, or 10 $cm^{-1}$. In particular embodiments, the cells are thawed in, in about, or in less than 120 minutes, 90 minutes, 60 minutes, 45 minutes, 30 minutes, 25 minutes, 20 minutes, 15 minutes, or ten minutes. In some embodiments, the cells are thawed for between 10 minutes and 60 minutes, 15 minutes and 45 minutes, or 15 minutes and 25 minutes, each inclusive. In particular embodiments, the cells are thawed in, in about, or in less than 20 minutes.

In certain embodiments, the thawed cells are rested, e.g., incubated or cultured, prior to administration or prior to any subsequent engineering and/or processing steps. In some embodiments, the cells are rested in low and/or undetectable amounts of cryoprotectant, or in the absence of cryoprotectant, e.g., DMSO. In particular embodiments, the thawed cells are rested after or immediately after washing steps, e.g., to remove cryoprotectant and/or DMSO. In some embodiments, the resting is or includes culture and/or incubation at or at about 37° C. In some embodiments, the resting is performed in the absence of any reagents, e.g., stimulatory reagents, bead reagents, or recombinant cytokines, used with and/or associated with any processing or engineering step. In some embodiments, the cells are rested for, for about, or for at least 5 minutes, 10 minutes, 15 minutes, 30 minutes, 1 hour, 2 hours, 3 hours, 4 hours, 5 hours, 6 hours, 8 hours, 12 hours, 18 hours, or 24 hours. In certain embodiments, the cells are rested for, for about, or for at least 2 hours.

In some embodiments, after the storage period, the percentage of viable cells is from 24% to 100%. The percentage of viable cells may be determined, for example, by using the trypan blue dye exclusion technique, for example, as described in Schulz et al., *Towards a xeno-free and fully chemically defined cryopreservation medium for maintaining viability, recovery, and antigen-specific functionality of PBMC during long-term storage,* 382 J. Immu. Methods 24, 26, which discloses performing trypan blue exclusion using the ViCell™ cell viability analyzer (Beckman Coulter, Krefeld, Germany). Under the trypan blue dye exclusion technique, for example, dead cells appear blue and are therefore distinguishable from viable cells. The percentage of viable cells may also be determined, for example, by using a flow cytometer or another technique or instrument.

During the process of cooling, cryogenically freezing, and/or cryogenically storing the sample or the cells, one or more biological functions of the cells are preserved. The use of a freezing solution assists in preserving these biological functions. When the cells are thawed, these biological functions are restored. In addition to viability, a biological function described above, other biological functions may include the cells' ability to replicate, receptiveness to genetic modification, and ability to assist in immunologic processes, including maturation of B cells into plasma cells and/or memory B cells, and activation of cytotoxic T cells and/or macrophages, etc.

In some embodiments, features of the frozen cells including any of the cells and compositions as described, such as cell compositions at a particular concentration or cell density, frozen in the presence of a cryoprotectant and/or filled into a container at a particular volume or surface to volume ratio, include improved, increased, and/or faster expansion; improved increased, and/or enhanced cell survival and reduced instances of cell death, e.g., necrosis, programmed cell death, and/or apoptosis; improved, enhanced, and/or increased activity, e.g., cytolytic activity; and/or reduced instance of senescence or quiescence after thawing than cells frozen by alternate means.

In particular embodiments, the cells are frozen at a cell density and/or a surface area to volume ratio provided herein and have reduced cell death, e.g., necrosis and/or apoptosis, during and/or resulting from the freezing, cryofreezing, and/or cryopreservation, as compared to cells frozen at a different cell density and/or a different surface area to volume ratio under the same or similar conditions. In particular embodiments, the cells are frozen at a cell density and/or a surface area to volume ratio provided herein and have reduced delayed cell death, e.g., a reduction in the amount of cells that die, e.g., via necrosis, programmed cell death, or apoptosis, within 48 hours after freezing, cryofreezing, and/or cryopreservation, e.g. after the thawing of the frozen cells. In certain embodiments, at least or about 5%, 10%, 20%, 25%, 30%, 40%, 50%, 60%, 70%, 80%, 90%, or 99% less cells die during and/or resulting from freezing and/or cryopreservation as compared to cells that are frozen at a different cell density and/or a different surface area to volume ratio under the same or similar conditions. In certain embodiments, less than 40%, 30%, 25%, 20%, 15%, 10%, 5%, 1%, 0.1%, or 0.01% of the cells frozen at the provided cell density and/or a surface area to volume ratio die during or as a result from freezing, cryofreezing, and/or cryopreservation.

In some embodiments, the cells are frozen at a cell density and/or a surface area to volume ratio provided herein and have reduced instances of senescence or quiescence due to and/or resulting from the freezing, cryofreezing, and/or cryopreservation, as compared to cells frozen at a different cell density and/or a different surface area to volume ratio under the same or similar conditions. In particular embodiments, at least or about 5%, 10%, 20%, 25%, 30%, 40%, 50%, 60%, 70%, 80%, 90%, or 99% less cells are senescent and/or quiescent cells as compared to cells frozen at a different cell density and/or a different surface area to volume ratio under the same or similar conditions. In certain embodiments, the cells are frozen at the provided cell density and/or surface area to volume ratio and less than 40%, 30%, 25%, 20%, 15%, 10%, 5%, 1%, 0.1%, or 0.01% of the cells become senescent and/or quiescent as a result from freezing, cryofreezing, and/or cryopreservation.

In certain embodiments, the cells are frozen, e.g., cryofrozen, at a cell density and/or surface area to volume ratio provided herein and have improved, faster, and/or more rapid expansion, e.g., under stimulatory conditions such as by incubation with a stimulatory reagent described herein, after the cells are thawed, as compared to cells frozen at a different cell density and/or surface area to volume ratio under the same or similar conditions. In particular embodiments, the cells expand at a rate that is faster and/or more rapid by, by about, or by at least 5%, 10%, 20%, 25%, 30%, 40%, 50%, 60%, 70%, 80%, 90%, 100%, 150%, 200%, 1-fold, 1.5 fold, 2-fold, 3-fold, 4-fold, 5-fold, or 10-fold as compared to cells frozen at a different cell density and/or a different surface area to volume ratio under the same or similar conditions. For example, in some embodiments, the thawed cells reach a threshold expansion, e.g., a predetermined cell number, density, or factor such as a 2-fold expansion, in, in about, or in at least 5% 10%, 20%, 25%, 30%, 40%, 50%, 60%, 70%, 80%, 90%, 95%, or 99%, less time than thawed cells that were frozen at a different cell density and/or a different surface area to volume ratio under the same or similar conditions.

In some embodiments, the cells are frozen, e.g., cryofrozen, at the cell density and have improved, increased, and/or more cytolytic activity, e.g., such as measured by any assay for measuring cytolytic activity described herein, after the cells are thawed, as compared to cells frozen at a different cell density, e.g., a higher or lower density, under the same or similar conditions. In particular embodiments, the cytolytic activity is increased by, by about, or by at least 5%, 10%, 20%, 25%, 30%, 40%, 50%, 60%, 70%, 80%, 90%, 100%, 150%, 200%, 1-fold, 1.5 fold, 2-fold, 3-fold, 4-fold, 5-fold, or 10-fold as compared to cells frozen at a different density under the same or similar conditions.

Cell Modifications

In some embodiments, the cells may be modified to, for example, confer upon the cells one or more of a new, enhanced, altered, increased, or decreased activity. In some embodiments, the cells are modified after collection and before cryogenic freezing and/or storage. In some embodiments, the cells are modified after thawing following cryogenic storage. Exemplary cell modification methods are described in PCT Application Publication Nos. WO 2016/033570 and WO 2016/115559, incorporated herein by reference in their entirely. Exemplary cell modification methods are also described in WO2017214207, and/or WO2016073602, the contents of which are hereby incorporated by reference in their entirety.

In some embodiments, the activity is a biological function of the cells, such as, for example, the cells' ability to assist in immunologic processes, including maturation of B cells into plasma cells and/or memory B cells, and activation of cytotoxic T cells and/or macrophages, etc. In some embodiments, the activity is the cells' ability to bind to specific ligands or antigens using receptors, receptor-like molecules, antibodies, or antibody-like molecules. In some embodiments, the activity is the cells' ability to recognize and destroy virus-infected cells and tumor cells.

Genetic Modification of Cells

In some embodiments, the cell modification includes genetically modifying the cells. For example, the genetic modification may be as described in PCT Application Publication Nos. WO 2016/033570 and WO 2016/115559, incorporated herein in their entirely. Exemplary genetic modification methods are also described in WO2017214207, and/or WO2016073602, the contents of which are hereby incorporated by reference in their entirety.

In some embodiments, the genetic modification includes genetically modifying the cells in a manner that enables the cells to express a chimeric molecule comprising a single chain variable fragment ("scFv") to recognize a protein. In some embodiments, the scFv binds to a specific protein. In some embodiments, the scFv is derived from a portion of an antibody that binds to a specific protein. In some embodiments, when the scFv is expressed by the cells, the cells are able to recognize cancer cells and activate themselves. In some embodiments, the scFv binds at least one of orphan tyrosine kinase receptor RORI, tEGFR, Her2, LI-CAM, CD19, CD20, CD22, mesothelin, CEA, and hepatitis B surface antigen, anti-folate receptor, CD23, CD24, CD30, CD33, CD38, CD44, EGFR, EGP-2, EGP-4, EPHa2, ErbB2, 3, or 4, FBP, fetal acethycholine receptor, GD2, GD3, HMW-MAA, IL-22R-alpha, IL-13R-alpha2, kdr, kappa light chain, Lewis Y, L1-cell adhesion molecule, MAGE-A1, mesothelin, MUC1, MUC16, BCMA, IL-13Ra2, FCRL5/FCRH5, GPRC5D, PSCA, NKG2D Ligands, NY-ESO-1, MART-1, gp100, oncofetal antigen, ROR1, TAG72, VEGF-R2, carcinoembryonic antigen (CEA), prostate specific antigen, PSMA, Her2/neu, estrogen receptor, progesterone receptor, ephrinB2, CD123, CS-1, c-Met, GD-2, and MAGE A3, CE7, Wilms Tumor 1 (WT-1), a cyclin, such as cyclin A1 (CCNA1), and/or biotinylated molecules, and/or molecules expressed by HIV, HCV, HBV or other pathogens. In some embodiments, the scFv binds CD19. In some embodiments, the scFv binds BCMA.

CARs

In some embodiments, the genetic modification includes genetically modifying the cells to express one or more chimeric antigen receptors (CARs). Exemplary antigen receptors, including CARs, and methods for engineering and introducing such receptors into cells, include those described, for example, in PCT Patent Application Publication Numbers WO 2000/14257, WO 2013/126726, WO 2012/129514, WO 2014/031687, WO 2013/166321, WO 2013/071154, WO 2013/123061 U.S. Patent Application Publication Nos. 2002/131960, 2013/287748, 2013/0149337, U.S. Pat. Nos. 6,451,995, 7,446,190, 8,252,592, 8,339,645, 8,398,282, 7,446,179, 6,410,319, 7,070,995, 7,265,209, 7,354,762, 7,446,191, 8,324,353, and 8,479,118, and European Patent No. EP 2537416, and/or those described by Sadelain et al., Cancer Discov., 3(4): 388-398 (2013); Davila et al. PLOS ONE 8(4): e61338 (2013); Turtle et al., Curr. Opin. Immunol., 24(5): 633-39 (2012); Wu et al., Cancer, 18(2): 160-75 (2012). In some aspects, the antigen receptors include a CAR as described in U.S. Pat. No. 7,446,190, and those described in PCT Patent Application Publication No. WO 2014/055668 A1. Examples of the CARs include CARs as disclosed in any of the aforementioned publications, such as WO 2014/031687, U.S. Pat. Nos. 8,339,645, 7,446,179, U.S. 2013/0149337, U.S. Pat. Nos. 7,446,190, 8,389,282, Kochenderfer et al., Nature Reviews Clinical Oncology, 10, 267-276 (2013); Wang et al., J. Immunother. 35(9): 689-701 (2012); and Brentjens et al., Sci Transl Med., 5(177) (2013). See also WO 2014/031687, U.S. Pat. Nos. 8,339,645, 7,446,179, U.S. 2013/0149337, U.S. Pat. Nos. 7,446,190, and 8,389,282. The chimeric receptors, such as CARs, generally include an extracellular antigen binding domain, such as a portion of an antibody molecule, generally a variable heavy (VH) chain region and/or variable light (VL) chain region of the antibody, e.g., an scFv antibody fragment. In some embodiments, the chimeric receptors include an extracellular antigen binding domain that is not derived from an antibody molecule, such as a ligand or other binding moiety.

In some embodiments, the antigen targeted by the receptor is a polypeptide. In some embodiments, it is a carbohydrate or other molecule. In some embodiments, the antigen is selectively expressed or overexpressed on cells of the disease or condition, e.g., the tumor or pathogenic cells, as compared to normal or non-targeted cells or tissues. In other embodiments, the antigen is expressed on normal cells and/or is expressed on the engineered cells.

Antigens targeted by the receptors in some embodiments include orphan tyrosine kinase receptor RORI, tEGFR, Her2, LI-CAM, CD19, CD20, CD22, mesothelin, CEA, and hepatitis B surface antigen, anti-folate receptor, CD23, CD24, CD30, CD33, CD38, CD44, EGFR, EGP-2, EGP-4, EPHa2, ErbB2, 3, or 4, FBP, fetal acethycholine receptor, GD2, GD3, HMW-MAA, IL-22R-alpha, IL-13R-alpha2, kdr, kappa light chain, Lewis Y, L1-cell adhesion molecule, MAGE-A1, mesothelin, MUC1, MUC16, PSCA, NKG2D Ligands, NY-ESO-1, MART-1, gp100, oncofetal antigen, ROR1, TAG72, VEGF-R2, carcinoembryonic antigen (CEA), prostate specific antigen, PSMA, Her2/neu, estrogen receptor, progesterone receptor, ephrinB2, CD123, c-Met, GD-2, and MAGE A3, CE7, Wilms Tumor 1 (WT-1), a cyclin, such as cyclin A1 (CCNA1), and/or biotinylated molecules, and/or molecules expressed by HIV, HCV, HBV or other pathogens.

In some embodiments, the CAR binds a pathogen-specific antigen. In some embodiments, the CAR is specific for viral antigens (such as HIV, HCV, HBV, etc.), bacterial antigens, and/or parasitic antigens.

In some embodiments, the antibody portion of the recombinant receptor, e.g., CAR, further includes at least a portion of an immunoglobulin constant region, such as a hinge region, e.g., an IgG4 hinge region, and/or a CH1/CL and/or Fc region. In some embodiments, the constant region or portion is of a human IgG, such as IgG4 or IgG1. In some aspects, the portion of the constant region serves as a spacer region between the antigen-recognition component, e.g., scFv, and transmembrane domain. The spacer can be of a length that provides for increased responsiveness of the cell following antigen binding, as compared to in the absence of the spacer. Exemplary spacers, e.g., hinge regions, include those described in International Patent Application Publication Number WO 2014/031687. In some examples, the spacer is or is about 12 amino acids in length or is no more than 12 amino acids in length. Exemplary spacers include those having at least about 10 to 229 amino acids, about 10 to 200 amino acids, about 10 to 175 amino acids, about 10 to 150 amino acids, about 10 to 125 amino acids, about 10 to 100 amino acids, about 10 to 75 amino acids, about 10 to 50 amino acids, about 10 to 40 amino acids, about 10 to 30 amino acids, about 10 to 20 amino acids, or about 10 to 15 amino acids, and including any integer between the endpoints of any of the listed ranges. In some embodiments, a spacer region has about 12 amino acids or less, about 119 amino acids or less, or about 229 amino acids or less. Exemplary spacers include IgG4 hinge alone, IgG4 hinge linked to CH2 and CH3 domains, or IgG4 hinge linked to the CH3 domain. Exemplary spacers include, but are not limited to, those described in Hudecek et al. Clin. Cancer Res., 19:3153 (2013), International Patent Application Publication Number WO2014031687, U.S. Pat. No. 8,822,647 or U.S. Patent Application Publication No. 2014/0271635.

In some embodiments, the constant region or portion is of a human IgG, such as IgG4 or IgG1. In some embodiments, the spacer has the sequence ESKYGPPCPPCP. In some embodiments, the constant region or portion is of IgD.

The antigen recognition domain generally is linked to one or more intracellular signaling components, such as signaling components that mimic activation through an antigen receptor complex, such as a TCR complex, in the case of a CAR, and/or signal via another cell surface receptor. Thus, in some embodiments, the antigen-binding component (e.g., antibody) is linked to one or more transmembrane and intracellular signaling domains. In some embodiments, the transmembrane domain is fused to the extracellular domain.

In one embodiment, a transmembrane domain that naturally is associated with one of the domains in the receptor, e.g., CAR, is used. In some instances, the transmembrane domain is selected or modified by amino acid substitution to avoid binding of such domains to the transmembrane domains of the same or different surface membrane proteins to minimize interactions with other members of the receptor complex.

The transmembrane domain in some embodiments is derived either from a natural or from a synthetic source. Where the source is natural, the domain in some aspects is derived from any membrane-bound or transmembrane protein. Transmembrane regions include those derived from (i.e. comprise at least the transmembrane region(s) of) the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154. Alternatively the transmembrane domain in some embodiments is synthetic. In some aspects, the synthetic transmembrane domain comprises predominantly hydrophobic residues such as leucine and valine. In some aspects, a triplet of phenylalanine, tryptophan and valine will be found at each end of a synthetic transmembrane domain. In some embodiments, the linkage is by linkers, spacers, and/or transmembrane domain(s).

Among the intracellular signaling domains are those that mimic or approximate a signal through a natural antigen receptor, a signal through such a receptor in combination with a costimulatory receptor, and/or a signal through a costimulatory receptor alone. In some embodiments, a short oligo- or polypeptide linker, for example, a linker of between 2 and 10 amino acids in length, such as one containing glycines and serines, e.g., glycine-serine doublet, is present and forms a linkage between the transmembrane domain and the cytoplasmic signaling domain of the CAR.

The receptor, e.g., the CAR, generally includes at least one intracellular signaling component or components. In some embodiments, the receptor includes an intracellular component of a TCR complex, such as a TCR CD3 chain that mediates T-cell activation and cytotoxicity, e.g., CD3 zeta chain. Thus, in some aspects, the antigen-binding portion is linked to one or more cell signaling modules. In some embodiments, cell signaling modules include CD3 transmembrane domain, CD3 intracellular signaling domains, and/or other CD transmembrane domains. In some embodiments, the receptor, e.g., CAR, further includes a portion of one or more additional molecules such as Fc receptor γ, CD8, CD4, CD25, or CD16. For example, in some aspects, the CAR or other chimeric receptor includes a chimeric molecule between CD3-zeta (CD3-2) or Fc receptor γ and CD8, CD4, CD25 or CD16.

In some embodiments, upon ligation of the CAR or other chimeric receptor, the cytoplasmic domain or intracellular signaling domain of the receptor activates at least one of the normal effector functions or responses of the immune cell, e.g., T cell engineered to express the CAR. For example, in some contexts, the CAR induces a function of a T cell such as cytolytic activity or T-helper activity, such as secretion of cytokines or other factors. In some embodiments, a truncated portion of an intracellular signaling domain of an antigen receptor component or costimulatory molecule is used in place of an intact immunostimulatory chain, for example, if it transduces the effector function signal. In some embodiments, the intracellular signaling domain or domains include the cytoplasmic sequences of the T cell receptor (TCR), and in some aspects also those of co-receptors that in the natural context act in concert with such receptors to initiate signal transduction following antigen receptor engagement.

In the context of a natural TCR, full activation generally requires not only signaling through the TCR, but also a costimulatory signal. Thus, in some embodiments, to promote full activation, a component for generating secondary or co-stimulatory signal is also included in the CAR. In other embodiments, the CAR does not include a component for generating a costimulatory signal. In some aspects, an additional CAR is expressed in the same cell and provides the component for generating the secondary or costimulatory signal.

T cell activation is in some aspects described as being mediated by two classes of cytoplasmic signaling sequences: those that initiate antigen-dependent primary activation through the TCR (primary cytoplasmic signaling sequences), and those that act in an antigen-independent manner to provide a secondary or co-stimulatory signal (secondary cytoplasmic signaling sequences). In some aspects, the CAR includes one or both of such signaling components.

In some aspects, the CAR includes a primary cytoplasmic signaling sequence that regulates primary activation of the TCR complex. Primary cytoplasmic signaling sequences that act in a stimulatory manner may contain signaling motifs which are known as immunoreceptor tyrosine-based activation motifs or ITAMs. Examples of ITAM containing primary cytoplasmic signaling sequences include those derived from CD3 zeta chain, FcR gamma, CD3 gamma, CD3 delta and CD3 epsilon. In some embodiments, cytoplasmic signaling molecule(s) in the CAR contain(s) a cytoplasmic signaling domain, portion thereof, or sequence derived from CD3 zeta.

In some embodiments, the CAR includes a signaling domain and/or transmembrane portion of a costimulatory receptor, such as CD28, 4-1BB, OX40, DAP10, and ICOS. In some aspects, the same CAR includes both the activating and costimulatory components.

In some embodiments, the activating domain is included within one CAR, whereas the costimulatory component is provided by another CAR recognizing another antigen. In some embodiments, the CARs include activating or stimulatory CARs, costimulatory CARs, both expressed on the same cell (see WO2014/055668). In some aspects, the cells include one or more stimulatory or activating CAR and/or a costimulatory CAR. In some embodiments, the cells further include inhibitory CARs (iCARs, see Fedorov et al., Sci. Transl. Medicine, 5(215) (2013)), such as a CAR recognizing an antigen other than the one associated with and/or specific for the disease or condition whereby an activating signal delivered through the disease-targeting CAR is diminished or inhibited by binding of the inhibitory CAR to its ligand, e.g., to reduce off-target effects.

In certain embodiments, the intracellular signaling domain comprises a CD28 transmembrane and signaling domain linked to a CD3 (e.g., CD3-zeta) intracellular domain. In some embodiments, the intracellular signaling domain comprises a chimeric CD28 and CD137 (4-1BB, TNFRSF9) co-stimulatory domains, linked to a CD3 zeta intracellular domain.

In some embodiments, the CAR encompasses one or more, e.g., two or more, costimulatory domains and an activation domain, e.g., primary activation domain, in the cytoplasmic portion. Exemplary CARs include intracellular components of CD3-zeta, CD28, and 4-1BB.

In some embodiments, the CAR or other antigen receptor further includes a marker, such as a cell surface marker, which may be used to confirm transduction or engineering of the cell to express the receptor, such as a truncated version of a cell surface receptor, such as truncated EGFR (tEGFR). In some aspects, the marker includes all or part (e.g., truncated form) of PSMA, Her2, CD34, a NGFR, or epidermal growth factor receptor (e.g., tEGFR). In some embodiments, the nucleic acid encoding the marker is operably linked to a polynucleotide encoding for a linker sequence, such as a cleavable linker sequence, e.g., T2A. For example, a marker, and optionally a linker sequence, can be any as disclosed in PCT Patent Application Publication No. WO 2014 031687, which is incorporated herein by reference. In some embodiments, the marker may be as described in PCT Patent Application Publication No. WO 2011/056894, the contents of which are incorporated in its entirety. For example, the marker can be a truncated EGFR (tEGFR) that is, optionally, linked to a linker sequence, such as a T2A cleavable linker sequence.

In some embodiments, the marker is a molecule, e.g., cell surface protein, not naturally found on T cells or not naturally found on the surface of T cells, or a portion thereof. In some embodiments, the molecule is a non-self molecule, e.g., non-self protein, i.e., one that is not recognized as "self" by the immune system of the host into which the cells will be adoptively transferred.

In some embodiments, the marker serves no therapeutic function and/or produces no effect other than to be used as a marker for genetic engineering, e.g., for selecting cells successfully engineered. In other embodiments, the marker may be a therapeutic molecule or molecule otherwise exerting some desired effect, such as a ligand for a cell to be encountered in vivo, such as a costimulatory or immune checkpoint molecule to enhance and/or dampen responses of the cells upon adoptive transfer and encounter with ligand.

In some cases, CARs are referred to as first, second, and/or third generation CARs. In some aspects, a first generation CAR is one that solely provides a CD3-chain induced signal upon antigen binding; in some aspects, a second-generation CARs is one that provides such a signal and costimulatory signal, such as one including an intracellular signaling domain from a costimulatory receptor such as CD28 or CD137; in some aspects, a third generation CAR is one that includes multiple costimulatory domains of different costimulatory receptors.

In some embodiments, the chimeric antigen receptor includes an extracellular portion containing an antibody or antibody fragment. In some aspects, the chimeric antigen receptor includes an extracellular portion containing the antibody or fragment and an intracellular signaling domain. In some embodiments, the antibody or fragment includes an scFv and the intracellular domain contains an ITAM. In some aspects, the intracellular signaling domain includes a signaling domain of a zeta chain of a CD3-zeta (CD3ζ) chain. In some embodiments, the chimeric antigen receptor includes a transmembrane domain linking the extracellular domain and the intracellular signaling domain. In some aspects, the transmembrane domain contains a transmembrane portion of CD28. In some embodiments, the chimeric antigen receptor contains an intracellular domain of a T cell costimulatory molecule. The extracellular domain and transmembrane domain can be linked directly or indirectly. In some embodiments, the extracellular domain and transmembrane domain are linked by a spacer, such as any described herein. In some embodiments, the receptor contains an extracellular portion of the molecule from which the transmembrane domain is derived, such as a CD28 extracellular portion. In some embodiments, the chimeric antigen receptor contains an intracellular domain derived from a T cell costimulatory molecule or a functional variant thereof, such as between the transmembrane domain and intracellular signaling domain. In some aspects, the T cell costimulatory molecule is CD28 or 41BB.

For example, in some embodiments, the CAR contains an antibody, e.g., an antibody fragment, a transmembrane domain that is or contains a transmembrane portion of CD28 or a functional variant thereof, and an intracellular signaling domain containing a signaling portion of CD28 or functional variant thereof and a signaling portion of CD3 zeta or functional variant thereof. In some embodiments, the CAR contains an antibody, e.g., antibody fragment, a transmembrane domain that is or contains a transmembrane portion of CD28 or a functional variant thereof, and an intracellular signaling domain containing a signaling portion of a 4-1BB or functional variant thereof and a signaling portion of CD3 zeta or functional variant thereof. In some such embodiments, the receptor further includes a spacer containing a portion of an Ig molecule, such as a human Ig molecule, such as an Ig hinge, e.g. an IgG4 hinge, such as a hinge-only spacer.

In some embodiments, the transmembrane domain of the recombinant receptor, e.g., the CAR, is or includes a transmembrane domain of human CD28 (e.g. Accession No. P01747.1) or variant thereof.

In some embodiments, the intracellular signaling component(s) of the recombinant receptor, e.g. the CAR, contains an intracellular costimulatory signaling domain of human CD28 or a functional variant or portion thereof, such as a domain with an LL to GG substitution at positions 186-187 of a native CD28 protein. In some embodiments, the intracellular domain comprises an intracellular costimulatory signaling domain of 4-1BB (e.g. (Accession No. Q07011.1) or functional variant or portion thereof.

In some embodiments, the intracellular signaling domain of the recombinant receptor, e.g. the CAR, comprises a human CD3 zeta stimulatory signaling domain or functional variant thereof, such as an 112 AA cytoplasmic domain of isoform 3 of human CD3ζ (Accession No.: P20963.2) or a CD3 zeta signaling domain as described in U.S. Pat. No. 7,446,190 or U.S. Pat. No. 8,911,993

In some aspects, the spacer contains only a hinge region of an IgG, such as only a hinge of IgG4 or IgG1. In other embodiments, the spacer is or contains an Ig hinge, e.g., an IgG4-derived hinge, optionally linked to a CH2 and/or CH3 domains. In some embodiments, the spacer is an Ig hinge, e.g., an IgG4 hinge, linked to CH2 and CH3 domains. In some embodiments, the spacer is an Ig hinge, e.g., an IgG4 hinge, linked to a CH3 domain only. In some embodiments, the spacer is or comprises a glycine-serine rich sequence or other flexible linker such as known flexible linkers.

For example, in some embodiments, the CAR includes an antibody such as an antibody fragment, including scFvs, a spacer, such as a spacer containing a portion of an immunoglobulin molecule, such as a hinge region and/or one or more constant regions of a heavy chain molecule, such as an Ig-hinge containing spacer, a transmembrane domain containing all or a portion of a CD28-derived transmembrane domain, a CD28-derived intracellular signaling domain, and a CD3 zeta signaling domain. In some embodiments, the CAR includes an antibody or fragment, such as scFv, a spacer such as any of the Ig-hinge containing spacers, a CD28-derived transmembrane domain, a 4-1BB-derived intracellular signaling domain, and a CD3 zeta-derived signaling domain.

In some embodiments, nucleic acid molecules encoding such CAR constructs further includes a sequence encoding a T2A ribosomal skip element and/or a tEGFR sequence, e.g., downstream of the sequence encoding the CAR. In some embodiments, T cells expressing an antigen receptor (e.g. CAR) can also be generated to express a truncated EGFR (EGFRt) as a non-immunogenic selection epitope (e.g. by introduction of a construct encoding the CAR and EGFRt separated by a T2A ribosome switch to express two proteins from the same construct), which then can be used as a marker to detect such cells (see, e.g., U.S. Pat. No. 8,802,374).

The recombinant receptors, such as CARs, expressed by the cells administered to the subject generally recognize or specifically bind to a molecule that is expressed in, associated with, and/or specific for the disease or condition or cells thereof being treated. Upon specific binding to the molecule, e.g., antigen, the receptor generally delivers an immunostimulatory signal, such as an ITAM-transduced signal, into the cell, thereby promoting an immune response targeted to the disease or condition. For example, in some embodiments, the cells express a CAR that specifically binds to an antigen expressed by a cell or tissue of the disease or condition or associated with the disease or condition.

TCRs

In some embodiments, the genetic modification includes genetically modifying the cells to express one or more T cell receptors (TCRs) or antigen-binding portion thereof that recognizes a peptide epitope or T cell epitope of a target polypeptide, such as an antigen of a tumor, viral or autoimmune protein.

In some embodiments, a "T cell receptor" or "TCR" is a molecule that contains a variable α and β chains (also known as TCRα and TCRβ, respectively) or a variable γ and δ chains (also known as TCR γ and TCR δ, respectively), or antigen-binding portions thereof, and which is capable of specifically binding to a peptide bound to an MHC molecule. In some embodiments, the TCR is in the αβ form. Typically, TCRs that exist in αβ and γδ forms are generally structurally similar, but T cells expressing them may have distinct anatomical locations or functions. A TCR can be found on the surface of a cell or in soluble form. Generally, a TCR is found on the surface of T cells (or T lymphocytes) where it is generally responsible for recognizing antigens bound to major histocompatibility complex (MHC) molecules.

Unless otherwise stated, the term "TCR" should be understood to encompass full TCRs as well as antigen-binding portions or antigen-binding fragments thereof. In some embodiments, the TCR is an intact or full-length TCR, including TCRs in the αβ form or γδ form. In some embodiments, the TCR is an antigen-binding portion that is less than a full-length TCR but that binds to a specific peptide bound in an MHC molecule, such as binds to an MHC-peptide complex. In some cases, an antigen-binding portion or fragment of a TCR can contain only a portion of the structural domains of a full-length or intact TCR, but yet is able to bind the peptide epitope, such as MHC-peptide complex, to which the full TCR binds. In some cases, an antigen-binding portion contains the variable domains of a TCR, such as variable α chain and variable β chain of a TCR, sufficient to form a binding site for binding to a specific MHC-peptide complex. Generally, the variable chains of a TCR contain complementarity determining regions involved in recognition of the peptide, MHC and/or MHC-peptide complex.

In some embodiments, the variable domains of the TCR contain hypervariable loops, or complementarity determining regions (CDRs), which generally are the primary contributors to antigen recognition and binding capabilities and specificity. In some embodiments, a CDR of a TCR or combination thereof forms all or substantially all of the antigen-binding site of a given TCR molecule. The various CDRs within a variable region of a TCR chain generally are separated by framework regions (FRs), which generally display less variability among TCR molecules as compared to the CDRs (see, e.g., Jores et al., Proc. Nat'l Acad. Sci. U.S.A. 87:9138, 1990; Chothia et al., EMBO J. 7:3745, 1988; see also Lefranc et al., Dev. Comp. Immunol. 27:55, 2003). In some embodiments, CDR3 is the main CDR responsible for antigen binding or specificity, or is the most important among the three CDRs on a given TCR variable region for antigen recognition, and/or for interaction with the processed peptide portion of the peptide-MHC complex. In some contexts, the CDR1 of the alpha chain can interact with the N-terminal part of certain antigenic peptides. In some contexts, CDR1 of the beta chain can interact with the C-terminal part of the peptide. In some contexts, CDR2 contributes most strongly to or is the primary CDR responsible for the interaction with or recognition of the MHC portion of the MHC-peptide complex. In some embodiments, the variable region of the β-chain can contain a further hypervariable region (CDR4 or HVR4), which generally is involved in superantigen binding and not antigen recognition (Kotb (1995) Clinical Microbiology Reviews, 8:411-426).

In some embodiments, a TCR also can contain a constant domain, a transmembrane domain and/or a short cytoplasmic tail (see, e.g., Janeway et al., Immunobiology: The Immune System in Health and Disease, 3rd Ed., Current Biology Publications, p. 4:33, 1997). In some aspects, each chain of the TCR can possess one N-terminal immunoglobulin variable domain, one immunoglobulin constant domain, a transmembrane region, and a short cytoplasmic tail at the C-terminal end. In some embodiments, a TCR is associated with invariant proteins of the CD3 complex involved in mediating signal transduction.

In some embodiments, a TCR chain contains one or more constant domain. For example, the extracellular portion of a given TCR chain (e.g., α-chain or β-chain) can contain two immunoglobulin-like domains, such as a variable domain (e.g., Va or VB; typically amino acids 1 to 116 based on Kabat numbering (Kabat et al., "Sequences of Proteins of Immunological Interest, US Dept. Health and Human Services, Public Health Service National Institutes of Health, 1991, 5th ed.)) and a constant domain (e.g., α-chain constant domain or Cα, typically positions 117 to 259 of the chain based on Kabat numbering or β chain constant domain or Cβ, typically positions 117 to 295 of the chain based on Kabat) adjacent to the cell membrane. For example, in some cases, the extracellular portion of the TCR formed by the two chains contains two membrane-proximal constant domains, and two membrane-distal variable domains, which variable domains each contain CDRs. The constant domain of the TCR may contain short connecting sequences in which a cysteine residue forms a disulfide bond, thereby linking the two chains of the TCR. In some embodiments, a TCR may have an additional cysteine residue in each of the α and β chains, such that the TCR contains two disulfide bonds in the constant domains.

In some embodiments, the TCR chains contain a transmembrane domain. In some embodiments, the transmembrane domain is positively charged. In some cases, the TCR chain contains a cytoplasmic tail. In some cases, the structure allows the TCR to associate with other molecules like CD3 and subunits thereof. For example, a TCR containing constant domains with a transmembrane region may anchor the protein in the cell membrane and associate with invariant subunits of the CD3 signaling apparatus or complex. The intracellular tails of CD3 signaling subunits (e.g. CD3γ, CD3δ, CD3ε and CD3ζ chains) contain one or more immunoreceptor tyrosine-based activation motif or ITAM that are involved in the signaling capacity of the TCR complex.

In some embodiments, the TCR may be a heterodimer of two chains α and β (or optionally γ and δ) or it may be a single chain TCR construct. In some embodiments, the TCR is a heterodimer containing two separate chains (α and β chains or γ and δ chains) that are linked, such as by a disulfide bond or disulfide bonds.

In some embodiments, the TCR can be generated from a known TCR sequence(s), such as sequences of Vα,β chains, for which a substantially full-length coding sequence is readily available. Methods for obtaining full-length TCR sequences, including V chain sequences, from cell sources are well known. In some embodiments, nucleic acids encoding the TCR can be obtained from a variety of sources, such as by polymerase chain reaction (PCR) amplification of TCR-encoding nucleic acids within or isolated from a given cell or cells, or synthesis of publicly available TCR DNA sequences.

In some embodiments, the TCR is obtained from a biological source, such as from cells such as from a T cell (e.g. cytotoxic T cell), T-cell hybridomas or other publicly available source. In some embodiments, the T-cells can be obtained from in vivo isolated cells. In some embodiments, the TCR is a thymically selected TCR. In some embodiments, the TCR is a neoepitope-restricted TCR. In some embodiments, the T-cells can be a cultured T-cell hybridoma or clone. In some embodiments, the TCR or antigen-binding portion thereof can be synthetically generated from knowledge of the sequence of the TCR.

In some embodiments, the TCR is generated from a TCR identified or selected from screening a library of candidate TCRs against a target polypeptide antigen, or target T cell epitope thereof. TCR libraries can be generated by amplification of the repertoire of Va and VB from T cells isolated from a subject, including cells present in PBMCs, spleen or other lymphoid organ. In some cases, T cells can be amplified from tumor-infiltrating lymphocytes (TILs). In some embodiments, TCR libraries can be generated from $CD4^+$ or $CD8^+$ cells. In some embodiments, the TCRs can be amplified from a T cell source of a normal of healthy subject, i.e. normal TCR libraries. In some embodiments, the TCRs can be amplified from a T cell source of a diseased subject, i.e. diseased TCR libraries. In some embodiments, degenerate primers are used to amplify the gene repertoire of Va and VB, such as by RT-PCR in samples, such as T cells, obtained from humans. In some embodiments, scTv libraries can be assembled from naïve Va and VB libraries in which the amplified products are cloned or assembled to be separated by a linker. Depending on the source of the subject and cells, the libraries can be HLA allele-specific. Alternatively, in some embodiments, TCR libraries can be generated by mutagenesis or diversification of a parent or scaffold TCR molecule. In some aspects, the TCRs are subjected to directed evolution, such as by mutagenesis, e.g., of the α or β chain. In some aspects, particular residues within CDRs of the TCR are altered. In some embodiments, selected TCRs can be modified by affinity maturation. In some embodiments, antigen-specific T cells may be selected, such as by screening to assess CTL activity against the peptide. In some aspects, TCRs, e.g. present on the antigen-specific T cells, may be selected, such as by binding activity, e.g., particular affinity or avidity for the antigen.

In some embodiments, the TCR or antigen-binding portion thereof is one that has been modified or engineered. In some embodiments, directed evolution methods are used to generate TCRs with altered properties, such as with higher affinity for a specific MHC-peptide complex. In some embodiments, directed evolution is achieved by display methods including, but not limited to, yeast display (Holler et al. (2003) Nat Immunol, 4, 55-62; Holler et al. (2000) Proc Natl Acad Sci USA, 97, 5387-92), phage display (Li et al. (2005) Nat Biotechnol, 23, 349-54), or T cell display (Chervin et al. (2008) J Immunol Methods, 339, 175-84). In some embodiments, display approaches involve engineering, or modifying, a known, parent or reference TCR. For example, in some cases, a wild-type TCR can be used as a template for producing mutagenized TCRs in which in one or more residues of the CDRs are mutated, and mutants with an desired altered property, such as higher affinity for a desired target antigen, are selected.

In some embodiments, peptides of a target polypeptide for use in producing or generating a TCR of interest are known or can be readily identified by a skilled artisan. In some embodiments, peptides suitable for use in generating TCRs or antigen-binding portions can be determined based on the presence of an HLA-restricted motif in a target polypeptide of interest, such as a target polypeptide described below. In some embodiments, HLA-A0201 binding motifs, the cleavage sites for proteasomes and immune-proteasomes, and peptides are identified using computer prediction models known to those of skill in the art. In some embodiments, for predicting MHC class I binding sites, such models include, but are not limited to, ProPred1 (Singh and Raghava (2001) Bioinformatics 17(12): 1236-1237), and SYFPEITHI (see Schuler et al. (2007) Immunoinformatics Methods in Molecular Biology, 409(1): 75-93 2007). In some embodiments, the MHC-restricted epitope is HLA-A0201, which is expressed in approximately 39-46% of all Caucasians and therefore, represents a suitable choice of MHC antigen for use preparing a TCR or other MHC-peptide binding molecule.

In some embodiments, the TCR or antigen binding portion thereof may be a recombinantly produced natural protein or mutated form thereof in which one or more property, such as binding a characteristic, has been altered. In some embodiments, a TCR may be derived from one of various animal species, such as human, mouse, rat, or other mammal. A TCR may be cell-bound or in soluble form. In some embodiments, for purposes of the provided methods, the TCR is in cell-bound form expressed on the surface of a cell.

In some embodiments, the TCR is a full-length TCR. In some embodiments, the TCR is an antigen-binding portion. In some embodiments, the TCR is a dimeric TCR (dTCR). In some embodiments, the TCR is a single-chain TCR (sc-TCR). In some embodiments, a dTCR or scTCR have the structures as described in WO 03/020763, WO 04/033685, WO 2011/044186, which are incorporated herein by reference.

In some embodiments, the TCR contains a sequence corresponding to the transmembrane sequence. In some embodiments, the TCR does contain a sequence corresponding to cytoplasmic sequences. In some embodiments, the TCR is capable of forming a TCR complex with CD3. In some embodiments, any of the TCRs, including a dTCR or scTCR, can be linked to signaling domains that yield an active TCR on the surface of a T cell. In some embodiments, the TCR is expressed on the surface of cells.

In some embodiments a dTCR contains a first polypeptide wherein a sequence corresponding to a TCR α chain variable region sequence is fused to the N terminus of a sequence corresponding to a TCR α chain constant region extracellular sequence, and a second polypeptide wherein a sequence corresponding to a TCR β chain variable region sequence is fused to the N terminus a sequence corresponding to a TCR β chain constant region extracellular sequence, the first and second polypeptides being linked by a disulfide bond. In some embodiments, the bond can correspond to the native inter-chain disulfide bond present in native dimeric αβ TCRs. In some embodiments, the interchain disulfide bonds are not present in a native TCR. For example, in some embodiments, one or more cysteines can be incorporated into the constant region extracellular sequences of dTCR polypeptide pair. In some cases, both a native and a non-native disulfide bond may be desirable. In some embodiments, the TCR contains a transmembrane sequence to anchor to the membrane.

In some embodiments, a dTCR contains a TCR α chain containing a variable α domain, a constant α domain and a first dimerization motif attached to the C-terminus of the constant α domain, and a TCR β chain comprising a variable β domain, a constant β domain and a first dimerization motif attached to the C-terminus of the constant β domain, wherein the first and second dimerization motifs easily interact to form a covalent bond between an amino acid in the first dimerization motif and an amino acid in the second dimerization motif linking the TCR α chain and TCR β chain together.

In some embodiments, the TCR is a scTCR. Typically, a scTCR can be generated using methods known to those of skill in the art, see, e.g., Soo Hoo, W. F. et al. PNAS (USA) 89, 4759 (1992); Wülfing, C. and Plückthun, A., J. Mol. Biol. 242, 655 (1994); Kurucz, I. et al. PNAS (USA) 90 3830 (1993); PCT Application Publication Nos. WO 96/13593, WO 96/18105, WO99/60120, WO99/18129, WO 03/020763, WO 2011/044186; and Schlueter, C. J. et al. J. Mol. Biol. 256, 859 (1996). In some embodiments, a scTCR contains an introduced non-native disulfide interchain bond to facilitate the association of the TCR chains (see e.g. PCT Application Publication No. WO 03/020763, which is incorporated herein by reference). In some embodiments, a scTCR is a non-disulfide linked truncated TCR in which heterologous leucine zippers fused to the C-termini thereof facilitate chain association (see, e.g., PCT Application Publication No. WO99/60120, which is incorporated herein by reference). In some embodiments, a scTCR contain a TCRα variable domain covalently linked to a TCRβ variable domain via a peptide linker (see e.g., PCT Application Publication No. WO 99/18129, which is incorporated herein by reference).

In some embodiments, a scTCR contains a first segment constituted by an amino acid sequence corresponding to a TCR α chain variable region, a second segment constituted by an amino acid sequence corresponding to a TCR β chain variable region sequence fused to the N terminus of an amino acid sequence corresponding to a TCR β chain constant domain extracellular sequence, and a linker sequence linking the C terminus of the first segment to the N terminus of the second segment.

In some embodiments, a scTCR contains a first segment constituted by an α chain variable region sequence fused to the N terminus of an α chain extracellular constant domain sequence, and a second segment constituted by a β chain variable region sequence fused to the N terminus of a sequence β chain extracellular constant and transmembrane sequence, and, optionally, a linker sequence linking the C terminus of the first segment to the N terminus of the second segment.

In some embodiments, a scTCR contains a first segment constituted by a TCR β chain variable region sequence fused to the N terminus of a β chain extracellular constant domain sequence, and a second segment constituted by an α chain variable region sequence fused to the N terminus of a sequence α chain extracellular constant and transmembrane sequence, and, optionally, a linker sequence linking the C terminus of the first segment to the N terminus of the second segment.

In some embodiments, the linker of a scTCRs that links the first and second TCR segments can be any linker capable of forming a single polypeptide strand, while retaining TCR binding specificity. In some embodiments, the linker sequence may, for example, have the formula —P-AA-P— wherein P is proline and AA represents an amino acid sequence wherein the amino acids are glycine and/or serine. In some embodiments, the first and second segments are paired so that the variable region sequences thereof are orientated for such binding. Hence, in some cases, the linker has a sufficient length to span the distance between the C terminus of the first segment and the N terminus of the second segment, or vice versa, but is not too long to block or reduce bonding of the scTCR to the target ligand. In some embodiments, the linker can contain from or from about 10 to 45 amino acids, such as 10 to 30 amino acids or 26 to 41 amino acids residues, for example 29, 30, 31 or 32 amino acids. In some embodiments, the linker has the formula —PGGG-(SGGGG)5-P— (SEQ ID NO: 2) wherein P is proline, G is glycine and S is serine. In some embodiments, the linker has the sequence GSADDAKKDAAKKDGKS (SEQ ID NO: 3).

In some embodiments, the scTCR contains a covalent disulfide bond linking a residue of the immunoglobulin region of the constant domain of the α chain to a residue of the immunoglobulin region of the constant domain of the β chain. In some embodiments, the interchain disulfide bond in a native TCR is not present. For example, in some embodiments, one or more cysteines can be incorporated into the constant region extracellular sequences of the first and second segments of the scTCR polypeptide. In some cases, both a native and a non-native disulfide bond may be desirable.

In some embodiments of a dTCR or scTCR containing introduced interchain disulfide bonds, the native disulfide bonds are not present. In some embodiments, the one or more of the native cysteines forming a native interchain disulfide bonds are substituted to another residue, such as to a serine or alanine. In some embodiments, an introduced disulfide bond can be formed by mutating non-cysteine residues on the first and second segments to cysteine. Exemplary non-native disulfide bonds of a TCR are described in PCT Application Publication No. WO 2006/000830, which is incorporated herein by reference.

In some embodiments, the TCR or antigen-binding fragment thereof exhibits an affinity with an equilibrium binding constant for a target antigen of between or between about 10-5 and 10-12 M and all individual values and ranges therein. In some embodiments, the target antigen is an MHC-peptide complex or ligand.

In some embodiments, nucleic acid or nucleic acids encoding a TCR, such as α and β chains, can be amplified by PCR or other suitable means and cloned into a suitable expression vector or vectors. The expression vector can be any suitable recombinant expression vector, and can be used to transform or transfect any suitable host. Suitable vectors include those designed for propagation and expansion, or for expression, or both, such as plasmids and viruses.

In some embodiments, the vector can be a vector of the pUC series (Fermentas Life Sciences), the pBluescript series (Stratagene, LaJolla, Calif.), the pET series (Novagen, Madison, Wis.), the pGEX series (Pharmacia Biotech, Uppsala, Sweden), or the pEX series (Clontech, Palo Alto, Calif.). In some cases, bacteriophage vectors, such as AG10, AGT11, AZapll (Stratagene), AEMBL4, and ANM1149, also can be used. In some embodiments, plant expression vectors can be used and include pBI01, pBI101.2, pBI101.3, pBI121 and pBIN19 (Clontech). In some embodiments, animal expression vectors include pEUK-CI, pMAM and pMAMneo (Clontech). In some embodiments, a viral vector is used, such as a retroviral vector.

In some embodiments, the recombinant expression vectors can be prepared using standard recombinant DNA techniques. In some embodiments, vectors can contain regulatory sequences, such as transcription and translation initiation and termination codons, which are specific to the type of host (e.g., bacterium, fungus, plant, or animal) into which the vector is to be introduced, as appropriate, and taking into consideration whether the vector is DNA- or RNA-based. In some embodiments, the vector can contain a nonnative promoter operably linked to the nucleotide sequence encoding the TCR or antigen-binding portion (or other MHC-peptide binding molecule). In some embodiments, the promoter can be a non-viral promoter or a viral promoter, such as a cytomegalovirus (CMV) promoter, an SV40 promoter, an RSV promoter, and a promoter found in the long-terminal repeat of the murine stem cell virus. Other promoters known to a skilled artisan also are contemplated.

In some embodiments, to generate a vector encoding a TCR, the α and β chains are PCR amplified from total cDNA isolated from a T cell clone expressing the TCR of interest and cloned into an expression vector. In some embodiments, the α and β chains are cloned into the same vector. In some embodiments, the α and β chains are cloned into different vectors. In some embodiments, the generated α and β chains are incorporated into a retroviral, e.g. lentiviral, vector.

Multi-Targeting

In some embodiments, the genetic modification includes genetically modifying the cells to express two or more genetically engineered receptors on the cell, each recognizing the same or a different antigen and, in some embodiments, each including a different intracellular signaling component. Such multi-targeting strategies are described, for example, in PCT Patent Application Publication No.: WO 2014/055668 A1 and Fedorov et al., Sci. Transl. Medicine, 5(215) (2013).

For example, in some embodiments, the cells include a receptor expressing a first genetically engineered antigen receptor (e.g., CAR or TCR) which is capable of inducing an activating signal to the cell, generally upon specific binding to the antigen recognized by the first receptor, e.g., the first antigen. In some embodiments, the cell further includes a second genetically engineered antigen receptor (e.g., CAR or TCR), e.g., a chimeric costimulatory receptor, which is capable of inducing a costimulatory signal to the immune cell, generally upon specific binding to a second antigen recognized by the second receptor. In some embodiments, the first antigen and second antigen are the same. In some embodiments, the first antigen and second antigen are different.

In some embodiments, the first and/or second genetically engineered antigen receptor (e.g. CAR or TCR) is capable of inducing an activating signal to the cell. In some embodiments, the receptor includes an intracellular signaling component containing ITAM or ITAM-like motifs. In some embodiments, the activation induced by the first receptor involves a signal transduction or change in protein expression in the cell resulting in initiation of an immune response, such as ITAM phosphorylation and/or initiation of ITAM-mediated signal transduction cascade, formation of an immunological synapse and/or clustering of molecules near the bound receptor (e.g. CD4 or CD8, etc.), activation of one or more transcription factors, such as NF-κB and/or AP-1, and/or induction of gene expression of factors such as cytokines, proliferation, and/or survival.

In some embodiments, the first and/or second receptor includes intracellular signaling domains of costimulatory receptors such as CD28, CD137 (4-1 BB), OX40, and/or ICOS. In some embodiments, the first and second receptor include an intracellular signaling domain of a costimulatory receptor that are different. In some embodiments, the first receptor contains a CD28 costimulatory signaling region and the second receptor contain a 4-1BB co-stimulatory signaling region or vice versa.

In some embodiments, the first and/or second receptor includes both an intracellular signaling domain containing ITAM or ITAM-like motifs and an intracellular signaling domain of a costimulatory receptor.

In some embodiments, the first receptor contains an intracellular signaling domain containing ITAM or ITAM-like motifs and the second receptor contains an intracellular signaling domain of a costimulatory receptor. The costimulatory signal in combination with the activating signal induced in the same cell is one that results in an immune response, such as a robust and sustained immune response, such as increased gene expression, secretion of cytokines and other factors, and T cell mediated effector functions such as cell killing.

In some embodiments, neither ligation of the first receptor alone nor ligation of the second receptor alone induces a robust immune response. In some aspects, if only one receptor is ligated, the cell becomes tolerized or unresponsive to antigen, or inhibited, and/or is not induced to proliferate or secrete factors or carry out effector functions. In some such embodiments, however, when the plurality of receptors are ligated, such as upon encounter of a cell expressing the first and second antigens, a desired response is achieved, such as full immune activation or stimulation, e.g., as indicated by secretion of one or more cytokine, proliferation, persistence, and/or carrying out an immune effector function such as cytotoxic killing of a target cell.

In some embodiments, the two receptors induce, respectively, an activating and an inhibitory signal to the cell, such that binding by one of the receptors to its antigen activates the cell or induces a response, but binding by the second inhibitory receptor to its antigen induces a signal that suppresses or dampens that response. Examples are combinations of activating CARs and inhibitory CARs or iCARs. Such a strategy may be used, for example, in which the activating CAR binds an antigen expressed in a disease or condition but which is also expressed on normal cells, and the inhibitory receptor binds to a separate antigen which is expressed on the normal cells but not cells of the disease or condition.

In some embodiments, the multi-targeting strategy is employed in a case where an antigen associated with a particular disease or condition is expressed on a non-diseased cell and/or is expressed on the engineered cell itself, either transiently (e.g., upon stimulation in association with genetic engineering) or permanently. In such cases, by requiring ligation of two separate and individually specific antigen receptors, specificity, selectivity, and/or efficacy may be improved.

In some embodiments, the plurality of antigens, e.g., the first and second antigens, are expressed on the cell, tissue, or disease or condition being targeted, such as on the cancer cell. In some aspects, the cell, tissue, disease or condition is multiple myeloma or a multiple myeloma cell. In some embodiments, one or more of the plurality of antigens generally also is expressed on a cell which it is not desired to target with the cell therapy, such as a normal or non-diseased cell or tissue, and/or the engineered cells themselves. In such embodiments, by requiring ligation of multiple receptors to achieve a response of the cell, specificity and/or efficacy is achieved.

In some embodiments, the cell modification is performed based on an analysis of the cells after collection and before being cryogenically frozen and/or stored. The cells may be modified, based on the analysis, before and/or after cryogenic storage. In some embodiments, the cell modification is performed based on an analysis of the cells after thawing following cryogenic storage. In some embodiments, the analysis involves determining the ratio of the $CD4^+$ cells to $CD8^+$ cells. In some embodiments, conditions for the post-cryogenic modification, such as a time for incubating the cells, a temperature for incubating the cells, the use and concentration of a cell stimulant, and the steps for genetically modifying the cells, may be selected based on the analysis or may be selected based on the ratio of the $CD4^+$ cells to $CD8^+$ cells.

Vectors for Engineering Cells

Polynucleotides (nucleic acid molecules) encoding the recombinant receptors and/or TCRs can be included in vectors for genetically engineering cells to express such receptors. In some embodiments, the vectors or constructs contain one or more promoters operatively linked to the nucleotide encoding the polypeptide or receptor to drive expression thereof. In some embodiments, the promoter is operatively linked to one or more than one nucleic acid molecule. In some cases, the vector is a viral vector, such as a retroviral vector, e.g., a lentiviral vector or a gammaretroviral vector. In some embodiments, the polynucleotide, such as a vector, encoding the recombinant receptor is introduced into a composition containing cultured cells, such as by retroviral transduction, transfection, or transformation.

Various methods for the introduction of genetically engineered components, e.g., recombinant receptors, e.g., CARs or TCRs, are well known and may be used with the provided methods and compositions. Exemplary methods include those for transfer of nucleic acids encoding the polypeptides or receptors, including via viral vectors, e.g., retroviral or lentiviral, non-viral vectors or transposons, e.g. Sleeping Beauty transposon system. Methods of gene transfer can include transduction, electroporation or other method that results into gene transfer into the cell.

In some embodiments, gene transfer is accomplished by first stimulating the cell, such as by combining it with a stimulus that induces a response such as proliferation, survival, and/or activation, e.g., as measured by expression of a cytokine or activation marker, followed by transduction of the activated cells, and expansion in culture to numbers sufficient for clinical applications.

In some contexts, it may be desired to safeguard against the potential that overexpression of a stimulatory factor (for example, a lymphokine or a cytokine) could potentially result in an unwanted outcome or lower efficacy in a subject, such as a factor associated with toxicity in a subject. Thus, in some contexts, the engineered cells include gene segments that cause the cells to be susceptible to negative selection in vivo, such as upon administration in adoptive immunotherapy. For example in some aspects, the cells are engineered so that they can be eliminated as a result of a change in the in vivo condition of the patient to which they are administered. The negative selectable phenotype may result from the insertion of a gene that confers sensitivity to an administered agent, for example, a compound. Negative selectable genes include the Herpes simplex virus type I thymidine kinase (HSV-I TK) gene (Wigler et al., Cell II: 223, 1977) which confers ganciclovir sensitivity, the cellular hypoxanthine phosphribosyltransferase (HPRT) gene, the cellular adenine phosphoribosyltransferase (APRT) gene, bacterial cytosine deaminase (Mullen et al., Proc. Natl. Acad. Sci. USA. 89:33 (1992)), etc.

In some embodiments, recombinant nucleic acids are transferred into cells using recombinant infectious virus particles, such as, e.g., vectors derived from simian virus 40 (SV40), adenoviruses, adeno-associated virus (AAV), etc. In some embodiments, recombinant nucleic acids are transferred into T cells using recombinant lentiviral vectors or retroviral vectors, such as gamma-retroviral vectors (see, e.g., Koste et al. (2014) Gene Therapy 2014 Apr. 3. doi: 10.1038/gt.2014.25; Carlens et al. (2000) Exp Hematol 28(10): 1137-46; Alonso-Camino et al. (2013) Mol Ther Nucl Acids 2, e93; Park et al., Trends Biotechnol. 2011 Nov. 29(11): 550-557).

In some embodiments, the retroviral vector has a long terminal repeat sequence (LTR), e.g., a retroviral vector derived from the Moloney murine leukemia virus (MoMLV), myeloproliferative sarcoma virus (MPSV), murine embryonic stem cell virus (MESV), murine stem cell virus (MSCV), spleen focus forming virus (SFFV), or adeno-associated virus (AAV). Most retroviral vectors are derived from murine retroviruses. In some embodiments, the retroviruses include those derived from any avian or mammalian cell source. The retroviruses typically are amphotropic, meaning that they are capable of infecting host cells of several species, including humans. In one embodiment, the gene to be expressed replaces the retroviral gag, pol, and/or env sequences. A number of illustrative retroviral systems have been described (e.g., U.S. Pat. Nos. 5,219,740; 6,207,453; 5,219,740; Miller and Rosman (1989) BioTechniques 7:980-990; Miller, A. D. (1990) Human Gene Therapy 1:5-14; Scarpa et al. (1991) Virology 180:849-852; Burns et al. (1993) Proc. Natl. Acad. Sci. USA 90:8033-8037; and Boris-Lawrie and Temin (1993) Cur. Opin. Genet. Develop. 3:102-109).

Methods of lentiviral transduction are known. Exemplary methods are described in, e.g., Wang et al. (2012) J. Immunother. 35(9): 689-701; Cooper et al. (2003) Blood. 101: 1637-1644; Verhoeyen et al. (2009) Methods Mol Biol. 506:97-114; and Cavalieri et al. (2003) Blood. 102(2): 497-505.

In some embodiments, recombinant nucleic acids are transferred into T cells via electroporation (see, e.g., Chicaybam et al, (2013) PLOS ONE 8(3): e60298 and Van Tedeloo et al. (2000) Gene Therapy 7(16): 1431-1437). In some embodiments, recombinant nucleic acids are transferred into T cells via transposition (see, e.g., Manuri et al. (2010) Hum Gene Ther 21(4): 427-437; Sharma et al. (2013) Molec Ther Nucl Acids 2, e74; and Huang et al. (2009) Methods Mol Biol 506:115-126). Other methods of introducing and expressing genetic material in immune cells include calcium phosphate transfection (e.g., as described in Current Protocols in Molecular Biology, John Wiley & Sons, New York. N.Y.), protoplast fusion, cationic liposome-mediated transfection; tungsten particle-facilitated microparticle bombardment (Johnston, Nature, 346:776-777 (1990)); and strontium phosphate DNA co-precipitation (Brash et al., Mol. Cell Biol., 7:2031-2034 (1987)). In some aspects, a washing step is performed in a centrifugal chamber, for example those produced and sold by Biosafe SA, including those for use with the Sepax® and Sepax® 2 systems, including an A-200/F and A-200 centrifugal chambers according to the manufacturer's instructions.

Other approaches and vectors for transfer of the nucleic acids encoding the recombinant products are those described, e.g., in PCT Patent Application, Publication No.: WO/2014055668, and U.S. Pat. No. 7,446,190, which are incorporated herein by reference.

In some embodiments, the cells, e.g., T cells, may be transfected either during or after expansion, e.g. with a T cell receptor (TCR), or a chimeric antigen receptor (CAR). This transfection for the introduction of the gene of the desired polypeptide or receptor can be carried out with any suitable retroviral vector, for example. The genetically modified cell population can then be liberated from the initial stimulus (the CD3/CD28 stimulus, for example) and subsequently be stimulated with a second type of stimulus (e.g. via a de novo introduced receptor). This second type of stimulus may include an antigenic stimulus in form of a peptide/MHC molecule, the cognate (cross-linking) ligand of the genetically introduced receptor (e.g. natural ligand of a CAR) or any ligand (such as an antibody) that directly binds within the framework of the new receptor (e.g. by recognizing constant regions within the receptor). See, for example, Cheadle et al, "Chimeric antigen receptors for T-cell based therapy" Methods Mol Biol. 2012; 907:645-66 or Barrett et al., Chimeric Antigen Receptor Therapy for Cancer Annual Review of Medicine Vol. 65:333-347 (2014).

Among additional nucleic acids, e.g., genes for introduction are those to improve the efficacy of therapy, such as by promoting viability and/or function of transferred cells; genes to provide a genetic marker for selection and/or evaluation of the cells, such as to assess in vivo survival or localization; and genes to improve safety, for example, by making the cell susceptible to negative selection in vivo as described by Lupton S. D. et al., Mol. and Cell Biol., 11:6 (1991); and Riddell et al., Human Gene Therapy 3:319-338 (1992); see also the publications of PCT/US91/08442 and PCT/US94/05601 by Lupton et al. describing the use of bifunctional selectable fusion genes derived from fusing a dominant positive selectable marker with a negative selectable marker. See, e.g., Riddell et al., U.S. Pat. No. 6,040,177, at columns 14-17.

In some embodiments, the cells are incubated and/or cultured prior to or in connection with genetic engineering. The incubation steps can include culture, cultivation, stimulation, activation, and/or propagation. The incubation and/or engineering may be carried out in a culture vessel, such as a unit, chamber, well, column, tube, tubing set, valve, vial, culture dish, bag, or other container for culture or cultivating cells. In some embodiments, the compositions or cells are incubated in the presence of stimulating conditions or a stimulatory agent. Such conditions include those designed to induce proliferation, expansion, activation, and/or survival of cells in the population, to mimic antigen exposure, and/or to prime the cells for genetic engineering, such as for the introduction of a recombinant antigen receptor. In some embodiments, one or more of the incubation steps may be carried out using a rocking bioreactor, such as the WAVE™ Bioreactor (GE Healthcare) or the BIOSTAT® RM (Sartorius). In some embodiments, one or more of the incubation steps may be carried out using a static bioreactor or incubation chamber. In specific embodiments, an anti-shear agent, for example a poloxamer, may be added to the composition if using a rocking bioreactor for one or more incubation steps.

The conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells. In some aspects, the cells are incubated in the presence of one or more cytokines and in some embodiments a cytokine cocktail can be employed, for example as described in PCT Patent Application Publication Number WO 2015/157384, which is incorporated by reference. In some embodiments, the cells are incubated with one or more cytokines and/or a cytokine cocktail prior to, concurrently with, or subsequent to transduction.

In some embodiments, the stimulating conditions or agents include one or more agent, e.g., ligand, which is capable of activating an intracellular signaling domain of a TCR complex. In some aspects, the agent turns on or initiates TCR/CD3 intracellular signaling cascade in a T cell. Such agents can include antibodies, such as those specific for a TCR component, e.g. anti-CD3. In some embodiments, the stimulating conditions include one or more agent, e.g. ligand, which is capable of stimulating a costimulatory receptor, e.g., anti-CD28. In some embodiments, such agents and/or ligands may be bound to a solid support such as a bead, and/or one or more cytokines. Optionally, the expansion method may further comprise the step of adding anti-CD3 and/or anti CD28 antibody to the culture medium (e.g., at a concentration of at least about 0.5 ng/ml). In some embodiments, the stimulating agents include IL-2, and/or IL-15, for example, an IL-2 concentration of at least about 10 units/mL.

In some aspects, incubation is carried out in accordance with techniques such as those described in U.S. Pat. No. 6,040,177 to Riddell et al., Klebanoff et al. (2012) J Immunother. 35(9): 651-660, Terakura et al. (2012) Blood. 1:72-82, and/or Wang et al. (2012) J Immunother. 35(9): 689-701. In some aspects, the transduction is carried out using a system, device, apparatus, and/or method as described in PCT Patent Application Publication Number WO 2016/073602 or US 2016/0122782 the contents of which are incorporated by reference in their entirety. In some embodiments, the transduction is carried out according to methods described in PCT Patent Application Publication Number WO 2015/164675, the contents of which are incorporated by reference in their entirety.

In some embodiments, the T cells are expanded by adding to a culture-initiating composition feeder cells, such as non-dividing peripheral blood mononuclear cells (PBMC), (e.g., such that the resulting population of cells contains at least about 5, 10, 20, or 40 or more PBMC feeder cells for each T lymphocyte in the initial population to be expanded); and incubating the culture (e.g. for a time sufficient to expand the numbers of T cells). In some aspects, the non-dividing feeder cells can comprise gamma-irradiated PBMC feeder cells. In some embodiments, the PBMC are irradiated with gamma rays in the range of about 3000 to 3600 rads to prevent cell division. In some aspects, the feeder cells are added to culture medium prior to the addition of the populations of T cells.

In some embodiments, the stimulating conditions include temperature suitable for the growth of human T lymphocytes, for example, at least about 25 degrees Celsius, generally at least about 30 degrees, and generally at or about 37 degrees Celsius. Optionally, the incubation may further comprise adding non-dividing EBV-transformed lymphoblastoid cells (LCL) as feeder cells. LCL can be irradiated with gamma rays in the range of about 6000 to 10,000 rads. The LCL feeder cells in some aspects is provided in any suitable amount, such as a ratio of LCL feeder cells to initial T lymphocytes of at least about 10:1.

Methods for Processing a Sample

In some embodiments, the methods include a method for processing an apheresis sample, comprising (a) shipping in a cooled environment to a storage facility an apheresis sample taken from a donor; and (b) cryogenically storing the apheresis sample at the storage facility. The methods may further include, according to certain embodiments, processing a plurality of apheresis samples, comprising (a) shipping in a cooled environment to a storage facility a plurality of apheresis samples, each taken from the same or from different donors, and shipped either at the same time or at different times; and (b) cryogenically storing each of the apheresis samples at the storage facility.

In some embodiments, the apheresis sample is blood collected from a donor according to embodiments described above.

In some embodiments, the temperature of the cooled shipping environment is from above −80° C. to 0° C. In some embodiments, the temperature of the cooled shipping environment is from above −80° C. to −20° C. In some embodiments, the temperature of the cooled shipping environment is from −20° C. to 0° C.

In some embodiments, the facility where the donor's apheresis sample is collected and the storage facility are affiliated with each other, but this is not required in all embodiments. In some embodiments, the facilities are affiliated with each other by way of the donor or another entity electing to have the apheresis sample collected at the collection facility and to have the apheresis sample stored at the storage facility. In some embodiments, the collection facility and the storage facility may share the same physical location. In some embodiments, the collection facility and the storage facility may be located in different locations, such as different nations or different states.

In some embodiments, the storage facility is a central or common repository storage facility, wherein apheresis samples of various patients obtained at different collection facilities are stored. In some embodiments, the central or common repository storage facility will cryogenically store the apheresis samples prior to sending these samples to one or more manufacturing facilities. In some embodiments the central or common repository facility and the manufacturing facilities are affiliated with each other. In some embodiments the central or common repository facility and the manufacturing facilities are not affiliated with each other. In some embodiments, all of the samples from a donor are sent to the manufacturing facility from the central or common repository facility. In other embodiments, some of the samples from a donor are sent to the manufacturing facility, and other samples are kept at the central or common repository facility. In some embodiments, all of the samples from a donor are sent to the same manufacturing facility from the central or common repository facility. In other embodiments, some of the samples from a donor are sent from the central or common repository facility to one manufacturing facility, and other samples from the donor are sent to another manufacturing facility.

In some embodiments, a type or types of cells are enriched and/or isolated from the apheresis sample prior to shipping. In other instances, the cells may be enriched and/or isolated from the apheresis sample after shipping. For example, the cells may be enriched and/or isolated according to the embodiments described above.

In some embodiments, the apheresis sample or the enriched and/or isolated cells are analyzed before being shipped. In some embodiments, the apheresis sample or the enriched and/or isolated cells are analyzed after being shipped and before being cryogenically stored. The apheresis sample or the enriched and/or isolated cells may be analyzed according to the embodiments described above.

In some embodiments, a portion or portions of the apheresis, or enriched and/or isolated cell population, or engineered T cell population or composition, is removed prior to the cryogenic freezing of the apheresis, or the enriched and/or isolated cell population, or engineered T cell population or composition. In some embodiments the portion or portions removed are analyzed at any point in time, including, for example, prior to or after cryogenic freezing of the apheresis, or the enriched and/or isolated cell population, or engineered T cell population or composition.

In some embodiments, the apheresis sample or the cells are combined with a freezing solution before being shipped. In some embodiments, the apheresis sample or the cells are combined with a freezing solution after being shipped and before being cryogenically stored. The freezing solution may be the same as the freezing solution in the embodiments described above.

In some embodiments, the apheresis sample is divided into 1, 2, 3, 4, 5, 6, 7, 8, 9, 10, or more than 10 separate containers prior to or after being combined with a freezing solution to be cryogenically frozen. In some embodiments, the apheresis sample is divided into 1, 2, 3, 4, 5, 6, 7, 8, 9, 10, or more than 10 separate containers prior to being shipped. In some embodiments, the apheresis sample is divided into 1, 2, 3, 4, 5, 6, 7, 8, 9, 10, or more than 10 separate containers after being shipped. In some embodiments any number of the separate containers carrying the divided apheresis are cryogenically frozen prior to or after being shipped.

In some embodiments the apheresis samples is divided into 1, 2, 3, 4, 5, 6, 7, 8, 9, 10, or more than 10 separate containers, which are cryogenically stored in a storage facility. In some embodiments the storage facility is a central or common repository storage facility. In some embodiments the storage facility sends any number of the separate containers carrying the divided apheresis to one or more manufacturing facilities.

In some embodiments, one or more containers, in which the apheresis sample has been cryogenically stored, are removed from cryogenic storage, while keeping the remaining containers in cryogenic storage. In some embodiments, the cells in the one or more containers removed from cryogenic storage are thawed. In some embodiments, the thawed cells are engineered. In some embodiments the thawed cells are engineered to express a CAR molecule. In some embodiments one or more subsequent containers, in which the apheresis sample has been cryogenically stored, are removed from cryogenic storage while keeping the remaining containers in cryogenic storage. In some embodiments, the cells in the one or more subsequent containers removed from cryogenic storage are thawed. In some embodiments, the thawed cells are engineered. In some embodiments the thawed cells are engineered to produce cells expressing a similar or different CAR molecule than the previously thawed cells. In some embodiments the containers in which the apheresis sample has been cryogenically stored are kept in cryogenic storage for different lengths of time.

In some embodiments, the apheresis sample or the cells are cooled to a temperature from above −80° C. to 0° C. before being shipped. The apheresis sample or the cells may be cooled in a manner according to the embodiments described above. In some embodiments, before the cooling of the cells, the cells are washed in a manner according to the embodiments described above.

In some embodiments, the apheresis sample or the cells are cryogenically frozen to a temperature from −210° C. to −80° C. before being shipped. In some embodiments, the apheresis sample or the cells are cryogenically frozen after being shipped. The apheresis sample or the cells may be cryogenically frozen in a manner according to the embodiments described above. In some embodiments, before the cryogenic freezing of the cells, the cells are washed in a manner according to the embodiments described above.

In some embodiments, the apheresis sample or the cells are cryogenically stored at a temperature from −210° C. to −80° C. For example, the apheresis sample or the cells may be cryogenically stored in a manner according to the embodiments described above, such as in the vapor phase of a liquid nitrogen storage tank, and such as for a storage period of from 1 day to 12 years. In some embodiments, the cells are stored, or banked, for a period of time greater than or equal to 12 hours, 24 hours, 36 hours, or 48 hours. In some embodiments, the cells are stored or banked for a period of time greater than or equal to 1 week, 2 weeks, 3 weeks, or 4 weeks. In some embodiments, the cells are placed into long-term storage or long-term banking. In some aspects, the cells are stored for a period of time greater than or equal to 1 month, 2 months, 3 months, 4 months, 5 months, 6 months, 7 months, 8 months, 9 months, 10 months, 11 months, 1 year, 2 years, 3 years, 4 years, 5 years, 6 years, 7 years, 8 years, 9 years, 10 years, 11 years, 12 years, 13 years, 14 years, 15 years, 16 years, 17 years, 18 years, 19 years, 20 years, 25 years, 30 years, 35 years, 40 years, or more.

In some embodiments, the apheresis sample or the cells are cryogenically stored at a temperature of −210° C. to −80° C. In some embodiments, the temperature in which the cells are stored does not go above about −100° C., or −95° C., or −90° C., or −85° C., or −80° C., or −75° C., or −70° C., or −65° C., or −60° C.

In some embodiments, after the storage period, the apheresis sample or the cells are thawed. For example, the apheresis sample or the cells may be thawed in a manner according to the embodiments described above. Also, according to certain embodiments, after the storage period, the percentage of viable cells is from 24% to 100%. The percentage of viable cells may be determined, for example, according to the embodiments described above.

In some embodiments, the apheresis sample or the enriched cells are analyzed after collection and before shipping. In some embodiments, the apheresis sample or the enriched cells are analyzed after shipping and before cryogenic storage. In some embodiments, the apheresis sample or the enriched cells are analyzed after the storage period. In some embodiments, after analysis, the apheresis sample or the cells may be modified. In some embodiments, the modification occurs before shipping. In some embodiments the modification occurs after shipping and before cryogenically storing. In some embodiments, the modification occurs after cryogenically storing. In such embodiments, the modification is termed "post-cryogenic modification." The analysis and/or modification of the apheresis sample or the cells may be performed according to the embodiments described above.

Compositions and Formulations

Also provided are compositions including the cells, including pharmaceutical compositions and formulations, such as unit dose form compositions including the number of cells for administration in a given dose or fraction thereof. The pharmaceutical compositions and formulations generally include one or more optional pharmaceutically acceptable carrier or excipient. In some embodiments, the composition includes at least one additional therapeutic agent.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

In some aspects, the choice of carrier is determined in part by the particular cell and/or by the method of administration. Accordingly, there are a variety of suitable formulations. For example, the pharmaceutical composition can contain preservatives. Suitable preservatives may include, for example, methylparaben, propylparaben, sodium benzoate, and benzalkonium chloride. In some aspects, a mixture of two or more preservatives is used. The preservative or mixtures thereof are typically present in an amount of about 0.0001% to about 2% by weight of the total composition. Carriers are described, e.g., by Remington's Pharmaceutical Sciences 16th edition, Osol, A. Ed. (1980). Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

Buffering agents in some aspects are included in the compositions. Suitable buffering agents include, for example, citric acid, sodium citrate, phosphoric acid, potassium phosphate, and various other acids and salts. In some aspects, a mixture of two or more buffering agents is used. The buffering agent or mixtures thereof are typically present in an amount of about 0.001% to about 4% by weight of the total composition. Methods for preparing administrable pharmaceutical compositions are known. Exemplary methods are described in more detail in, for example, Remington: The Science and Practice of Pharmacy, Lippincott Williams & Wilkins; 21st ed. (May 1, 2005).

The formulations can include aqueous solutions. The formulation or composition may also contain more than one active ingredient useful for the particular indication, disease, or condition being treated with the cells, preferably those with activities complementary to the cells, where the respective activities do not adversely affect one another. Such active ingredients are suitably present in combination in amounts that are effective for the purpose intended. Thus, in some embodiments, the pharmaceutical composition further includes other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, and/or vincristine.

In some embodiments, the composition includes the cells in an amount effective to reduce burden of the disease or condition, and/or in an amount that does not result in CRS or severe CRS in the subject and/or to effect any of the other outcomes of the methods as described herein.

The pharmaceutical composition in some embodiments contains the cells in amounts effective to treat or prevent the disease or condition, such as a therapeutically effective or prophylactically effective amount. Therapeutic or prophylactic efficacy in some embodiments is monitored by periodic assessment of treated subjects. The desired dosage can be delivered by a single bolus administration of the cells, by multiple bolus administrations of the cells, or by continuous infusion administration of the cells.

The cells and compositions may be administered using standard administration techniques, formulations, and/or devices. Administration of the cells can be autologous or heterologous. For example, immunoresponsive cells or progenitors can be obtained from one subject, and administered to the same subject or a different, compatible subject. Peripheral blood derived immunoresponsive cells or their progeny (e.g., in vivo, ex vivo or in vitro derived) can be administered via localized injection, including catheter administration, systemic injection, localized injection, intravenous injection, or parenteral administration. When administering a therapeutic composition (e.g., a pharmaceutical composition containing a genetically modified immunoresponsive cell), it will generally be formulated in a unit dosage injectable form (solution, suspension, emulsion).

Formulations include those for oral, intravenous, intraperitoneal, subcutaneous, pulmonary, transdermal, intramuscular, intranasal, buccal, sublingual, or suppository administration. In some embodiments, the cell populations are administered parenterally. The term "parenteral," as used herein, includes intravenous, intramuscular, subcutaneous, rectal, vaginal, and intraperitoneal administration. In some embodiments, the cells are administered to the subject using peripheral systemic delivery by intravenous, intraperitoneal, or subcutaneous injection.

Compositions in some embodiments are provided as sterile liquid preparations, e.g., isotonic aqueous solutions, suspensions, emulsions, dispersions, or viscous compositions, which may in some aspects be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyoi (for example, glycerol, propylene glycol, liquid polyethylene glycol) and suitable mixtures thereof.

Sterile injectable solutions can be prepared by incorporating the cells in a solvent, such as in admixture with a suitable carrier, diluent, or excipient such as sterile water, physiological saline, glucose, dextrose, or the like. The compositions can contain auxiliary substances such as wetting, dispersing, or emulsifying agents (e.g., methylcellulose), pH buffering agents, gelling or viscosity enhancing additives, preservatives, flavoring agents, and/or colors, depending upon the route of administration and the preparation desired. Standard texts may in some aspects be consulted to prepare suitable preparations.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, and sorbic acid. Prolonged absorption of the injectable pharmaceutical form can be brought about by the use of agents delaying absorption, for example, aluminum monostearate and gelatin.

The formulations to be used for in vivo administration are generally sterile. Sterility may be readily accomplished, e.g., by filtration through sterile filtration membranes.

In some embodiments, the therapeutic T cell composition comprises between about 10 million cells per ml and about 70 million cells per ml or between about 10 million viable cells per mL and about 70 million viable cells per mL. In some embodiments, the therapeutic T cell composition comprises between about 15 million cells or viable cells per ml and about 60 million cells or viable cells per ml. In some embodiments, the T cell composition comprises greater than 10 million cells or viable cells per ml. In some embodiments, the therapeutic T cell composition comprises greater than 15 million cells or greater than 15 million cells per ml.

In some embodiments, this application provides an article of manufacture comprising a container that comprises the therapeutic T cell composition. In some embodiments, the article further comprises information indicating that the container contains the target number of units of the therapeutic T cell composition. In some embodiments, the article comprises multiple containers, wherein each of the containers comprises a unit dose comprising the target number of units of the T cell composition. In some embodiments, the containers comprise between about 10 million cells or viable cells per mL and about 70 million cells or viable cells per mL, between about 15 million cells or viable cells and about 60 million cells or viable cells per mL, greater than 10 million cells or viable cells per mL, greater than 15 million cells or viable cells per mL, or a combination thereof. In some embodiments, the composition further comprises a cryoprotectant and/or the article further includes instructions for thawing the composition prior to administration to the subject.

In some embodiments, the cells are suspended in a freezing solution, e.g., following a washing step to remove plasma and platelets. Any of a variety of known freezing solutions and parameters in some aspects may be used. One example involves using PBS containing 20% DMSO and 8% HSA, or other suitable cell freezing media. This is then diluted 1:1 with media so that the final concentration of DMSO and HSA are 10% and 4%, respectively.

Any of a variety of known freezing solutions and parameters in some aspects may be used. In some embodiments, a cell sample can contain a cryopreservation or vitrification medium or solution containing the cryoprotectant. Suitable cryoprotectants include, but are not limited to, DMSO, glycerol, a glycol, a propylene glycol, an ethylene glycol, propanediol, polyethylene glycol (PEG), 1,2-propanediol (PROH) or a mixture thereof. In some examples, the cryopreservation solution can contain one or more non-cell permeating cryopreservative, including but not limited to, polyvinyl pyrrolidione, a hydroxyethyl starch, a polysaccharide, a monosaccharide, an alginate, trehalose, raffmose, dextran, human serum albumin, Ficoll, lipoproteins, polyvinyl pyrrolidone, hydroxyethyl starch, autologous plasma or a mixture thereof. In some embodiments, the cells are suspended in a freezing solution with a final concentration of cryoprotectant of between about 1% and about 20%, between about 3% and about 9%, or between about 6% and about 9% by volume. In certain embodiments, the final concentration of cryoprotectant in the freezing solution is about 3%, about 4%, about 5%, about 5.5%, about 6%, about 6.5%, about 7%, about 7.5%, about 8%, about 8.5%, about 9%, about 9.5%, or about 10% by volume.

In some embodiments, the cryoprotectant is DMSO. In particular embodiments, the cells are suspended in a freezing solution with a final concentration of DMSO of between about 1% and about 20%, between about 3% and about 9%, or between about 6% and about 9% by volume. In certain embodiments, the final concentration of DMSO in the freezing solution is about 3%, about 4%, about 5%, about 5.5%, about 6%, about 6.5%, about 7%, about 7.5%, about 8%, about 8.5%, about 9%, about 9.5%, or about 10% by volume.

In certain embodiments, the cells are suspended in a freezing solution at a density of between about $1\times10^6$ cells/ml and about $1\times10^8$ cells/mL, between about $1\times10^6$ cells/mL and about $2\times10^7$ cells/mL, between about $1\times10^7$ cells/mL and about $5\times10^7$ cells/mL, or between about $1\times10^7$ cells/mL to $5\times10^7$ cells/mL. In certain embodiments, the cells are suspended in the freezing solution at a density of about $1\times10^6$ cells/mL, about $2\times10^6$ cells/mL, about $5\times10^6$ cells/mL, about $1\times10^7$ cells/mL, about $1.5\times10^7$ cells/mL, about $2\times10^7$ cells/mL, about $2.5\times10^7$ cells/mL, about $2.5\times10^7$ cells/mL, about $2.5\times10^7$ cells/mL, about $3\times10^7$ cells/mL, about $3.5\times10^7$ cells/mL, about $4\times10^7$ cells/mL, about $4.5\times10^7$ cells/mL, or about $5\times10^7$ cells/mL. In certain embodiments, the cells are suspended in the freezing solution at a density of between about $1.5\times10^7$ cells/mL and about $6\times10^7$ cells/mL. In certain embodiments, the cells are suspended in the freezing solution at a density of between about $5\times10^6$ cells/mL and about $150\times10^6$ cells/mL. In certain embodiments, the cells are suspended in a freezing solution at a density of at least about $1\times10^7$ cells/mL. In particular embodiments, the cells are suspended in a freezing solution at a density of at least about $1.5\times10^7$ cells/mL. In some embodiments, the cells are viable cells.

In particular embodiments, the cells are suspended in a freezing solution at a density of between or between about $0.1\times10^6$ cells/mL and about $5{,}000\times10^6$ cells/mL, between or between about $1\times10^6$ cells/mL and about $500\times10^6$ cells/mL, between or between about $5\times10^6$ cells/mL and about $150\times10^6$ cells/mL, between or between about $10\times10^6$ cells/mL and about $70\times10^6$ cells/mL, or between or between about $15\times10^6$ cells/mL and about $60\times10^6$ cells/mL, each inclusive. In certain embodiments, the cells are suspended in a freezing solution at a density of between about $1\times10^6$ cells/mL and about $1\times10^8$ cells/mL, between about $1\times10^6$ cells/mL and about $2\times10^7$ cells/mL, between about $1\times10^7$ cells/mL and about $5\times10^7$ cells/mL, or between about $1\times10^7$ cells/mL to $5\times10^7$ cells/mL, each inclusive. In certain embodiments, the cells are suspended in the freezing solution at a density of about $1\times10^6$ cells/mL, about $2\times10^6$ cells/mL, about $5\times10^6$ cells/mL, about $1\times10^7$ cells/mL, about $1.5\times10^7$ cells/mL, about $2\times10^7$ cells/mL, about $2.5\times10^7$ cells/mL, about $2.5\times10^7$ cells/mL, about $2.5\times10^7$ cells/mL, about $3\times10^7$ cells/mL, about $3.5\times10^7$ cells/mL, about $4\times10^7$ cells/mL, about $4.5\times10^7$ cells/mL, or about $5\times10^7$ cells/mL. In certain embodiments, the cells are suspended in the freezing solution at a density of between about $1.5\times10^7$ cells/mL and about $6\times10^7$ cells/mL, inclusive. In certain embodiments, the cells are suspended in a freezing solution at a density of at least about $1\times10^7$ cells/mL. In particular embodiments, the cells are suspended in a freezing solution at a density of at least about $1.5\times10^7$ cells/mL. In some embodiments, the cells are viable cells.

In some embodiments, transfer to cryopreservation medium is associated with one or more processing steps that can involve washing of the sample, e.g., cells and/or engineered cell composition, such as to remove the media and/or replacing the cells in an appropriate cryopreservation buffer or media for subsequent freezing. In certain embodiments, the transfer to the cryopreservation medium is fully automated on a clinical-scale level in a closed and sterile system. In certain embodiments the transfer to the cryopreservation medium carried out using CliniMACS system (Miltenyi Biotec).

In some embodiments, the cells are frozen, e.g., cryopreserved, either before, during, or after said methods for processing and/or engineering the cells. In some embodiments, the freeze and subsequent thaw step removes granulocytes and, to some extent, monocytes in the cell population. The cells may be frozen to −80° C. at a rate of 1° per minute and stored in the vapor phase of a liquid nitrogen storage tank. In some embodiments, the composition is enclosed in a bag suitable for cryopreservation (for example, CryoMacs® Freezing Bags, Miltenyi Biotec). In some embodiments, the composition is enclosed in a vial suitable for cryopreservation (for example, CellSeal® Vials, Cook Regentec).

Suitable containers include, for example, bottles, vials, syringes, and flexible bags, such as infusion bags. In particular embodiments, the containers are bags, e.g., flexible bags, such as those suitable for infusion of cells to subjects, e.g., flexible plastic or PVC bags, and/or IV solution bags. The bags in some embodiments are sealable and/or able to be sterilized, so as to provide sterile solution and delivery of the cells and compositions. In some embodiments, the containers, e.g., bags, have a capacity of at or about or at least at or about 10, 20, 30, 40, 50, 60, 70, 80, 90, 100, 200, 300, 400, 500, or 1000 ml capacity, such as between at or about 10 and at or about 100 or between at or about 10 and at or about 500 ml capacity, each inclusive. In some embodiments, the containers, e.g., bags, are and/or are made from material which is stable and/or provide stable storage and/or maintenance of cells at one or more of various temperatures, such as in cold temperatures, e.g. below at or about or at or about −20° C., −80° C., −120° C., 135° C. and/or temperatures suitable for cryopreservation, and/or other temperatures, such as temperatures suitable for thawing the cells and body temperature such as at or about 37° C., for example, to permit thawing, e.g., at the subject's location or location of treatment, e.g., at bedside, immediately prior to treatment.

The containers may be formed from a variety of materials such as glass or plastic. In some embodiments, the container has one or more port, e.g., sterile access ports, for example, for connection of tubing or cannulation to one or more tubes, e.g., for intravenous or other infusion and/or for connection for purposes of transfer to and from other containers, such as cell culture and/or storage bags or other containers. Exemplary containers include infusion bags, intravenous solution bags, and vials, including those with stoppers pierceable by a needle for injection.

The present invention is not to be limited in scope by the embodiments disclosed herein, which are intended as single illustrations of individual aspects of the invention, and any that are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

Stimulatory Reagents

In some embodiments, incubating a composition of enriched cells under stimulating conditions is or includes incubating and/or contacting the composition of enriched cells with a stimulatory reagent that is capable of activating and/or expanding T cells. In some embodiments, the stimulatory reagent is capable of stimulating and/or activating one or more signals in the cells. In some embodiments, the one or more signals are mediated by a receptor. In particular embodiments, the one or more signals are or are associated with a change in signal transduction and/or a level or amount of secondary messengers, e.g., cAMP and/or intracellular calcium, a change in the amount, cellular localization, confirmation, phosphorylation, ubiquitination, and/or truncation of one or more cellular proteins, and/or a change in a cellular activity, e.g., transcription, translation, protein degradation, cellular morphology, activation state, and/or cell division. In particular embodiments, the stimulatory reagent activates and/or is capable of activating one or more intracellular signaling domains of one or more components of a TCR complex and/or one or more intracellular signaling domains of one or more costimulatory molecules.

In certain embodiments, the stimulatory reagent contains a particle, e.g., a bead, that is conjugated or linked to one or more agents, e.g., biomolecules, that are capable of activating and/or expanding cells, e.g., T cells. In some embodiments, the one or more agents are bound to a bead. In some embodiments, the bead is biocompatible, i.e., composed of a material that is suitable for biological use. In some embodiments, the beads are non-toxic to cultured cells, e.g., cultured T cells. In some embodiments, the beads may be any particles which are capable of attaching agents in a manner that permits an interaction between the agent and a cell.

In some embodiments, a stimulatory reagent contains one or more agents that are capable of activating and/or expanding cells, e.g., T cells, that are bound to or otherwise attached to a bead, for example to the surface of the bead. In certain embodiments, the bead is a non-cell particle. In particular embodiments, the bead may include a colloidal particle, a microsphere, nanoparticle, a magnetic bead, or the like. In some embodiments the beads are agarose beads. In certain embodiments, the beads are sepharose beads.

In particular embodiments, the stimulatory reagent contains beads that are monodisperse. In certain embodiments, beads that are monodisperse comprise size dispersions having a diameter standard deviation of less than 5% from each other.

In some embodiments, the bead contains one or more agents, such as an agent that is coupled, conjugated, or linked (directly or indirectly) to the surface of the bead. In some embodiments, an agent as contemplated herein can include, but is not limited to, RNA, DNA, proteins (e.g., enzymes), antigens, polyclonal antibodies, monoclonal antibodies, antibody fragments, carbohydrates, lipids lectins, or any other biomolecule with an affinity for a desired target. In some embodiments, the desired target is a T cell receptor and/or a component of a T cell receptor. In certain embodiments, the desired target is CD3. In certain embodiment, the desired target is a T cell costimulatory molecule, e.g., CD28, CD137 (4-1-BB), OX40, or ICOS. The one or more agents may be attached directly or indirectly to the bead by a variety of methods known and available in the art. The attachment may be covalent, noncovalent, electrostatic, or hydrophobic and may be accomplished by a variety of attachment means, including for example, a chemical means, a mechanical means, or an enzymatic means. In some embodiments, a biomolecule (e.g., a biotinylated anti-CD3 antibody) may be attached indirectly to the bead via another biomolecule (e.g., anti-biotin antibody) that is directly attached to the bead.

In some embodiments, the stimulatory reagent contains a bead and one or more agents that directly interact with a macromolecule on the surface of a cell. In certain embodiments, the bead (e.g., a paramagnetic bead) interacts with a cell via one or more agents (e.g., an antibody) specific for one or more macromolecules on the cell (e.g., one or more cell surface proteins). In certain embodiments, the bead (e.g., a paramagnetic bead) is labeled with a first agent described herein, such as a primary antibody (e.g., an anti-biotin antibody) or other biomolecule, and then a second agent, such as a secondary antibody (e.g., a biotinylated anti-CD3 antibody) or other second biomolecule (e.g., streptavidin), is added, whereby the secondary antibody or other second biomolecule specifically binds to such primary antibodies or other biomolecule on the particle.

In some embodiments, the stimulatory reagent contains one or more agents (e.g. antibody) that is attached to a bead (e.g., a paramagnetic bead) and specifically binds to one or more of the following macromolecules on a cell (e.g., a T cell): CD2, CD3, CD4, CD5, CD8, CD25, CD27, CD28, CD29, CD31, CD44, CD45RA, CD45RO, CD54 (ICAM-1), CD127, MHCI, MHCII, CTLA-4, ICOS, PD-1, OX40, CD27L (CD70), 4-1BB (CD137), 4-1BBL, CD30L, LIGHT, IL-2R, IL-12R, IL-1R, IL-15R; IFN-gammaR, TNF-alphaR, IL-4R, IL-10R, CD18/CDI Ia (LFA-1), CD62L (L-selectin), CD29/CD49d (VLA-4), Notch ligand (e.g. Delta-like 1/4, Jagged 1/2, etc.), CCR1, CCR2, CCR3, CCR4, CCR5, CCR7, and CXCR3 or fragment thereof including the corresponding ligands to these macromolecules or fragments thereof. In some embodiments, an agent (e.g. antibody) attached to the bead specifically binds to one or more of the following macromolecules on a cell (e.g. a T cell): CD28, CD62L, CCR7, CD27, CD127, CD3, CD4, CD8, CD45RA, and/or CD45RO.

In some embodiments, one or more of the agents attached to the bead is an antibody. The antibody can include a polyclonal antibody, monoclonal antibody (including full length antibodies which have an immunoglobulin Fc region), antibody compositions with polyepitopic specificity, multispecific antibodies (e.g., bispecific antibodies, diabodies, and single-chain molecules, as well as antibody fragments (e.g., Fab, F(ab')2, and Fv). In some embodiments, the stimulatory reagent is an antibody fragment (including antigen-binding fragment), e.g., a Fab, Fab'-SH, Fv, scFv, or (Fab')2 fragment. It will be appreciated that constant regions of any isotype can be used for the antibodies contemplated herein, including IgG, IgM, IgA, IgD, and IgE constant regions, and that such constant regions can be obtained from any human or animal species (e.g., murine species). In some embodiments, the agent is an antibody that binds to and/or recognizes one or more components of a T cell receptor. In particular embodiments, the agent is an anti-CD3 antibody. In certain embodiments, the agent is an antibody that binds to and/or recognizes a co-receptor. In some embodiments, the stimulatory reagent comprises an anti-CD28 antibody. In some embodiments, the bead has a diameter of greater than about 0.001 μm, greater than about 0.01 μm, greater than about 0.1 μm, greater than about 1.0 μm, greater than about 10 μm, greater than about 50 μm, greater than about 100 μm or greater than about 1000 μm and no more than about 1500 μm. In some embodiments, the bead has a diameter of about 1.0 μm to about 500 μm, about 1.0 μm to about 150 μm, about 1.0 μm to about 30 μm, about 1.0 μm to about 10 μm, about 1.0 μm to about 5.0 μm, about 2.0 μm to about 5.0 μm, or about 3.0 μm to about 5.0 μm. In some embodiments, the bead has a diameter of about 3 μm to about 5 μm. In some embodiments, the bead has a diameter of at least or at least about or about 0.001 μm, 0.01 μm, 0.1 μm, 0.5 μm, 1.0 μm, 1.5 μm, 2.0 μm, 2.5 μm, 3.0 μm, 3.5 μm, 4.0 μm, 4.5 μm, 5.0 μm, 5.5 μm, 6.0 μm, 6.5 μm, 7.0 μm, 7.5 μm, 8.0 μm, 8.5 μm, 9.0 μm, 9.5 μm, 10 μm, 12 μm, 14 μm, 16 μm, 18 μm or 20 μm. In certain embodiments, the bead has a diameter of or about 4.5 μm. In certain embodiments, the bead has a diameter of or about 2.8 μm.

In some embodiments, the beads have a density of greater than 0.001 g/cm$^3$, greater than 0.01 g/cm$^3$, greater than 0.05 g/cm$^3$, greater than 0.1 g/cm$^3$, greater than 0.5 g/cm$^3$, greater than 0.6 g/cm$^3$, greater than 0.7 g/cm$^3$, greater than 0.8 g/cm$^3$, greater than 0.9 g/cm$^3$, greater than 1 g/cm$^3$, greater than 1.1 g/cm$^3$, greater than 1.2 g/cm$^3$, greater than 1.3 g/cm$^3$, greater than 1.4 g/cm$^3$, greater than 1.5 g/cm$^3$, greater than 2 g/cm$^3$, greater than 3 g/cm$^3$, greater than 4 g/cm$^3$, or greater than 5 g/cm$^3$. In some embodiments, the beads have a density of between about 0.001 g/cm$^3$ and about 100 g/cm$^3$, about 0.01 g/cm$^3$ and about 50 g/cm$^3$, about 0.1 g/cm$^3$ and about 10 g/cm$^3$, about 0.1 g/cm$^3$ and about 0.5 g/cm$^3$, about 0.5 g/cm$^3$ and about 1 g/cm$^3$, about 0.5 g/cm$^3$ and about 1.5 g/cm$^3$, about 1 g/cm$^3$ and about 1.5 g/cm$^3$, about 1 g/cm$^3$ and about 2 g/cm$^3$, or about 1 g/cm$^3$ and about 5 g/cm$^3$. In some embodiments, the beads have a density of about 0.5 g/cm$^3$, about 0.5 g/cm$^3$, about 0.6 g/cm$^3$, about 0.7 g/cm$^3$, about 0.8 g/cm$^3$, about 0.9 g/cm$^3$, about 1.0 g/cm$^3$, about 1.1 g/cm$^3$, about 1.2 g/cm$^3$, about 1.3 g/cm$^3$, about 1.4 g/cm$^3$, about 1.5 g/cm$^3$, about 1.6 g/cm$^3$, about 1.7 g/cm$^3$, about 1.8 g/cm$^3$, about 1.9 g/cm$^3$, or about 2.0 g/cm$^3$. In certain embodiments, the beads have a density of about 1.6 g/cm$^3$. In particular embodiments, the beads or particles have a density of about 1.5 g/cm$^3$. In certain embodiments, the particles have a density of about 1.3 g/cm$^3$.

In certain embodiments, a plurality of the beads has a uniform density. In certain embodiments, a uniform density comprises a density standard deviation of less than 10%, less than 5%, or less than 1% of the mean bead density.

In some embodiments, the beads have a surface area of between about 0.001 $m^2$ per each gram of particles ($m^2/g$) to about 1,000 $m^2/g$, about 0.010 $m^2/g$ to about 100 $m^2/g$, about 0.1 $m^2/g$ to about 10 $m^2/g$, about 0.1 $m^2/g$ to about 1 $m^2/g$, about 1 $m^2/g$ to about 10 $m^2/g$, about 10 $m^2/g$ to about 100 $m^2/g$, about 0.5 $m^2/g$ to about 20 $m^2/g$, about 0.5 $m^2/g$ to about 5 $m^2/g$, or about 1 $m^2/g$ to about 4 $m^2/g$. In some embodiments, the particles or beads have a surface area of about 1 $m^2/g$ to about 4 $m^2/g$.

In some embodiments, the bead contains at least one material at or near the bead surface that can be coupled, linked, or conjugated to an agent. In some embodiments, the bead is surface functionalized, i.e. comprises functional groups that are capable of forming a covalent bond with a binding molecule, e.g., a polynucleotide or a polypeptide. In particular embodiments, the bead comprises surface-exposed carboxyl, amino, hydroxyl, tosyl, epoxy, and/or chloromethyl groups. In particular embodiments, the beads comprise surface exposed agarose and/or sepharose. In certain embodiments, the bead surface comprises attached stimulatory reagents that can bind or attach binding molecules. In particular embodiments, the biomolecules are polypeptides. In some embodiments, the beads comprise surface exposed protein A, protein G, or biotin.

In some embodiments, the bead reacts in a magnetic field. In some embodiments, the bead is a magnetic bead. In some embodiments, the magnetic bead is paramagnetic. In particular embodiments, the magnetic bead is superparamagnetic. In certain embodiments, the beads do not display any magnetic properties unless they are exposed to a magnetic field.

In particular embodiments, the bead comprises a magnetic core, a paramagnetic core, or a superparamagnetic core. In some embodiments, the magnetic core contains a metal. In some embodiments, the metal can be, but is not limited to, iron, nickel, copper, cobalt, gadolinium, manganese, tantalum, zinc, zirconium or any combinations thereof. In certain embodiments, the magnetic core comprises metal oxides (e.g., iron oxides), ferrites (e.g., manganese ferrites, cobalt ferrites, nickel ferrites, etc.), hematite and metal alloys (e.g., CoTaZn). In some embodiments, the magnetic core comprises one or more of a ferrite, a metal, a metal alloy, an iron oxide, or chromium dioxide. In some embodiments, the magnetic core comprises elemental iron or a compound thereof. In some embodiments, the magnetic core comprises one or more of magnetite (Fe3O4), maghemite (γFe2O3), or greigite (Fe3S4). In some embodiments, the inner core comprises an iron oxide (e.g., $Fe_3O_4$).

In certain embodiments, the bead contains a magnetic, paramagnetic, and/or superparamagnetic core that is covered by a surface functionalized coat or coating. In some embodiments, the coat can contain a material that can include, but is not limited to, a polymer, a polysaccharide, a silica, a fatty acid, a protein, a carbon, agarose, sepharose, or a combination thereof. In some embodiments, the polymer can be a polyethylene glycol, poly (lactic-co-glycolic acid), polyglutaraldehyde, polyurethane, polystyrene, or a polyvinyl alcohol. In certain embodiments, the outer coat or coating comprises polystyrene. In particular embodiments, the outer coating is surface functionalized.

In some embodiments, the stimulatory reagent comprises a bead that contains a metal oxide core (e.g., an iron oxide core) and a coat, wherein the metal oxide core comprises at least one polysaccharide (e.g., dextran), and wherein the coat comprises at least one polysaccharide (e.g., amino dextran), at least one polymer (e.g., polyurethane) and silica. In some embodiments the metal oxide core is a colloidal iron oxide core. In certain embodiments, the one or more agents include an antibody or antigen-binding fragment thereof. In particular embodiments, the one or more agents include an anti-CD3 antibody and an anti-CD28 antibody. In some embodiments, the stimulatory reagent comprises an anti-CD3 antibody, anti-CD28 antibody, and an anti-biotin antibody. In some embodiments, the stimulatory reagent comprises an anti-biotin antibody. In some embodiments, the bead has a diameter of about 3 μm to about 10 μm. In some embodiments, the bead has a diameter of about 3 μm to about 5 μm. In certain embodiments, the bead has a diameter of about 3.5 μm.

In some embodiments, the stimulatory reagent comprises one or more agents that are attached to a bead comprising a metal oxide core (e.g., an iron oxide inner core) and a coat (e.g., a protective coat), wherein the coat comprises polystyrene. In certain embodiments, the beads are monodisperse, paramagnetic (e.g., superparamagnetic) beads comprising a paramagnetic (e.g., superparamagnetic) iron core, e.g., a core comprising magnetite ($Fe_3O_4$) and/or maghemite ($\gamma Fe_2O_3$) c and a polystyrene coat or coating. In some embodiments, the bead is non-porous. In some embodiments, the beads contain a functionalized surface to which the one or more agents are attached. In certain embodiments, the one or more agents are covalently bound to the beads at the surface. In some embodiments, the one or more agents include an antibody or antigen-binding fragment thereof. In some embodiments, the one or more agents include an anti-CD3 antibody and an anti-CD28 antibody. In some embodiments, the one or more agents include an anti-CD3 antibody and/or an anti-CD28 antibody, and an antibody or antigen fragment thereof capable of binding to a labeled antibody (e.g., biotinylated antibody), such as a labeled anti-CD3 or anti-CD28 antibody. In certain embodiments, the beads have a density of about 1.5 $g/cm^3$ and a surface area of about 1 $m^2/g$ to about 4 $m^2/g$. In particular embodiments; the beads are monodisperse superparamagnetic beads that have a diameter of about 4.5 μm and a density of about 1.5 $g/cm^3$. In some embodiments, the beads the beads are monodisperse superparamagnetic beads that have a mean diameter of about 2.8 μm and a density of about 1.3 $g/cm^3$.

In some embodiments, the composition of enriched T cells is incubated with stimulatory reagent a ratio of beads to cells at or at about 3:1, 2.5:1, 2:1, 1.5:1, 1.25:1, 1.2:1, 1.1:1, 1:1, 0.9:1, 0.8:1, 0.75:1, 0.67:1, 0.5:1, 0.3:1, or 0.2:1. In particular embodiments, the ratio of beads to cells is between 2.5:1 and 0.2:1, between 2:1 and 0.5:1, between 1.5:1 and 0.75:1, between 1.25:1 and 0.8:1, between 1.1:1 and 0.9:1. In particular embodiments, the ratio of stimulatory reagent to cells is about 1:1 or is 1:1.

Removal of the Stimulatory Reagent from Cells

In certain embodiments, the stimulatory reagent is removed and/or separated from the cells. Without wishing to be bound by theory, particular embodiments contemplate that the binding and/or association between a stimulatory reagent and cells may, in some circumstances, be reduced over time during the incubation. In certain embodiments, one or more agents may be added to reduce the binding and/or association between the stimulatory reagent and the cells. In particular embodiments, a change in cell culture conditions, e.g., media temperature of pH, may reduce the binding and/or association between the stimulatory reagent and the cells. Thus, in some embodiments, the stimulatory reagent may be removed from an incubation, cell culture system, and/or a solution separately from the cells, e.g., without removing the cells from the incubation, cell culture system, and/or a solution as well.

Methods for removing stimulatory reagents (e.g. stimulatory reagents that are or contain particles such as bead particles or magnetizable particles) from cells are known. In some embodiments, the use of competing antibodies, such as non-labeled antibodies, can be used, which, for example, bind to a primary antibody of the stimulatory reagent and alter its affinity for its antigen on the cell, thereby permitting for gentle detachment. In some cases, after detachment, the competing antibodies may remain associated with the particle (e.g. bead particle) while the unreacted antibody is or may be washed away and the cell is free of isolating, selecting, enriching and/or activating antibody. Exemplary of such a reagent is DETACaBEAD (Friedl et al. 1995; Entschladen et al. 1997). In some embodiments, particles (e.g. bead particles) can be removed in the presence of a cleavable linker (e.g. DNA linker), whereby the particle-bound antibodies are conjugated to the linker (e.g. CELLection, Dynal). In some cases, the linker region provides a cleavable site to remove the particles (e.g. bead particles) from the cells after isolation, for example, by the addition of DNase or other releasing buffer. In some embodiments, other enzymatic methods can also be employed for release of a particle (e.g. bead particle) from cells. In some embodiments, the particles (e.g. bead particles or magnetizable particles) are biodegradable.

In some embodiments, the stimulatory reagent is magnetic, paramagnetic, and/or superparamagnetic, and/or contains a bead that is magnetic, paramagnetic, and/or superparamagnetic, and the stimulatory reagent may be removed from the cells by exposing the cells to a magnetic field. Examples of suitable equipment containing magnets for generating the magnetic field include DynaMag CTS (Thermo Fisher), Magnetic Separator (Takara) and EasySep Magnet (Stem Cell Technologies).

In particular embodiments, the stimulatory reagent is removed or separated from the cells prior to harvesting, collecting, and/or formulating engineered cells produced by the methods provided herein. In some embodiments, the stimulatory reagent is removed and/or separated from the cells prior to engineering, e.g., transducing or transfecting, the cells. In particular embodiments, the stimulatory reagent is removed and/or separated from the cells after the step of engineering the cells. In certain embodiments, the stimulatory reagent is removed prior to the cultivation of the cells, e.g., prior to the cultivation of the engineered, e.g., transfected or transduced, cells under conditions to promote proliferation and/or expansion.

EXAMPLES

In order to assess the effects of cryopreserving apheresis, prior to the selection or isolation of a cell population of interest, apheresis samples were taken through various steps of a process designed to produce engineered T cells. Samples were assessed at various points for cell viability, cell number yield, cell phenotypes, and cell activity. These studies were designed to determine whether cryopreservation of apheresis material (1) influenced the phenotypic proportions of relevant CD4+ and CD8+ T-cell populations, (2) impacted the ability to sort and select relevant T-cell populations post-thaw, and/or (3) influenced cell health, and/or functionality, In the following examples apheresis refers to the apheresis collected from a donor. Cryopreserved apheresis refers to the cell product resulting from the cryopreservation of the apheresis sample after collection but prior to the selection of any cell population of interest within the sample. Rested apheresis refers to the cell product resulting from a step in which after the cryopreserved apheresis was thawed, it was allowed to rest for a determined amount of time prior to any further processing steps. Cryopreserved selected material refers to the cell product resulting from a step in which after cells of interest (CD4+ and CD8+ T cells in these examples) were isolated, they underwent a cryopreservation step, post-isolation.

Example 1: Processes for Generating Therapeutic Compositions of CD4+ and CD8+ Cells Expressing an Anti-CD19 CAR Engineered CD4+ T cells and engineered CD8+ T cells each expressing the same anti-CD19 chimeric antigen receptor (CAR) were produced by a process as generally outlined herein. As described in Example 2 below, cells were either produced by a process wherein separate compositions of CD4+ and CD8+ cells were selected from isolated PBMCs from human leukapheresis samples and cryofrozen. The selected CD4+ and CD8+ compositions were subsequently thawed and separately underwent steps for stimulation, transduction, and expansion. A second exemplary process involved an additional cryopreservation step before the selection step.

The isolated CD4+ and CD8+ cells were separately stimulated in the presence of paramagnetic polystyrene-coated beads with attached anti-CD3 and anti-CD28 antibodies at a 1:1 bead to cell ratio. The cells were stimulated in media containing IL-2, IL-15, and N-Acetyl Cysteine (NAC). The CD4+ cell media also included IL-7.

Following the introduction of the beads, CD4+ and CD8+ cells were separately transduced with a lentiviral vector encoding the same anti-CD19 CAR. The CAR contained an anti-CD19 scFv derived from a murine antibody, an immunoglobulin spacer, a transmembrane domain derived from CD28, a costimulatory region derived from 4-1BB, and a CD3-zeta intracellular signaling domain.

After transduction, the beads were removed from the cell compositions by exposure to a magnetic field. CD4+ and CD8+ cells were then separately cultivated for expansion with continual mixing and oxygen transfer by a bioreactor (Xuri W25 Bioreactor). Poloxamer was added to the media. Both cell compositions were cultivated in the presence of IL-2 and IL-15. The CD4+ cell media also included IL-7. The CD4+ and CD8+ cells were each cultivated, prior to harvest, to a desired cell number and/or concentration. One day after reaching the threshold, cells from each composition were separately harvested, formulated, and cryofrozen.

A controlled rate freezer utilizing a step-wise freezing profile was used for the cryopreservation steps described in the examples below.

Example 2. Study Design

Two healthy donors (i.e., Donor 1 and Donor 2) were used for this study, and the initial incoming apheresis (APH) material was split into five different arms for each donor. One fifth of the incoming apheresis volume (the control arms or Arms 5 and 10) was washed and subjected to an isolation step, to isolate CD4+ and CD8+ T cells, at which point the selected cells were cryopreserved for 2 weeks. The remaining apheresis from each donor was split into 4 samples before being cryopreserved (Arms 1-4 and arms 6-9). Each cryopreserved sample was thawed, washed, and either rested for two hours at 37° C. followed by selection or were subjected to a selection step immediately after thawing and washing. Half of the arms were frozen post-selection and the other half were processed forward directly to activation.

Samples in arms 1, 2, 6, and 7 were cryopreserved for 2 weeks prior to the cells being thawed to undergo isolation of CD4+ and CD8+ T cell populations and subjected to cell activation methods. Arms 1 and 6 included an extra step, a rest step, wherein after being thawed, cells were allowed to rest for 2 hours in an incubator prior to any further processing. Samples in arms 3, 4, 8 and 9 were cryopreserved for 2-4 days prior to being thawed to undergo selection of CD4+ and CD8+ T cell populations, at which point the selected populations were cryopreserved for 1 week prior to the cells being thawed and subsequently subjected to stimulation. Arms 3 and 8 included an extra step, a rest step, wherein after being thawed, cells were allowed to rest for 2 hours in an incubator prior to any further processing.

The cells were taken through various processing steps including a selection step, which isolated CD4+ and CD8+ T cells. At this selection step, each arm was divided into sub-arms (i.e., CD4+ and CD8+ T cell sub-arms), at which point the selected cells proceeded through the remaining processing steps. Table 1 shows the study design, including the cryopreservation steps each arm underwent.

TABLE 1

Study Design

| Arm | Cryopreservation of apheresis (pre-isolation) | Rest step | Cryopreservation post-isolation | Donor |
|---|---|---|---|---|
| 1 | Yes | Yes | No | 1 |
| 2 | Yes | No | No | 1 |
| 3 | Yes | Yes | Yes | 1 |
| 4 | Yes | No | Yes | 1 |
| 5 | No | No | Yes | 1 |
| 6 | Yes | Yes | No | 2 |
| 7 | Yes | No | No | 2 |
| 8 | Yes | Yes | Yes | 2 |
| 9 | Yes | No | Yes | 2 |
| 10 | No | No | Yes | 2 |

Example 3: Cryopreservation of Apheresis Material does not Meaningfully Impact Cell Phenotype Flow analysis was performed pre- and post-cryopreservation of apheresis samples to evaluate the impact of freezing on the distribution of cells of different phenotypes. A custom flow panel was developed to assess the distribution of T cells, B cells, NK cells, NK-T cells, monocytes, dendritic cells, and memory T cell phenotypes. Results suggest that the distribution of cells of different phenotypes was equivalent between pre- and post-cryopreservation samples.

Both cryopreserved apheresis and fresh apheresis samples were analyzed for the presence of CD4 and CD8 molecules on the cell surface using flow cytometry. The results of this assay demonstrated that the level of surface CD4 and CD8 molecules is not affected by cryopreservation. These results also suggest that the cryopreservation of the apheresis did not affect the relative proportion of CD4+ and CD8+ T cells in the samples as the percentages of these cells were comparable pre- and post-cryogenic freezing for both donors.

Example 4: Impact of Cryopreservation on the Isolation of CD4+ and/or CD8+ T Cell Populations In order to further assess whether cryopreserving apheresis affects the processing of CD4+ and CD8+ T cells, a viability assay was performed at various steps leading to the selection of the cells of interest. Cell viability was assessed for cells subjected to cryopreservation before the selection step, without a rest period post-cryopreservation, (Arms 2, 4, 7, and 9), cells subjected to cryopreservation before the selection step, with a rest period post-cryopreservation, (Arms 1, 3, 6, and 8), and cells subjected to cryopreservation after the isolation step, (Arms 5 and 10, or control arms) at various steps of a process. Specifically, viability was evaluated after apheresis was collected; after apheresis was formulated for cryopreservation; after apheresis was cryopreserved for a determined period of time, followed by being thawed and diluted; after the diluted thawed apheresis was washed; after the washed apheresis was rested for 2 hrs in an incubator; after antibody-coated beads were added to the sample; and after CD8+ and/or CD4+ T cells were isolated. Cell viability values across all arms was comparable with the cell viability values for the control arms at each processing step.

Total nucleated cell counts (TNC) were also determined for all samples during the various steps leading to the isolation of CD4+ and/or CD8+ T cells. Cell losses were mostly found to occur during the formulation step. Cell yield ratios obtained by normalizing the post-isolation cell number values to the pre-isolation cell number values demonstrated that cell losses in the cryopreserved apheresis samples occurred prior to the isolation of CD4+ and CD8+ T cell populations, and that the step to step cell yield within the isolation process was not impacted. However, in this experiment, the final TNC values corresponding to selected cells were found to be slightly different between some cryopreserved apheresis arms and control arms of each cell type for each donor, possibly due to cell losses occurring pre-isolation. However, the CD4+ T cell yield for one donor was found to be comparable between cryopreserved apheresis and the control arm.

Example 5: Assessing Cell Phenotype and Viability after the Isolation and Freeze Steps After the isolation steps, cells which required a cryopreservation step (Arms 3, 4, 5, 8, 9, and 10) were cryopreserved and then thawed for further analysis. Cells in arms 3, 4, 8, and 9 were cryogenically stored for 1.5 to 2 weeks prior to being thawed for further analysis and processing. Cells in arms 5 and 10 (or control arms) were cryogenically stored for 2 weeks prior to be being thawed for further analysis and processing. Assays were performed at this point for all isolated T cell populations obtained from all arms of each donor prior to any cell activation steps. The TMEM assay assessed the presence of various T cell markers across the selected cell populations from the different arms of each donor. The cell phenotype distribution (based on detection of selected markers) did not vary greatly between cryopreserved apheresis arms and control arms of each cell type for each donor. Cells in arms which did not undergo a post-isolation freeze step trended towards naïve-like cells (CD45RA+/CCR7+, CD27+/CD28+) with fewer terminal effector cells (CD45RA+, CCR7−). CD62L was slightly reduced for samples subjected to the post-isolation freezing step.

Cell viability was assessed for all arms of each cell type from each donor prior to cell activation. Cell viability did not vary greatly between the cryopreserved apheresis and control arms of each cell type from each donor. Additionally, in order to assess the effects of the post-isolation freezing step, cell yield ratios were obtained by normalizing cell numbers obtained after the post-isolation freezing step to the cell numbers obtained right after isolation, pre-freezing. Cell yield ratios were similar between cryopreserved apheresis and control arms.

Levels of Caspase 3 was found to be low (less than or about 5%) across all arms.

Example 6: Assessing Cell Viability and Cell Yield During Activation, Transduction, and Expansion As previously discussed, after the isolation step, the arms of the study which needed to undergo a post-isolation freeze step were cryogenically stored for a determined amount of time before they were thawed and continued through activation, transduction and expansion steps. Cell viability and TNC values were determined after the cryopreserved material was thawed; after the thawed material was stimulated in the presence of paramagnetic polystyrene-coated beads with attached anti-CD3 and anti-CD28 antibodies; after the activated cells underwent transduction; after beads were removed from the cells; and after the cells were expanded for 2 or 3 days. Cell viability was found to be comparable between cryopreserved apheresis and control arms of each cell type for each donor. At the stimulation step, the cell viability values for cryopreserved apheresis arms showed less than a 20% difference compared to the values for their corresponding control arms. This percent difference was lower than 10% at all the other steps. Additionally, the TNC values obtained at each of these steps were equivalent between cryopreserved apheresis arms and their corresponding control arms. Moreover, the fold expansion calculated at each step was also found to be equivalent between cryopreserved apheresis arms and their corresponding control arms.

These results indicate that in this experiment, cryopreserved apheresis samples, without a rest or further cryopreservation step immediately post-isolation and cryopreserved apheresis samples, with a rest step, but no further cryopreservation step immediately post-isolation, have similar or higher final cell yields compared to their corresponding control arms.

Example 7: Assessing Cell Viability, Cell Yield, and Cell Activity During Formulation of a Cryopreserved Composition Cells from each arm, obtained after the expansion step, were formulated in cryopreservation media and frozen. Samples were then thawed for further analysis. Cell viability and cell yield values were determined for cells in all arms of the study at this step. The average viability and cell number yield was equivalent between cryopreserved apheresis arms and their corresponding control arms at this step.

Assays were also performed to assess the cell phenotype distribution for all arms. Cell phenotypes were found to be statistically equivalent between cryopreserved apheresis arms and their corresponding control arms. Arms that had not undergone a post-isolation freeze step tended to contain a greater percentage of CD45RA+/CCR7+ and CD27+/CD28+ cells, and fewer CD45RA+, CCR7-cells. Additionally, in this experiment, the levels of Caspase 3 were found to be slightly higher for CD8+ T cell arms in comparison to CD4+ T cell arms, with arms that included a post-isolation freeze step displaying a higher caspase level than arms which did not include this step.

Interferon Gamma (IFNγ) secretion was used to assess T cell functionality post-processing. T cells from each arm were stimulated to produce IFNγ. After stimulation supernatants were collected and secreted IFNγ in the supernatant was measured. The values for all experimental conditions were consistent with the values for their corresponding controls, demonstrating that the cell activity of the final cell product was not affected by the early cryopreservation step.

A cytolytic assay was also performed to evaluate the cytolytic activity of the produced CD8+ T cells. Cytolytic activity was measured at various Effector cell: Target cell ratios to determine the EC50 (the ratio required to kill 50% of target cells). The cytolytic EC50 fold difference between cryopreserved apheresis arms in comparison to their corresponding control arms was found to be lower than a 2-fold difference, suggesting that the different arm conditions did not meaningfully change the cytolytic EC50 of the resulting cells.

EXEMPLARY EMBODIMENTS

1. A method comprising: cryogenically storing cells from a biological sample derived from a donor, wherein the cells have been obtained from the donor at a point in time that is (i) after the donor is diagnosed with a disease or condition, and before the donor has received one or more of the following: any initial treatment for the disease or condition, any targeted treatment or any treatment labeled for treatment for the disease or condition, or any treatment other than radiation and/or chemotherapy, (ii) after a first relapse, in the donor, of the disease or condition following initial treatment for the disease or condition, and before the donor receives post-relapse treatment for the disease or condition, or (iii) a time at which the donor has not been diagnosed with, or is not known to or is not suspected of having, the disease or condition.
2. The method of embodiment 1, wherein the biological sample is or is derived from a blood sample of the donor.
3. The method of embodiment 1 or embodiment 2, wherein the cells have not been subjected to a selection step for, and/or have not been enriched for, a blood cell population and/or a T cell population and/or a T cell subset, before being cryogenically stored.
4. The method of embodiment 1 or embodiment 2, wherein the cells have been subjected to a selection step and/or enrichment for a blood cell and/or T cell population before being cryogenically stored, optionally wherein the method further comprises selecting or enriching for the cell population from the biological sample prior to said cryogenic storage.
5. The method of embodiment 4, wherein the selection step and/or enrichment comprises an immunoaffinity-based selection and/or comprises positive or negative selection.
6. The method of any of embodiments 2-5, wherein: the selection step and/or enrichment comprises enrichment and/or isolation of $CD4^+$ cells or a subset thereof and/or CD8+ cells or a subset thereof, wherein enrichment or isolation of the $CD4^+$ cells or subset thereof is carried out either separately or in combination with the selection and/or isolation of the $CD8^+$ cells or subset thereof, optionally wherein the subset of $CD8^+$ cells and/or the subset of $CD4^+$ Cells optionally is selected from the group consisting of memory cells, central memory T ($T_{CM}$) cells, effector memory cells ($T_{EM}$), stem central memory ($T_{SCM}$) cells, T effector ($T_E$) cells, effector memory RA T ($T_{EMRA}$) cells, naïve T (TN) cells and/or regulatory T ($T_{REG}$) cells.

7. The method of any one of embodiments 1-6, wherein the cells comprise or are enriched for T cells.
8. The method of embodiment 7, wherein the T cells comprise or are enriched for $CD4^+$ T cells or a subset thereof, $CD8^+$ T cells or a subset thereof, or a mixture thereof, wherein the subset of $CD8^+$ cells and/or the subset of $CD4^+$ Cells optionally is selected from the group consisting of memory cells, central memory T ($T_{CM}$) cells, effector memory cells ($T_{EM}$), stem central memory ($T_{SCM}$) cells, T effector ($T_E$) cells, effector memory RA T ($T_{EMRA}$) cells, naïve T (TN) cells and/or regulatory T ($T_{REG}$) cells.
9. The method of any one of embodiments 1-8, further comprising, prior to cryogenically storing the cells: cooling the cells to a temperature less than or equal to 0° C.
10. The method of embodiment 8, further comprising, prior to storing and/or prior to cooling the cells: combining the cells with a freezing solution.
11. The method of embodiment 10, wherein the freezing solution comprises about 10% dimethyl sulfoxide (DMSO) and a serum protein, optionally human serum albumin, optionally about 4% human serum albumin, and/or wherein the freezing solution comprises and/or the final concentration of the composition in which the cells are cryopreserved and stored comprises between about 1% and about 20%, between about 3% and about 9%, or between about 6% and about 9% by volume DMSO and/or comprises about 3%, about 4%, about 5%, about 5.5%, about 6%, about 6.5%, about 7%, about 7.5%, about 8%, about 8.5%, about 9%, about 9.5%, or about 10% by volume DMSO.
12. The method of any one of embodiments 9-11, wherein cooling the cells comprises lowering the temperature at a rate of at or about 1° C. per minute, optionally until the temperature reaches at or about −80° C.
13. The method of any one of embodiments 1-11, wherein the cells are cryogenically stored in a container placed in a vapor phase of liquid nitrogen, wherein the container is optionally a bag or vial suitable for cryopreservation.
14. The method of any one of embodiments 1-13, wherein the cells are cryogenically stored for a period of time greater than or equal to 12 hours, 24 hours, 36 hours, 48 hours, 1 week, 2 weeks, 3 weeks, or 4 weeks, 1 month, 2 months, 3 months, 4 months, 5 months, 6 months, 7 months, 8 months, 9 months, 10 months, 11 months, 1 year, 2 years, 3 years, 4 years, 5 years, 6 years, 7 years, 8 years, 9 years, 10 years, 11 years, 12 years, 13 years, 14 years, 15 years, 16 years, 17 years, 18 years, 19 years, 20 years, 25 years, 30 years, 35 years, or 40 years.
15. The method of any of embodiments 1-14, wherein the cells are stored for a period of time and wherein, after the period of time, the percentage of viable cells or viable T cells or subtype or subset thereof in the composition is from about 24% to about 100% or is at least about 15, 20, 25, 30, 35, 40, 45, 50, 55, 60, 65, 70, 75, 80, 85, or 90%.
16. The method of any one of embodiments 1-15, wherein the disease is a cancer, an inflammatory disease or condition, an autoimmune disease or condition, or an infectious disease or condition.
17. The method of embodiment 16, wherein the cancer is chronic lymphocytic leukemia, acute lymphocytic leukemia, pro-lymphocytic leukemia, hairy cell leukemia, acute lymphocytic leukemia, null-acute lymphoblastic leukemia, Hodgkin's lymphoma, non-Hodgkin's lymphoma, diffuse large B cell lymphoma, multiple myeloma, follicular lymphoma, splenic, marginal zone lymphoma, mantle cell lymphoma, indolent B cell lymphoma, or acute myeloid leukemia.
18. The method of embodiment 16 or 17, wherein the cancer comprises cells expressing at least one of ROR1, EGFR, Her2, L1-CAM, CD19, CD20, CD22, mesothelin, CEA, and hepatitis B surface antigen, anti-folate receptor, CD23, CD24, CD30, CD33, CD38, CD44, EGFR, EGP-2, EGP-4, EPHa2, ErbB2, 3, or 4, FBP, fetal acethycholine receptor, GD2, GD3, HMW-MAA, IL-22R-alpha, IL-13R-alpha2, kdr, kappa light chain, Lewis Y, L1-cell adhesion molecule, MAGE-A1, MUC1, MUC16, B cell maturation antigen (BCMA), FCRL5/FCRH5, GPRC5D, PSCA, NKG2D Ligands, NY-ESO-1, MART-1, gp100, oncofetal antigen, TAG72, VEGF-R2, carcinoembryonic antigen (CEA), prostate specific antigen, PSMA, Her2/neu, estrogen receptor, progesterone receptor, ephrinB2, CD123, CS-1, c-Met, GD-2, and MAGE A3, CE7, Wilms Tumor 1 (WT-1), and a cyclin, such as cyclin A1 (CCNA1).
19. The method of any one of embodiments 1-18, wherein the initial treatment or the subsequent treatment is chemotherapy, radiation and/or surgery and/or is a debulking treatment.
20. The method of embodiment 19, wherein the initial treatment or the subsequent treatment is or comprises combination chemotherapy.
21. The method of any one of embodiments 1-20, wherein the donor is human.
22. The method of any one of embodiments 1-21, further comprising analyzing the cells before cryogenic storage, optionally by assessing surface expression of the cells for one or more phenotypic markers.
23. The method of any one of embodiments 1-21, further comprising thawing the cryogenically stored cells.
24. The method of embodiment 23, further comprising performing post-cryogenic modification to increase an activity of the cells.
25. The method of embodiment 24, wherein the post-cryogenic modification is based on analyzing the cells before cryogenic storage.
26. The method of any of embodiments 23-25, further comprising, following cryogenic storage and/or thawing of the cells, engineering the cells to express a recombinant or exogenous molecule, which optionally is a recombinant protein, optionally a recombinant receptor, which optionally is or comprises a T cell receptor (TCR), a chimeric receptor, and/or a chimeric antigen receptor.
27. The method of embodiment 26, wherein the recombinant molecule is a recombinant receptor that specifically recognizes or binds to an antigen expressed by, specifically expressed by, or associated with, the disease or condition.
28. The method of any one of embodiments 1-26, wherein the number of the cells, when collected from the donor, and/or total in the apheresis sample, is at or about or is no more than at or about $500\times10^6$, $1000\times10^6$, $2000\times10^6$, $3000\times10^6$, $4000\times10^6$, or $5000\times10^6$ or more total cells or total nucleated cells.
29. A method for processing an apheresis sample, comprising: (a) shipping in a cooled environment to a storage facility the apheresis sample obtained from a donor; and (b) cryogenically storing the apheresis sample, optionally at the storage facility.

30. The method of embodiment 29, further comprising enriching T cells from the apheresis sample prior to shipping and/or prior to cryogenically storing the sample.

31. The method of embodiment 30, wherein the T cells are or comprise or are enriched for $CD4^+$ T cells or a subset thereof, $CD8^+$ T cells or a subset thereof, or a mixture thereof, optionally wherein the subset of $CD8^+$ cells and/or the subset of $CD4^+$ Cells optionally is selected from the group consisting of memory cells, central memory T ($T_{CM}$) cells, effector memory cells ($T_{EM}$), stem central memory ($T_{SCM}$) cells, T effector ($T_E$) cells, effector memory RA T ($T_{EMRA}$) cells, naïve T (TN) cells and/or regulatory T ($T_{REG}$) cells and/or wherein the sample is enriched for bulk T cells.

32. The method of any one of embodiments 29-31, further comprising analyzing the apheresis sample prior to shipping.

33. The method of any one of embodiments 29-32, further comprising adding a freezing solution to the apheresis sample prior to shipping.

34. The method of embodiment 32, further comprising adding a freezing solution to the apheresis sample prior to shipping, wherein the freezing solution is selected based on the analyzing of the apheresis sample prior to shipping.

35. The method of any one of embodiments 29-34, further comprising cryogenically freezing the apheresis sample prior to shipping.

36. The method of embodiment 35, further comprising enriching T cells from the apheresis sample after shipping and before cryogenically storing the cells.

37. The method of embodiment 36, wherein the T cells are or comprise or are enriched for $CD4^+$ T cells or subset thereof, $CD8^+$ T cells or subset thereof, or a mixture thereof, optionally wherein the subset of $CD8^+$ cells and/or the subset of $CD4^+$ Cells optionally is selected from the group consisting of memory cells, central memory T ($T_{CM}$) cells, effector memory cells ($T_{EM}$), stem central memory ($T_{SCM}$) cells, T effector ($T_E$) cells, effector memory RA T ($T_{EMRA}$) cells, naïve T (TN) cells and/or regulatory T ($T_{REG}$) cells, and/or comprises bulk T cells.

38. The method of any one of embodiments 36-37, further comprising analyzing the apheresis sample or the T cells after shipping and before cryogenically storing the cells.

39. The method of any one of embodiments 36-38, further comprising adding a freezing solution to the apheresis sample or the T cells after shipping and before cryogenically storing the cells.

40. The method of embodiment 38, further comprising adding a freezing solution to the apheresis sample or the T cells after shipping and before cryogenically storing the cells, wherein the freezing solution is optionally selected based on the analyzing of the apheresis sample or the T cells after shipping and before cryogenically storing the cells.

41. The method of any one of embodiments 29-40, further comprising thawing the cryogenically stored cells.

42. The method of embodiment 41, further comprising analyzing the cells following the thawing.

43. The method of embodiment 42, further comprising selecting conditions for further modification of the cells based on the analysis following the thawing.

44. A method of treatment comprising: obtaining and optionally thawing a cryogenically frozen sample of cells, optionally comprising T cells, derived from a subject, wherein, prior to said obtaining, the cells have been cryogenically frozen for a period of at least 1, 2, 3, 4, 5, 6, 7, 8, 9, 10, 11, 12 months, or at least 1, 2, 3, 4, 5, 6, 7, 8, 9, or 10 years; modifying the cells to express a recombinant antigen receptor; and administering the cells to the subject.

45. The method of embodiment 44, wherein the sample has been frozen and/or stored according to the method of any of embodiments 1-43.

Additional Exemplary Embodiments I

1. A method for producing a composition of engineered cells, the method comprising: (a) incubating, under stimulating conditions, an input composition comprising T cells enriched for CD4+ primary human T cells, said stimulating conditions comprising the presence of (i) a stimulatory reagent capable of activating one or more intracellular signaling domains of one or more components of a TCR complex and/or one or more intracellular signaling domains of one or more costimulatory molecules and (ii) one or more cytokines, thereby generating a stimulated composition; and (b) introducing a recombinant receptor into the stimulated composition, thereby generating an engineered composition comprising engineered T cells, wherein the input composition is or is derived from a sample that has been cryogenically stored for a period of at least 1, 2, 3, 4, 5, 6, 7, 8, 9, 10, 11, 12 months, or at least 1, 2, 3, 4, 5, 6, 7, 8, 9, or 10 years.

2. The method of embodiment 1, wherein the stimulatory reagent comprises a primary agent that specifically binds to a member of a TCR complex, optionally that specifically binds to CD3.

3. The method of embodiment 2, wherein the stimulatory reagent further comprises a secondary agent that specifically binds to a T cell costimulatory molecule, optionally wherein the costimulatory molecule is selected from CD28, CD137 (4-1-BB), OX40, or ICOS.

4. The method of embodiment 2 or embodiment 3, wherein the primary and/or secondary agents comprise an antibody, optionally wherein the stimulatory reagent comprises incubation with an anti-CD3 antibody and an anti-CD28 antibody, or an antigen-binding fragment thereof.

5. The method of any one of embodiments 2-4, wherein the primary agent and/or secondary agent are present on the surface of a solid support 6. The method of embodiment 5, wherein the solid support is or comprises a bead.

7. The method of embodiment 6, wherein the bead comprises a diameter of greater than or greater than about 3.5 μm but no more than about 9 μm or no more than about 8 μm or no more than about 7 μm or no more than about 6 μm or no more than about 5 μm.

8. The method of embodiment 6 or embodiment 7, wherein the bead comprises a diameter of or about 4.5 μm.

9. The method of any one of embodiments 6-8, wherein the bead is inert.

10. The method of any one of embodiments 6-9, wherein the bead is or comprises a polystyrene surface.

11. The method of any one of embodiments 6-10, wherein the bead is magnetic or superparamagnetic.
12. The method of any one of embodiments 6-11, wherein the ratio of beads to cells is less than 3:1.
13. The method of any one of embodiments 6-12, wherein the ratio of beads to cells is from or from about 2:1 to 0.5:1.
14. The method of any one of embodiments 6-13, wherein the ratio of beads to cells is at or at about 1:1.
15. The method of any one of embodiments 1-14, wherein the introducing comprises transducing cells of the stimulated composition with a viral vector comprising a polynucleotide encoding the recombinant receptor.
16. The method of embodiment 15, wherein the viral vector is a retroviral vector.
17. The method of embodiment 15 or embodiment 16, wherein the viral vector is a lentiviral vector or gammaretroviral vector.
18. The method of any one of embodiments 15-17, wherein the introducing is carried out in the presence of a transduction adjuvant.
19. The method of any one of embodiments 1-18, wherein the introducing comprises transfecting the cells of the stimulated composition with a vector comprising a polynucleotide encoding the recombinant receptor.
20. The method of embodiment 19, wherein the vector is a transposon, optionally a Sleeping Beauty (SB) transposon or a Piggybac transposon.
21. The method of any one of embodiments 1-20, further comprising cultivating the engineered composition under conditions to promote proliferation or expansion of the engineered cells, thereby producing an output composition comprising the engineered T cells.
22. The method of embodiment 21, wherein the stimulatory reagent is removed from the engineered composition prior to the cultivating.
23. The method of embodiment 22, wherein removing the beads comprises exposing cells of the engineered composition to a magnetic field.
24. The method of any one of embodiments 21-23, wherein at least a portion of the cultivating is performed with continual mixing and/or perfusion.
25. A method of producing an engineered cell composition comprising: (a) incubating, under stimulating conditions, an input composition comprising primary T cells enriched for one or both of CD4+ and CD8+ primary human T cells, said stimulating conditions comprising the presence of (i) a stimulatory reagent capable of activating one or more intracellular signaling domains of one or more components of a TCR complex and/or one or more intracellular signaling domains of one or more costimulatory molecules and (ii) one or more cytokines, thereby generating a stimulated composition; and (b) introducing a recombinant receptor into the stimulated composition, thereby generating an engineered composition comprising engineered T cells, wherein the input composition is or is derived from a sample that has been cryogenically stored for a period of at least 1, 2, 3, 4, 5, 6, 7, 8, 9, 10, 11, 12 months, or at least 1, 2, 3, 4, 5, 6, 7, 8, 9, or 10 years.
26. The method of embodiment 24 or embodiment 35, wherein the stimulatory reagent comprises a primary agent that specifically binds to a member of a TCR complex, optionally that specifically binds to CD3.
27. The method of embodiment 26, wherein the stimulatory reagent further comprises a secondary agent that specifically binds to a T cell costimulatory molecule, optionally wherein the costimulatory molecule is selected from CD28, CD137 (4-1-BB), OX40, or ICOS.
28. The method of embodiment 26 or embodiment 27, wherein the primary and/or secondary agents comprise an antibody, optionally wherein the stimulatory reagent comprises incubation with an anti-CD3 antibody and an anti-CD28 antibody, or an antigen-binding fragment thereof.
29. The method of any one of embodiments 26-28, wherein the primary agent and/or secondary agent are present on the surface of a solid support.
30. The method of embodiment 29, wherein the solid support is or comprises a bead.
31. The method of embodiment 30, wherein the bead comprises a diameter of greater than or greater than about 3.5 μm but no more than about 9 μm or no more than about 8 μm or no more than about 7 μm or no more than about 6 μm or no more than about 5 μm.
32. The method of embodiment 30 or embodiment 31, wherein the bead comprises a diameter of or about 4.5 μm.
33. The method of any one of embodiments 30-32, wherein the bead is inert.
34. The method of any one of embodiments 30-33, wherein the bead is or comprises a polystyrene surface.
35. The method of any one of embodiments 30-34, wherein the bead is magnetic or superparamagnetic.
36. The method of any one of embodiments 30-35, wherein the ratio of beads to cells is less than 3:1.
37. The method of any one of embodiments 30-36, wherein the ratio of beads to cells is from or from about 2:1 to 0.5:1.
38. The method of any one of embodiments 30-37, wherein the ratio of beads to cells is at or at about 1:1.
39. The method of any one of embodiments 24-38, wherein the introducing comprises transducing cells of the stimulated composition with a viral vector comprising a polynucleotide encoding the recombinant receptor.
40. The method of embodiment 39, wherein the viral vector is a retroviral vector.
41. The method of embodiment 39 or embodiment 40, wherein the viral vector is a lentiviral vector or gammaretroviral vector.
42. The method of any one of embodiments 24-41, wherein the introducing is carried out in the presence of a transduction adjuvant.
43. The method of any one of embodiments 24-38, wherein the introducing comprises transfecting the cells of the stimulated composition with a vector comprising a polynucleotide encoding the recombinant receptor.
44. The method of embodiment 43, wherein the vector is a transposon, optionally a Sleeping Beauty (SB) transposon or a Piggybac transposon.
45. The method of embodiment 24 or embodiment 25, wherein the engineered cell composition does not comprise a stimulatory reagent and/or the stimulatory reagent has been substantially removed from the composition prior to the cultivating, said stimulatory reagent comprising a reagent capable of activating one or more intracellular signaling domains of one or more components of a TCR complex and/or one or more intracellular signaling domains of one or more costimulatory molecules.

46. The method of any one of embodiments 21-45, wherein the cultivating is performed at least until the output composition comprises a threshold number of T cells.
47. The method of embodiment 46, wherein the cultivating is continued for at least one day after the threshold number of T cells is reached.
48. The method of any one of embodiments 21-47, wherein subsequent to the cultivating, collecting cells of the output composition.
49. The method of any of embodiments 21-48, further comprising formulating cells of the output composition for cryopreservation and/or administration to a subject, optionally in the presence of a pharmaceutically acceptable excipient.
50. The method of embodiment 49, wherein the cells of the output composition are formulated in the presence of a cryoprotectant.
51. The method of embodiment 50, wherein the cryoprotectant comprises DMSO.
52. The method of any of embodiments 49-51, wherein the cells of the output composition are formulated in a container, optionally a vial or a bag.
53. The method of any one of embodiments 1-38, further comprising isolating the CD4+ and/or the CD8+ T cells from a biological sample prior to the incubating.
54. The method of embodiment 53, wherein the isolating comprises, selecting cells based on surface expression of CD4 and/or CD8, optionally by positive or negative selection.
55. The method of embodiment 53 or embodiment 54, wherein the isolating comprises carrying out immunoaffinity-based selection.
56. The method of any one of embodiments 53-55, wherein the biological sample comprises primary T cells obtained from a subject.
57. The method of embodiment 56, wherein the subject is a human subject.
58. The method of anyone of embodiments 53-55, wherein the biological sample is or comprises a whole blood sample, a buffy coat sample, a peripheral blood mononuclear cells (PBMC) sample, an unfractionated T cell sample, a lymphocyte sample, a white blood cell sample, an apheresis product, or a leukapheresis product.
59. The method of any one of embodiments 53-55, wherein the biological sample is or comprises a cryopreserved apheresis product or a cryopreserved leukapheresis product.
60. The method of any one of embodiments 1-59, wherein the recombinant receptor is capable of binding to a target antigen that is associated with, specific to, and/or expressed on a cell or tissue of a disease, disorder or condition.
61. The method of embodiment 60, wherein the disease, disorder or condition is an infectious disease or disorder, an autoimmune disease, an inflammatory disease, or a tumor or a cancer.
62. The method of embodiment 60 or embodiment 61, wherein the target antigen is a tumor antigen.
63. The method of any one of embodiments 60-62, wherein the target antigen is selected from among 5T4, 8H9, avb6 integrin, B7-H6, B cell maturation antigen (BCMA), CA9, a cancer-testes antigen, carbonic anhydrase 9 (CAIX), CCL-1, CD19, CD20, CD22, CEA, hepatitis B surface antigen, CD23, CD24, CD30, CD33, CD38, CD44, CD44v6, CD44v7/8, CD123, CD138, CD171, carcinoembryonic antigen (CEA), CE7, a cyclin, cyclin A2, c-Met, dual antigen, EGFR, epithelial glycoprotein 2 (EPG-2), epithelial glycoprotein 40 (EPG-40), EPHa2, ephrinB2, erb-B2, erb-B3, erb-B4, erbB dimers, EGFR vlll, estrogen receptor, Fetal AchR, folate receptor alpha, folate binding protein (FBP), FCRL5, FCRH5, fetal acetylcholine receptor, G250/CAIX, GD2, GD3, gp100, G Protein Coupled Receptor 5D (GPCR5D), Her2/neu (receptor tyrosine kinase erbB2), HMW-MAA, IL-22R-alpha, IL-13 receptor alpha 2 (IL-13Ra2), kinase insert domain receptor (kdr), kappa light chain, Lewis Y, L1-cell adhesion molecule (L1-CAM), Melanoma-associated antigen (MAGE)-A1, MAGE-A3, MAGE-A6, MART-1, mesothelin, murine CMV, mucin 1 (MUC1), MUC16, NCAM, NKG2D, NKG2D ligands, NY-ESO-1, O-acetylated GD2 (OGD2), oncofetal antigen, Preferentially expressed antigen of melanoma (PRAME), PSCA, progesterone receptor, survivin, ROR1, TAG72, EGFR, VEGF receptors, VEGF-R2, Wilms Tumor 1 (WT-1), a pathogen-specific antigen and an antigen associated with a universal tag.
64. The method of any one of embodiments 1-63, wherein the recombinant receptor is or comprises a functional non-TCR antigen receptor or a TCR or antigen-binding fragment thereof.
65. The method of any one of embodiments 1-64, wherein the recombinant receptor is a chimeric antigen receptor (CAR).
66. The method of any one of embodiments 1-65, wherein the recombinant receptor is an anti-CD19 CAR.
67. The method of embodiment 65, wherein the chimeric antigen receptor comprises an extracellular domain comprising an antigen-binding domain.
68. The method of embodiment 67, wherein the antigen-binding domain is or comprises an antibody or an antibody fragment thereof, which optionally is a single chain fragment.
69. The method of embodiment 68, wherein the fragment comprises antibody variable regions joined by a flexible linker.
70. The method of embodiment 68 or embodiment 69, wherein the fragment comprises an scFv.
71. The method of any one of embodiments 67-70, wherein the chimeric antigen receptor further comprises a spacer and/or a hinge region.
72. The method of any of embodiments 67-71, wherein the chimeric antigen receptor comprises an intracellular signaling region.
73. The method of embodiment 72, wherein the intracellular signaling region comprises an intracellular signaling domain.
74. The method of embodiment 73, wherein the intracellular signaling domain is or comprises a primary signaling domain, a signaling domain that is capable of inducing a primary activation signal in a T cell, a signaling domain of a T cell receptor (TCR) component, and/or a signaling domain comprising an immunoreceptor tyrosine-based activation motif (ITAM).
75. The method of embodiment 74, wherein the intracellular signaling domain is or comprises an intracellular signaling domain of a CD3 chain, optionally a CD3-zeta (CD34) chain, or a signaling portion thereof.
76. The method of any one of embodiments 72-75, wherein the chimeric antigen receptor further comprises a transmembrane domain disposed between the extracellular domain and the intracellular signaling region.

77. The method of any one of embodiments 72-76, wherein the intracellular signaling region further comprises a costimulatory signaling region.

78. The method of embodiment 77, wherein the costimulatory signaling region comprises an intracellular signaling domain of a T cell costimulatory molecule or a signaling portion thereof.

79. The method of embodiment 77 or embodiment 78, wherein the costimulatory signaling region comprises an intracellular signaling domain of a CD28, a 4-1BB or an ICOS or a signaling portion thereof.

80. The method of any one of embodiments 77-79, wherein the costimulatory signaling region is between the transmembrane domain and the intracellular signaling region.

81. The method of any one of embodiments 46-47, wherein the output composition comprising the threshold number or greater number of cells is produced among greater than or greater than about 85%, greater than or greater than about 90% or greater than or greater than about 95% of the iterations of the method.

82. A composition comprising engineered cells produced by a method of any one of embodiments 1-79.

83. The composition of embodiment 82, further comprising a pharmaceutically acceptable carrier.

84. The composition of embodiment 82 or embodiment 83, comprising a cryoprotectant, optionally DMSO.

85. An article of manufacture, comprising the composition of any of embodiments 80-82, and instructions for administering the output composition to a subject.

86. The article of manufacture of embodiment 85, wherein the subject has a disease or condition, optionally wherein the recombinant receptor specifically recognizes or specifically bind to an antigen associated with, or expressed or present on cells of, the disease or condition.

87. The article of manufacture of embodiment 85 or embodiment 86, wherein the output composition is a composition of engineered CD4+ T cells.

88. The article of manufacture of embodiment 85 or embodiment 86, wherein the output composition is a engineered composition of CD8+ T cells.

89. An article of manufacture comprising a composition of engineered CD4+ T cells produced by the method of any one of embodiments 1-25 or 26-81, a composition of engineered CD8+ T cells produced by the method of any of claim 2-23, 25 or 26-81, and instructions for administering the engineered CD4+ T cells and the engineered CD8+ T cells to a subject.

90. The article of manufacture of embodiment 89, wherein the instructions specify separately administering the CD4+ T cells and CD8+ T cells to the subject.

91. The article of manufacture of embodiment 89 or embodiment 90, wherein the instructions specify administering the CD4+ T cells and the CD8+ T cells to the subject at a desired ratio.

Additional Exemplary Embodiments II

1. A method of storing a biological sample, the method comprising obtaining a biological sample from a subject dividing the biological sample into two or more separate containers cryopreserving the biological sample storing the cryopreserved biological sample.

2. The method of embodiment 1, wherein the subject is a human subject.

3. The method of any one of embodiments 1-2, wherein the biological sample is an apheresis product or a leukapheresis product.

4. The method of any one of embodiments 1-3, wherein the two or more separate containers are each selected from the group consisting of a cryogenic bag and/or a cryogenic vial.

5. The method of any one of embodiments 1-4, wherein the two or more separate containers contain thereon unique identifier.

6. The method of embodiment 5, wherein the unique identifier comprises any one or more of textual information, an RFID tag, a QR code, and/or a barcode.

7. The method of any one of embodiments 5-6, wherein the unique identifier information comprises information about any one or more of the following categories: the identity of the subject, location of the sample storage, storage and/or handling instructions, date of receipt, date of cryopreservation, expiration date, and intended use.

8. The method of any one of embodiments 1-7, wherein the biological sample is stored for a period of time greater than or equal to 12 hours, 24 hours, 36 hours, 48 hours, 1 week, 2 weeks, 3 weeks, or 4 weeks, 1 month, 2 months, 3 months, 4 months, 5 months, 6 months, 7 months, 8 months, 9 months, 10 months, 11 months, 1 year, 2 years, 3 years, 4 years, 5 years, 6 years, 7 years, 8 years, 9 years, 10 years, 11 years, 12 years, 13 years, 14 years, 15 years, 16 years, 17 years, 18 years, 19 years, 20 years, 25 years, 30 years, 35 years, or 40 years.

9. A method of storing a biological sample, the method comprising: (a) obtaining a biological sample from a subject; (b) cryopreserving the biological sample in one or more containers; and (c) storing the cryopreserved biological sample for a period of time greater than or equal to 12 hours, 24 hours, 36 hours, 48 hours, 1 week, 2 weeks, 3 weeks, or 4 weeks, 1 month, 2 months, 3 months, 4 months, 5 months, 6 months, 7 months, 8 months, 9 months, 10 months, 11 months, 1 year, 2 years, 3 years, 4 years, 5 years, 6 years, 7 years, 8 years, 9 years, 10 years, 11 years, 12 years, 13 years, 14 years, 15 years, 16 years, 17 years, 18 years, 19 years, 20 years, 25 years, 30 years, 35 years, or 40 years.

10. The method of embodiment 9, wherein the subject is a human subject.

11. The method of any one of embodiments 9-10, wherein the biological sample is an apheresis product or a leukapheresis product.

12. The method of any one of embodiments 9-11, wherein the one or more containers are each selected from the group consisting of a cryogenic bag and/or a cryogenic vial.

13. The method of any one of embodiments 9-12, wherein the one or more separate containers contain thereon unique identifier.

14. The method of embodiment 13, wherein the unique identifier comprises any one or more of textual information, an RFID tag, a QR code, and/or a barcode.

15. The method of any one of embodiments 13-14, wherein the unique identifier information comprises information about any one or more of the following categories: the identity of the subject, location of the sample storage, storage and/or handling instructions, date of receipt, date of cryopreservation, expiration date, and intended use.

16. A method of obtaining a biological sample corresponding to a subject, the method comprising: (a) locating a cryopreserved sample in a central facility based on a unique identifier associating the sample with the subject; and (b) obtaining the cryopreserved sample.
17. The method of embodiment 16, wherein the biological sample is genetically matched to the subject, is suitable for producing an autologous product for the subject, and/or contains cells of the subject.

Additional Exemplary Embodiments III

1. A method comprising cryogenically storing cells from a biological sample derived from a donor, wherein the cells are obtained from the donor at a point in time that is after the donor is diagnosed with, or deemed to have or be suspected of having, a disease or condition, and before the donor has received one or more treatments for the disease or condition; and wherein the cells are frozen in a controlled rate freezer using a stepwise freezing profile comprising at least one step wherein the sample and/or chamber is cooled at a rate greater than 1° C. per minute.
2. A method comprising cryogenically storing cells from a biological sample derived from a donor, wherein the cells have been obtained from the donor at a point in time after the donor has been deemed refractory to, or has experienced a relapse following a treatment regimen for a disease or condition, and before the donor has received a subsequent treatment for the disease or condition.
3. A method comprising cryogenically storing cells from a biological sample derived from a donor, wherein the cells have been obtained from the donor at a point in time at which the donor has not been diagnosed with or is not known to or is not suspected of having, a disease or condition, and wherein the cells are frozen in a controlled rate freezer using a stepwise freezing profile comprising at least one step wherein the sample and/or chamber is cooled at a rate greater than 1° C. per minute.
4. A method comprising: (a) cryogenically freezing cells from a biological sample derived from a donor, and (b) storing the cryogenically frozen cells for a period of time, wherein the cells are or were obtained from the donor at a point in time that is (i) after the donor is diagnosed with, or deemed to have or be suspected of having, a disease or condition, and before the donor has received a treatment for the disease or condition; or (ii) after the donor has been deemed refractory to, or has experienced a relapse following a treatment regimen for a disease or condition, and before the donor has received a subsequent treatment for the disease or condition, and wherein during the storage period of time, the donor receives or received at least one treatment for the disease or condition.
5. A method comprising: (a) cryogenically freezing cells from a biological sample derived from a donor, and (b) storing the cryogenically frozen cells for a period of time, wherein the cells are or were obtained from the donor at a point in time that is (i) after the donor is diagnosed with, or deemed to have or be suspected of having, a disease or condition, and before the donor has received a treatment for the disease or condition; or (ii) after the donor has been deemed refractory to, or has experienced a relapse following a treatment regimen for a disease or condition, and before the donor has received a subsequent treatment for the disease or condition, and wherein the cells are cryogenically stored for a period of time greater than or equal to 12 hours, 24 hours, 36 hours, 48 hours, 1 week, 2 weeks, 3 weeks, or 4 weeks, 1 month, 2 months, 3 months, 4 months, 5 months, 6 months, 7 months, 8 months, 9 months, 10 months, 11 months, 1 year, 2 years, 3 years, 4 years, 5 years, 6 years, 7 years, 8 years, 9 years, 10 years, 11 years, 12 years, 13 years, 14 years, 15 years, 16 years, 17 years, 18 years, 19 years, 20 years, 25 years, 30 years, 35 years, or 40 years, or until the donor needs the cells.
6. A method comprising: (a) cryogenically freezing cells from a biological sample derived from a donor, and (b) administering a therapeutically effective amount of a composition comprising engineered T cells generated from the cryogenically frozen cells to a subject in need thereof, wherein the cells are or were obtained from the donor at a point in time that is (i) after the donor is diagnosed with, or deemed to have or be suspected of having, a disease or condition, and before the donor has received a treatment for the disease or condition; or (ii) after the donor has been deemed refractory to, or has experienced a relapse following a treatment regimen for a disease or condition, and before the donor has received a subsequent treatment for the disease or condition, and wherein between the freezing and administering, the donor receives or received at least one treatment for the disease or condition.
7. A method comprising: (a) cryogenically freezing cells from a biological sample derived from a donor, thereby generating a cryogenically frozen cell composition, and (b) engineering cells of the cryogenically frozen cell composition to generate a composition comprising engineered T cells, wherein the cells are or were obtained from the donor at a point in time that is (i) after the donor is diagnosed with, or deemed to have or be suspected of having, a disease or condition, and before the donor has received a treatment for the disease or condition; or (ii) after the donor has been deemed refractory to, or has experienced a relapse following a treatment regimen for a disease or condition, and before the donor has received a subsequent treatment for the disease or condition, and wherein between the freezing and engineering, the donor receives or received at least one treatment for the disease or condition.
8. A method of treatment comprising administering a therapeutically effective amount of engineered T cells to a subject in need thereof, wherein the cells are or were obtained from the subject at a point in time that is (i) after the subject is diagnosed with, or deemed to have or be suspected of having, a disease or condition, and before the subject has received a treatment for the disease or condition; or (ii) after the subject has been deemed refractory to, or has experienced a relapse following a treatment regimen for a disease or condition, and before the subject has received a subsequent treatment for the disease or condition, and wherein after the cells are or were obtained from the subject and before the administering of the engineered T cells, the subject receives or received at least one treatment for the disease or condition.

9. A method for producing a composition of engineered cells comprising: (a) obtaining and optionally thawing cryogenically stored cells, and (b) introducing a recombinant receptor into the cryogenically stored cells, thereby generating an engineered composition comprising engineered T cells, wherein the cells are cryogenically stored after harvesting from a donor at a point in time that is (i) after the donor is diagnosed with, or deemed to have or be suspected of having, a disease or condition, and before the donor has received a treatment for the disease or condition; or (ii) after the donor has been deemed refractory to, or has experienced a relapse following a treatment regimen for a disease or condition, and before the donor has received a subsequent treatment for the disease or condition, and wherein after cryogenic storage and before obtaining the cryogenically stored cells, the donor receives or received at least one treatment for the disease or condition.
10. The method of any one of embodiments 1-9, wherein the biological sample is or is derived from an apheresis sample, optionally a leukapheresis sample, and/or wherein the sample contains white blood cells and/or lymphocytes and/or wherein the cells or the blood cells in the sample consist essentially of leukocytes, or wherein at least 80%, 85%, 90%, 95%, 96%, 97%, 98%, or 99% of the cells in the sample or at least 80%, 85%, 90%, 95%, 96%, 97%, 98%, or 99% of the blood cells in the sample are leukocytes.
11. The method of any one of embodiments 1-10, wherein the cells have not been subjected to an immunoaffinity-based and/or target-specific selection and/or enrichment step for a blood cell population and/or a T cell population and/or a T cell subset, before being cryogenically stored.
12. The method of any one of embodiments 1-10, wherein the cells have been subjected to an immunoaffinity-based and/or target-specific selection and/or enrichment step for a blood cell and/or T cell population before being cryogenically stored, optionally wherein the method further comprises carrying out said selection or enrichment prior to said cryogenic storage.
13. The method of embodiment 12, wherein the selection step and/or enrichment comprises an immunoaffinity-based selection and/or comprises positive or negative selection.
14. The method of any one of embodiments 12-13, wherein: the selection step and/or enrichment comprises enrichment and/or isolation of CD4+ cells or a subset thereof and/or CD8+ cells or a subset thereof, wherein enrichment or isolation of the CD4+ cells or subset thereof is carried out either separately or in combination with the selection and/or isolation of the CD8+ cells or subset thereof, optionally wherein the subset of CD8+ cells and/or the subset of CD4+ cells optionally is selected from the group consisting of memory cells, central memory T (TCM) cells, effector memory cells (TEM), stem central memory (TSCM) cells, T effector (TE) cells, effector memory RA T (TEMRA) cells, naïve T (TN) cells, and/or regulatory T (TREG) cells.
15. The method of any one of embodiments 1-14, wherein the cells comprise or are enriched for T cells.
16. The method of embodiment 15, wherein the T cells comprise or are enriched for CD4+ T cells or a subset thereof, CD8+ T cells or a subset thereof, or a mixture thereof, wherein the subset of CD8+ cells and/or the subset of CD4+ cells optionally is selected from the group consisting of memory cells, central memory T (TCM) cells, effector memory cells (TEM), stem central memory (TSCM) cells, T effector (TE) cells, effector memory RA T (TEMRA) cells, naïve T (TN) cells and/or regulatory T (TREG) cells.
17. The method of any one of embodiments 1-16, further comprising, prior to cryogenically storing the cells, combining the cells with a cryopreservation medium.
18. The method of embodiment 17, wherein the cryopreservation medium comprises about 10% dimethyl sulfoxide (DMSO) and a serum protein, optionally human serum albumin, optionally about 4% human serum albumin, and/or wherein the freezing solution comprises and/or the final concentration of the biological sample comprises between about 1% and about 20%, between about 3% and about 9%, or between about 6% and about 9% by volume DMSO and/or comprises about 3%, about 4%, about 5%, about 5.5%, about 6%, about 6.5%, about 7%, about 7.5%, about 8%, about 8.5%, about 9%, about 9.5%, or about 10% by volume DMSO.
19. The method of any one of embodiments 2 or 4-18, wherein the cryogenic storage comprises lowering the temperature at a rate of at or about 1° C. per minute, optionally until the temperature reaches at or about −80° C.
20. The method of any one of embodiments 1-19, wherein the cells are cryogenically stored in a container placed in a vapor phase of liquid nitrogen, wherein the container is optionally a bag or vial.
21. The method of any one of embodiments 1-20, wherein the cells are cryogenically stored for a period of time greater than or equal to 12 hours, 24 hours, 36 hours, 48 hours, 1 week, 2 weeks, 3 weeks, or 4 weeks, 1 month, 2 months, 3 months, 4 months, 5 months, 6 months, 7 months, 8 months, 9 months, 10 months, 11 months, 1 year, 2 years, 3 years, 4 years, 5 years, 6 years, 7 years, 8 years, 9 years, 10 years, 11 years, 12 years, 13 years, 14 years, 15 years, 16 years, 17 years, 18 years, 19 years, 20 years, 25 years, 30 years, 35 years, or 40 years.
22. The method of any one of embodiments 1-21, wherein the cells are stored for a period of time and wherein, after the period of time, the percentage of viable cells or viable T cells or subtype or subset thereof in the composition is from about 24% to about 100%, or is at least about 15, 20, 25, 30, 35, 40, 45, 50, 55, 60, 65, 70, 75, 80, 85, or 90%.
23. The method of any one of embodiments 1-22, wherein the disease is a cancer, an inflammatory disease or condition, an autoimmune disease or condition, or an infectious disease or condition.
24. The method of embodiment 23, wherein the cancer is chronic lymphocytic leukemia, acute lymphocytic leukemia, pro-lymphocytic leukemia, hairy cell leukemia, acute lymphocytic leukemia, null-acute lymphoblastic leukemia, Hodgkin's lymphoma, non-Hodgkin's lymphoma, diffuse large B cell lymphoma, multiple myeloma, follicular lymphoma, splenic, marginal zone lymphoma, mantle cell lymphoma, indolent B cell lymphoma, or acute myeloid leukemia.
25. The method of embodiment 23 or 24, wherein the cancer comprises cells expressing at least one of ROR1, EGFR, Her2, L1-CAM, CD19, CD20, CD22, mesothelin, CEA, and hepatitis B surface antigen, anti-folate receptor, CD23, CD24, CD30, CD33, CD38, CD44, EGFR, EGP-2, EGP-4, EPHa2, ErbB2, 3, or 4, FBP, fetal acethycholine receptor, GD2, GD3, HMW-MAA, IL-22R-alpha, IL-13R-alpha2, kdr, kappa light chain, Lewis Y, L1-cell adhesion molecule, MAGE-A1, MUC1, MUC16, B cell maturation antigen (BCMA), FCRL5/FCRH5, GPRC5D, PSCA, NKG2D Ligands, NY-ESO-1, MART-1, gp100, oncofetal antigen, TAG72, VEGF-R2, carcinoembryonic antigen (CEA), prostate specific antigen, PSMA, Her2/neu, estrogen receptor, progesterone receptor, ephrinB2, CD123, CS-1, c-Met, GD-2, and MAGE A3, CE7, Wilms Tumor 1 (WT-1), and a cyclin, such as cyclin A1 (CCNA1).

26. The method of any one of embodiments 1-25, wherein the treatment is chemotherapy, radiation, surgery, cell therapy, and/or is a debulking treatment.

27. The method of embodiment 26, wherein the treatment comprises one of more of the following treatments alone or in combination: cyclophosphamide, methotrexate, 5-fluorouracil, doxorubicin, mustine, vincristine, procarbazine, prednisolone, bleomycin, vinblastine, dacarbazine, etoposide, cisplatin, epirubicin, capecitabine, folinic acid, oxaliplatin, a small-molecule inhibitor, an immune cell, natural killer cells, lymphokine-activated killer cells, cytotoxic T cells, dendritic cells, 4000 cGy radiation, autologous stem cell rescue, stem cell transplant, bone marrow transplant, hematopoietic stem cell transplantation (HSCT), CAR T cell therapy, Tisagenlecleucel, Axicabtagene ciloleucel, cytarabine, high-dose cytarabine, daunorubicin (daunomycin), idarubicin, cladribine, bortezomib, carfilzomib, thalidomide, lenalidomide, pomalidomide, corticosteroids, prednisone, dexamethasone, an alkylating agent, chlorambucil, bendamustine, ifosfamide, a platinum drug, cisplatin, carboplatin, oxaliplatin, a purine analog, fludarabine, pentostatin, cladribine, an anti-metabolite, gemcitabine, methotrexate, pralatrexate, vincristine, doxorubicin, mitoxantrone, bleomycin, a proteasome inhibitor, a histone deacetylase inhibitor, romidepsin, belinostat, a kinase inhibitor, ibrutinib, idelalisib, an antibody, an anti-CD20 antibody, rituximab, obinutuzumab, ofatumumab, ibritumomab tiuxetan, an anti-CD52 antibody, alemtuzumab, an anti-CD30 antibody, brentuximab, vedotin, interferon, an immunomodulating agent, thalidomide, CHOP, CHOP+R (or R-CHOP), CVP, EPOCH, EPOCH+R, DHAP, DHAP+R (or R-DHAP), venetoclax, methylprednisolone, or a Bruton's tyrosine kinase inhibitor (BTKi).

28. The method of any one of embodiments 1-27, wherein the donor or subject is human.

29. The method of any one of embodiments 1-28, further comprising analyzing the cells before cryogenic storage, optionally by assessing surface expression of the cells for one or more phenotypic markers.

30. The method of any one of embodiments 1-29, further comprising thawing the cryogenically stored cells.

31. The method of any of embodiments 1-30, further comprising, following cryogenic storage and/or thawing of the cells, engineering the cells to express a recombinant or exogenous molecule, which optionally is a recombinant protein, optionally a recombinant receptor, which optionally is or comprises a T cell receptor (TCR), a chimeric receptor, and/or a chimeric antigen receptor.

32. The method of embodiment 31, wherein the recombinant molecule is a recombinant receptor that specifically recognizes or binds to an antigen expressed by, or specifically expressed by, cells associated with the disease or condition.

33. The method of any one of embodiments 1-32, wherein the number of the cells, when collected from the donor or subject, and/or total in the apheresis sample, is at or about or is no more than at or about $500\times10^6$, $1000\times10^6$, $2000\times10^6$, $3000\times10^6$, $4000\times10^6$, or $5000\times10^6$ or more total cells or total nucleated cells.

34. The method of any one of embodiments 1-33, further comprising enriching T cells from the sample prior to cryogenically storing the sample.

35. The method of embodiment 34, wherein the T cells are or comprise or are enriched for CD4+ T cells or a subset thereof, CD8+ T cells or a subset thereof, or a mixture thereof, optionally wherein the subset of CD8+ cells and/or the subset of CD4+ Cells optionally is selected from the group consisting of memory cells, central memory T (TCM) cells, effector memory cells (TEM), stem central memory (TSCM) cells, T effector (TE) cells, effector memory RA T (TEMRA) cells, naïve T (TN) cells and/or regulatory T (TREG) cells and/or wherein the sample is enriched for bulk T cells.

36. The method of any one of embodiments 1-35, further comprising formulating the sample in a cryogenic medium prior to cryogenically storing the sample.

37. The method of any one of embodiments 1-36, further comprising shipping the cells to a storage facility either before or after cryogenic freezing.

38. The method of embodiment 37, wherein the storage facility is a central or common repository storage facility.

39. The method of embodiment 37 or 38, wherein the sample is shipped in a cooled environment to the storage facility.

40. The method of any one of embodiments 36-39, further comprising enriching T cells from the sample after shipping and before cryogenically storing the cells.

41. The method of embodiment 40, wherein the T cells are or comprise or are enriched for CD4+ T cells or subset thereof, CD8+ T cells or subset thereof, or a mixture thereof, optionally wherein the subset of CD8+ cells and/or the subset of CD4+ Cells optionally is selected from the group consisting of memory cells, central memory T (TCM) cells, effector memory cells (TEM), stem central memory (TSCM) cells, T effector (TE) cells, effector memory RA T (TEMRA) cells, naïve T (TN) cells and/or regulatory T (TREG) cells, and/or comprises bulk T cells.

42. The method of embodiment 40 or embodiment 41, further comprising formulating the sample and/or the T cells in a cryogenic medium after shipping and before cryogenically storing the cells.

43. The method of any one of embodiments 1-42, further comprising thawing the cryogenically stored cells.

44. The method of any one of embodiments 1-43, wherein the sample is placed in a container marked with one or more codes or identifiers for cataloging the cells during processing, cryopreservation, and/or storage.

45. The method of embodiment 44, wherein the one or more codes or identifiers comprise text identifiers, barcodes, QR codes, RFIDs, or transponders.

46. The method of embodiment 44 or embodiment 45, wherein the one or more codes or identifiers correspond to or indicate the identity of one or more of: the donor, the sample, the vial, the container, the disease, and/or the storage facility.

47. The method of any one of embodiments 44-46, wherein the one or more codes or identifiers correspond to a code appearing on a patient identity bracelet or hospital or medical or collection facility system or paperwork.

erating an engineered composition comprising engineered T cells, and administering the cells to a subject.

49. The method of any one of embodiments 1-48, wherein the treatment does not comprise the engineered T cells or cells of the cryogenically frozen composition.

SEQUENCE LISTING

```
<160> NUMBER OF SEQ ID NOS: 3

<210> SEQ ID NO 1
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Glu Ser Lys Tyr Gly Pro Pro Cys Pro Pro Cys Pro
1               5                   10


<210> SEQ ID NO 2
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 2

Pro Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Pro
            20                  25                  30


<210> SEQ ID NO 3
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Gly Ser Ala Asp Asp Ala Lys Lys Asp Ala Ala Lys Lys Asp Gly Lys
1               5                   10                  15

Ser
```

48. The method of treatment comprising: obtaining and optionally thawing cryogenically stored cells through the methods of any one of embodiments 1-47, wherein, prior to said obtaining, the cells have been cryogenically stored for a period of at least 12 hours, 24 hours, 36 hours, 48 hours, 1 week, 2 weeks, 3 weeks, or 4 weeks, 1 month, 2 months, 3 months, 4 months, 5 months, 6 months, 7 months, 8 months, 9 months, 10 months, 11 months, 1 year, 2 years, 3 years, 4 years, 5 years, 6 years, 7 years, 8 years, 9 years, 10 years, 11 years, 12 years, 13 years, 14 years, 15 years, 16 years, 17 years, 18 years, 19 years, 20 years, 25 years, 30 years, 35 years, or 40 years; introducing a recombinant receptor into the stimulated composition, thereby gen-

The invention claimed is:

1. A method comprising cryogenically storing cells from a biological sample derived from a donor, the method comprising, (a) suspending a population of cells that are engineered to express a recombinant receptor in a cryopreservation medium to form a suspended composition, said cryopreservation medium comprising 0.1% to 50% dimethyl sulfoxide (DMSO) (v/v) and from 0.1% to 20% human serum albumin (HSA) (w/v), wherein the suspended composition has a cell density of about $10\times10^6$ cells/mL to about $150\times10^6$ cells/mL, and wherein the population of cells comprises at least 80% T cells and is for treating a disease or condition in the donor, and wherein the suspended composition is in a container at a surface area to volume (SA: V) ratio of 3 $cm^{-1}$ to 6 $cm^{-1}$, (b) cryogenically freezing the suspended composition in a controlled rate freezer comprising a chamber using a stepwise freezing profile to form cryogenically frozen cells, the stepwise freezing profile comprising a cooling step that cools the suspended composition or chamber at a rate of 1.2° C. per minute to a temperature of about −6° C., followed by a cooling step that cools the suspended composition or chamber at a rate of 25° C. per minute from about −6° C. until the suspended composition or chamber reaches a temperature of about −65° C., and (c) storing the cryogenically frozen cells.

2. The method of claim 1, wherein the cryopreservation medium comprises between about 1% and about 20% (v/v) dimethyl sulfoxide (DMSO).

3. The method of claim 1, wherein the cryopreservation medium comprises about 3% to about 9% (v/v) DMSO.

4. The method of claim 1, wherein the cryopreservation medium comprises about 7.5% (v/v) DMSO.

5. The method of claim 3, wherein the cryopreservation medium comprises about 0.2% to about 15% HSA (w/v).

6. The method of claim 1, wherein, before being cryogenically frozen, the cells have been subjected to:

(a) an immunoaffinity-based or target-specific selection step; or (b) an enrichment step for a blood cell population, a T cell population, or a T cell subset population.

7. The method of claim 6, wherein the blood cell population, the T cell population or the T cell subset population comprises:

(a) $CD4^+$ cells or a subset thereof and (b) $CD8^+$ cells or a subset thereof, wherein selection or enrichment of $CD4^+$ cells or a subset thereof is carried out either separately or in combination with selection or enrichment of $CD8^+$ cells or a subset thereof.

8. The method of claim 7, wherein the blood cell population, the T cell population or the T cell subset population comprises memory cells, central memory T ($T_{CM}$) cells, effector memory cells ($T_{EM}$), stem central memory ($T_{SCM}$) cells, T effector ($T_E$) cells, effector memory RA T ($T_{EMRA}$) cells, naïve T (TN) cells or regulatory T ($T_{REG}$) cells.

9. The method of claim 1, wherein the storing is at a temperature below −80° C.

10. The method of claim 1, wherein the stepwise freezing profile comprises cooling the chamber to a temperature above −80° C. or below −20° C. before storing the cryogenically frozen cells.

11. The method of claim 1, wherein the stepwise freezing profile comprises a series of multiple cooling and heating profiles.

12. The method of claim 1, wherein the storing of the cryogenically frozen cells is in the container placed in a vapor phase of liquid nitrogen.

13. The method of claim 1, wherein the storing is for a period of time greater than or equal to 24 hours.

14. The method of claim 13, wherein after the storing, at least about 70% of the cells in the suspended composition are viable.

15. The method of claim 1, wherein the disease or condition is a cancer, an inflammatory disease or condition, an autoimmune disease or condition, or an infectious disease or condition.

16. The method of claim 1, wherein the recombinant receptor comprises a T cell receptor (TCR) or a chimeric receptor.

17. The method of claim 1, wherein the recombinant receptor comprises a chimeric antigen receptor (CAR).

18. The method of claim 1, wherein the T cells comprise CD4+ and/or CD8+ T cells.

19. The method of claim 1, wherein the suspended composition has a cell density of about $10\times10^6$ cells/mL to about $70\times10^6$ cells/mL.

20. The method of claim 19, wherein the cryopreservation medium comprises about 1% to about 20% (v/v) dimethyl sulfoxide (DMSO).

21. The method of claim 19, wherein the cryopreservation medium comprises about 3% to about 9% (v/v) DMSO.

22. The method of claim 19, wherein the cryopreservation medium comprises about 7.5% (v/v) DMSO.

23. The method of claim 19, wherein the cryopreservation medium comprises about 0.2% to about 15% HSA (w/v).

24. The method of claim 19, wherein the stepwise freezing profile comprises cooling the chamber to a temperature above −80° C. or below −20° C. before storing the cryogenically frozen cells.

25. The method of claim 19, wherein the recombinant receptor comprises a chimeric antigen receptor (CAR).

26. The method of claim 1, wherein the suspended composition has a cell density of about $15\times10^6$ cells/mL to about $60\times10^6$ cells/mL.

27. The method of claim 26, wherein the cryopreservation medium comprises about 1% to about 20% (v/v) dimethyl sulfoxide (DMSO).

28. The method of claim 26, wherein the cryopreservation medium comprises about 3% to about 9% (v/v) DMSO.

29. The method of claim 26, wherein the cryopreservation medium comprises about 7.5% (v/v) DMSO.

30. The method of claim 26, wherein the cryopreservation medium comprises about 0.2% to about 15% HSA (w/v).

31. The method of claim 26, wherein the stepwise freezing profile comprises cooling the chamber to a temperature above −80° C. or below −20° C. before storing the cryogenically frozen cells.

32. The method of claim 26, wherein the recombinant receptor comprises a chimeric antigen receptor (CAR).

33. The method of claim 1, wherein the stepwise freezing profile comprises the following steps in the following order:

(a) a holding step at 4.0° C.;

(b) the cooling step that cools the suspended composition or chamber at a rate of 1.2° C. per minute to a temperature of about −6° C.;

(c) the cooling step that cools the suspended composition or chamber at a rate of 25° C. per minute from about −6° C. until the suspended composition or chamber reaches a temperature of about −65° C.;

(d) a heating step of 15° C. per minute until the suspended composition or chamber reaches a temperature of about −30° C.;

(e) a cooling step of 1° C. per minute until the suspended composition or chamber reaches a temperature of about −40° C.;

(f) a cooling step of 10° C. per minute until the suspended composition or chamber reaches about −90° C.; and (g) a holding step at −90° C.

34. A method of cryogenically storing engineered cells, the method comprising, (a) suspending a population of cells that are engineered to express a recombinant receptor in a cryopreservation medium to form a suspended composition, said cryopreservation medium comprising 3% to 9% dimethyl sulfoxide (DMSO) (v/v) and from 1% to 5% human serum albumin (HSA) (w/v), wherein the suspended composition has a cell density of about $10\times10^6$ cells/mL to about $150\times10^6$ cells/mL, and wherein the population of cells comprises at least 80% T cells, and wherein the suspended composition is in a container at a surface area to volume (SA: V) ratio of 3 $cm^{-1}$ to 6 $cm^{-1}$, (b) cryogenically freezing the suspended composition in a controlled rate freezer comprising a chamber using a stepwise freezing profile to form cryogenically frozen cells, the stepwise freezing profile comprising a cooling step that cools the suspended composition or chamber at a rate of 1.2° C. per minute to a temperature of about −6° C., followed by a cooling step that cools the suspended composition or chamber at a rate of 25° C. per minute from about −6° C. until the suspended composition or chamber reaches a temperature of about −65° C., and (c) storing the cryogenically frozen cells at a temperature below −80° C. for a period of time greater than or equal to 24 hours.

35. The method of claim 34, wherein the recombinant receptor comprises a chimeric antigen receptor (CAR).

* * * * *